(12) United States Patent
James et al.

(10) Patent No.: US 10,330,763 B2
(45) Date of Patent: Jun. 25, 2019

(54) SELECTIVE SAMPLING FOR ASSESSING STRUCTURAL SPATIAL FREQUENCIES WITH SPECIFIC CONTRAST MECHANISMS

(71) Applicant: bioProtonics, LLC, Santa Ynez, CA (US)

(72) Inventors: Kristin James, Santa Barbara, CA (US); Timothy W. James, Santa Barbara, CA (US)

(73) Assignee: BIOPROTONICS INC., Santa Ynez, CA (US)

( * ) Notice: Subject to any disclaimer, the term of this patent is extended or adjusted under 35 U.S.C. 154(b) by 0 days.

(21) Appl. No.: 16/044,393

(22) Filed: Jul. 24, 2018

(65) Prior Publication Data

US 2018/0329009 A1   Nov. 15, 2018

Related U.S. Application Data

(60) Division of application No. 15/604,465, filed on May 24, 2017, now Pat. No. 10,061,003, which is a (Continued)

(51) Int. Cl.
*G01R 33/56* (2006.01)
*G01R 33/561* (2006.01)
(Continued)

(52) U.S. Cl.
CPC .......... *G01R 33/5601* (2013.01); *A61B 5/055* (2013.01); *A61B 5/7203* (2013.01);
(Continued)

(58) Field of Classification Search
CPC ............ G01R 33/5601; G01R 33/5619; G01R 33/4818; G01R 33/4833; G01R 33/4835;
(Continued)

(56) References Cited

U.S. PATENT DOCUMENTS 5,565,777 A * 10/1996 Kanayama ........... G01R 33/465
324/309
7,903,251 B1 * 3/2011 Farr .................... G01R 33/5608
356/407

(Continued)

*Primary Examiner* — Dixomara Vargas
(74) *Attorney, Agent, or Firm* — Felix L. Fischer

(57) ABSTRACT

The disclosed embodiments provide a method for acquiring MR data at resolutions down to tens of microns for application in in vivo diagnosis and monitoring of pathology for which changes in fine tissue textures can be used as markers of disease onset and progression. Bone diseases, tumors, neurologic diseases, and diseases involving fibrotic growth and/or destruction are all target pathologies. Further the technique can be used in any biologic or physical system for which very high-resolution characterization of fine scale morphology is needed. The method provides rapid acquisition of signal at selected values in k-space, with multiple successive acquisitions at individual k-values taken on a time scale on the order of microseconds, within a defined tissue volume, and subsequent combination of the multiple measurements in such a way as to maximize SNR. The reduced acquisition volume, and acquisition of only signal values at select places in k-space, along selected directions, enables much higher in vivo resolution than is obtainable with current MRI techniques.

8 Claims, 34 Drawing Sheets

Related U.S. Application Data continuation-in-part of application No. 15/288,974, filed on Oct. 7, 2016, now Pat. No. 9,664,760, which is a continuation-in-part of application No. 15/167,828, filed on May 27, 2016, now Pat. No. 9,664,759, which is a continuation-in-part of application No. 14/840,327, filed on Aug. 31, 2015, now Pat. No. 9,366,738.

(60) Provisional application No. 62/044,321, filed on Sep. 1, 2014, provisional application No. 62/064,206, filed on Oct. 15, 2014, provisional application No. 62/107,465, filed on Jan. 25, 2015, provisional application No. 62/302,577, filed on Mar. 2, 2016, provisional application No. 62/238,121, filed on Oct. 7, 2015, provisional application No. 62/382,695, filed on Sep. 1, 2016.

(51) Int. Cl.
| | | |
|---|---|---|
| *G06T 7/00* | (2017.01) | |
| *A61B 5/055* | (2006.01) | |
| *G01R 33/48* | (2006.01) | |
| *G01R 33/483* | (2006.01) | |
| *G01R 33/563* | (2006.01) | |
| *A61B 5/00* | (2006.01) | |
| *G01R 33/50* | (2006.01) | |

(52) U.S. Cl.
CPC ..... *G01R 33/4818* (2013.01); *G01R 33/4833* (2013.01); *G01R 33/4835* (2013.01); *G01R 33/5602* (2013.01); *G01R 33/5619* (2013.01); *G01R 33/56341* (2013.01); *G06T 7/0012* (2013.01); *A61B 5/7207* (2013.01); *A61B 2560/0238* (2013.01); *G01R 33/50* (2013.01); *G01R 33/5616* (2013.01); *G01R 33/5617* (2013.01); *G06T 2207/10088* (2013.01)

(58) Field of Classification Search
CPC .......... G01R 33/5602; G01R 33/56341; G06T 7/0012; A61B 5/055; A61B 5/7203
See application file for complete search history.

(56) References Cited

U.S. PATENT DOCUMENTS

| | | | | |
|---|---|---|---|---|
| 7,932,720 | B2* | 4/2011 | James | A61B 5/055 |
| | | | | 324/303 |
| 9,097,777 | B2* | 8/2015 | Weber | G01R 33/4833 |
| 9,366,738 | B2* | 6/2016 | Chase | G01R 33/4818 |
| 9,664,759 | B2* | 5/2017 | James | G01R 33/381 |
| 9,664,760 | B2* | 5/2017 | James | G01R 33/4818 |
| 10,061,003 | B2* | 8/2018 | James | A61B 5/055 |
| 10,085,703 | B2* | 10/2018 | Salcudean | A61B 6/50 |
| 2014/0205541 | A1* | 7/2014 | James | A61B 5/055 |
| | | | | 424/9.3 |
| 2014/0303487 | A1* | 10/2014 | James | A61B 5/0042 |
| | | | | 600/415 |
| 2015/0339815 | A1* | 11/2015 | McAuley | G06T 7/0012 |
| | | | | 382/131 |
| 2016/0061917 | A1* | 3/2016 | Chase | G01R 33/4818 |
| | | | | 324/309 |
| 2016/0274203 | A1* | 9/2016 | James | G01R 33/381 |
| 2017/0030986 | A1* | 2/2017 | James | G01R 33/4818 |
| 2017/0261584 | A1* | 9/2017 | James | A61B 5/055 |
| 2018/0313925 | A1* | 11/2018 | Parker | A61B 5/055 |

* cited by examiner

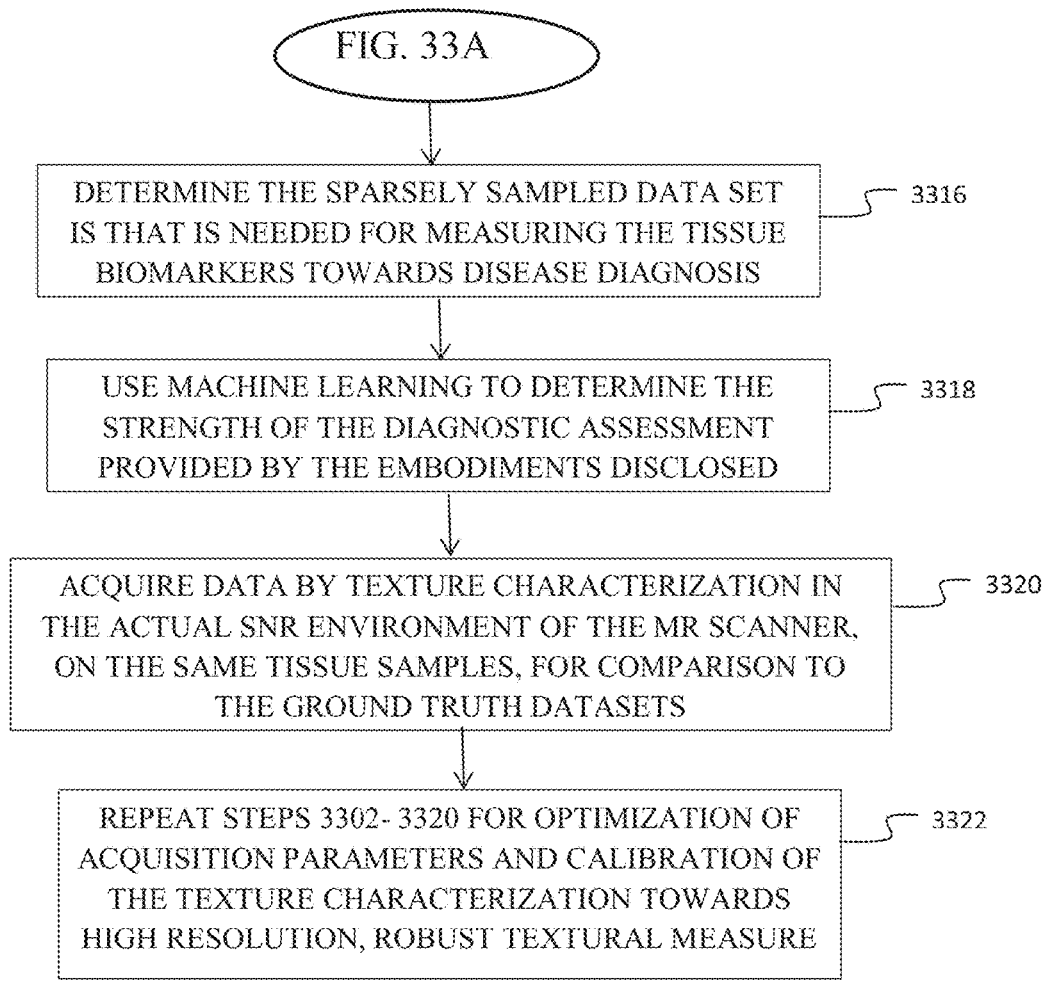

SELECTIVE SAMPLING FOR ASSESSING STRUCTURAL SPATIAL FREQUENCIES WITH SPECIFIC CONTRAST MECHANISMS

REFERENCE TO RELATED APPLICATIONS

This application is a divisional of application Ser. No. 15/604,465 filed on May 24, 2017 which is a continuation in part of application Ser. No. 15/288,974 filed on Oct. 7, 2016, now U.S. Pat. No. 9,664,760, which is a continuation in part of Ser. No. 15/167,828 filed on May 27, 2016, now U.S. Pat. No. 9,664,759, which is a continuation in part of application Ser. No. 14/840,327 filed on Aug. 31, 2015, now U.S. Pat. No. 9,366,738. Application Ser. No. 14/840,327 relies on the priority of U.S. provisional application Ser. No. 62/044,321 filed on Sep. 1, 2014 entitled SELECTIVE SAMPLING MAGNETIC RESONANCE-BASED METHOD FOR ASSESSING STRUCTURAL SPATIAL FREQUENCIES, Ser. No. 62/064,206 filed on Oct. 15, 2014 having the same title and Ser. No. 62/107,465 filed on Jan. 25, 2015 entitled MICRO-TEXTURE CHARACTERIZATION BY MRI, the disclosures of which are incorporate herein by reference. Application Ser. No. 15/167,828 additionally relies on the priority of provisional application Ser. No. 62/302,577 filed on Mar. 2, 2016 entitled METHOD FOR ASSESSING STRUCTURAL SPATIAL FREQUENCIES USING HYBRID SAMPLING WITH LOW OR INCREASED GRADIENT FOR ENHANCEMENT OF VERY LOW NOISE SELECTIVE SAMPLING WITH NO GRADIENT. Application Ser. No. 15/288,974 relies on the priority of U.S. provisional application Ser. No. 62/238,121 filed on Oct. 7, 2015 entitled SELECTIVE SAMPLING MAGNETIC RESONANCE-BASED METHOD FOR ASSESSING STRUCTURAL SPATIAL FREQUENCIES and provisional application Ser. No. 62/382,695 filed on Sep. 1, 2016 entitled SELECTIVE SAMPLING FOR ASSESSING STRUCTURAL SPATIAL FREQUENCIES WITH SPECIFIC CONTRAST MECHANISMS. The referenced applications all have a common assignee with the present application and the disclosures thereof are incorporated herein by reference.

BACKGROUND

Field of the Invention

The herein claimed method relates to the field of diagnostic assessment of fine textures in biological systems for pathology assessment and disease diagnosis, and in material and structural evaluation in industry and in engineering research. More specifically, the embodiments disclosed herein provide methods for repeat measurement of signal at k-values associated with the spatial organization of biologic tissue texture, with the MRI machine gradients turned off and at k-values in an associated neighborhood with a low gradient applied during signal acquisition. Various contrast mechanisms can be used in conjunction with the embodiments disclosed herein; in cases of novel contrast mechanisms, such as DWI, DTI, or ASL, which, in addition to changing timing, may require additional tailored RF and gradient pulses, the novel contrast can be incorporated into the embodiment, forming an integrated sequence; another method would be one wherein data acquisition by the novel contrast sequence is run in parallel with data acquisition by the disclosed embodiments and the data compared, with the data obtained by the embodiments disclosed providing direct measure of the fine tissue texture for calibrating and understanding the data obtained by another contrast method. That is, the use of varying contrast methods allows use of the embodiments in conjunction with other MRI imaging and measurement methods either in an integrated form, wherein the timing and any additional RF and gradient pulses used to set contrast are combined into one pulse sequence, or in parallel operation wherein data acquired using the disclosed embodiments is acquired and compared as a calibration/complimentary assessment of the data acquired by other contrast mechanisms. The data obtained either by the integrated method or the complementary method can further be mapped across a region of tissue to assess the spatial variation in pathology. The methods enable in vivo assessment, towards diagnosis and monitoring of disease and therapy-induced textural changes in tissue. Representative targets of the technique are: 1) for assessment of changes to trabecular architecture caused by bone disease, allowing assessment of bone health and fracture risk; 2) evaluation of fibrotic development in soft tissue diseases such as, for example, liver, lung, and heart disease; 3) changes to fine structures in neurologic diseases, such as, for example, the various forms of dementia, Multiple Sclerosis (MS), or in cases of brain injury and downstream neuropathology as in, for example, Traumatic Brain Injury (TBI) and Chronic Traumatic Encephalopathy (CTE), or for characterization and monitoring of abnormal neurologic conditions such as autism and schizophrenia; 4) assessment of vascular changes such as in the vessel network surrounding tumors or associated with development of CVD (Cerebrovascular Disease), and of changes in mammary ducting in response to tumor growth; 5) assessment of fibrotic diseases, from lung and liver fibrosis, to cardiac and cystic fibrosis, pancreatic fibrosis, muscular dystrophy, bladder and heart diseases, and myelofibrosis, in which fibrotic structures replace bone marrow, cancers, such as breast cancer and prostate cancer, muscle diseases, such as Central Core Disease, in which the lobular formations in muscle become infiltrated with fibrotic development; 6) lung disease diagnosis such as Idiopathic Pulmonary Fibrosis (IPF). The invention also has applications in assessment of fine structures for a range of industrial purposes such as measurement of material properties in manufacturing or in geology to characterize various types of rock, as well as other uses for which measurement of fine structures/textures is needed.

Description of the Related Art

Though fine textural changes in tissue have long been recognized as the earliest markers in a wide range of diseases, robust clinical assessment of fine texture remains elusive, the main difficulty arising from blurring caused by subject motion over the time required for data acquisition.

Early and accurate diagnosis is key to successful disease management. Though clinical imaging provides much information on pathology, many of the tissue changes that occur as a result of disease onset and progression, or as a result of therapy, are on an extremely fine scale, often down to tens of microns. Changes in fine tissue texture have been recognized for many years by diagnosticians, including radiologists and pathologists as the earliest harbinger of a large range of diseases, but in vivo assessment and measurement of fine texture has remained outside the capabilities of current imaging technologies. For instance, differential diagnosis of obstructive lung disease relies on a textural presentation in the lung parenchyma, but the robustness of the Computed Tomography (CT) measure of early stage disease is limited. Trabecular bone microarchitecture, the determinant of fracture risk in aging bone, has also remained elusive due to image blurring from patient motion during Magnetic Resonance (MR) imaging scans. Post processing analysis of MR-images is sometimes used to try to differentiate image textures in structures such as tumors and white matter. (DRABYCZ, S., et al.; "Image texture characterization using the discrete orthogonal S-transform"; Journal of Digital Imaging, Vol. 22, No 6, 2009. KHIDER, M., et al.; "Classification of trabecular bone texture from MRI and CT scan images by multi-resolution analysis"; 29th Annual International Conference of the IEEE Engineering in Medicine and Biology Society, EMBS 2007.) But post processing analysis is limited in effect as it doesn't deal with the underlying problem that prevents high resolution acquisition of textural information, i.e. subject motion. (MACLAREN, J. et al.; "Measurement and correction of microscopic head motion during magnetic resonance imaging of the brain", PLOS/ONE, Nov. 7, 2012. MACLARAN, J. et al.; "Prospective motion correction in brain imaging: a review; Magnetic Resonance in Medicine, Vol. 69, 2013.)

The main sources of motion affecting MR imaging are cardiac pulsatile motion, respiratory-induced motion and twitching. The first two are quasi-cyclic, the usual approach to which is gating at the slowest phase of motion. However, even with gating, there is sufficient motion between acquisitions to cause loss of spatial phase coherence at the high k-values of interest for texture measurements. This problem is exacerbated by the fact that motion may not be perfectly cyclic, and often originates from combined sources. Twitching is rapid, inducing random displacements, and hence it is not possible to maintain coherence at the high k-values of interest when measuring texture.

While Positron Emission Tomography (PET) provides valuable diagnostic information, it is not capable of resolution below about 5 mm and relies on the use of radioactive tracers for imaging as well as x-ray beams for positioning, raising dose concerns, especially if repeat scanning is needed. (BERRINGTON DE GONZALEZ, A. et al.; "Projected cancer risks from Computed Tomographic scans performed in the United States in 2007"; JAMA Internal Medicine, Vol. 169, No. 22, December 2009.) Further, PET imaging is extremely costly, requiring a nearby cyclotron. CT resolution down to 0.7 mm is possible in theory, though this is obtained at high radiation dose and is subject to reduction by patient motion over the few minute scan time. The non-negligible risk from the associated radiation dose makes CT problematic for longitudinal imaging and limits available resolution. Along with serious dose concerns, digital x-ray resolution is limited because the 2-dimensional image obtained is a composite of the absorption through the entire thickness of tissue presented to the beam. Current clinical diagnostics for the diseases that are the target of the embodiments disclosed herein are fraught with difficulties in obtaining sufficient in vivo resolution, or accuracy. In some cases, no definitive diagnostic exists currently. In other pathologies, particularly in breast and liver, diagnosis is dependent on biopsy, with its non-negligible risk of morbidity and even mortality, and which is prone to high read and sampling errors. (WELLER, C; "Cancer detection with MRI as effective as PET-CT scan but with zero radiation risks"; Medical Daily, Feb. 18, 2014.)

Bone health is compromised by ageing, by bone cancer, as a side effect of cancer treatments, diabetes, rheumatoid arthritis, and as a result of inadequate nutrition, among other causes. Bone disease affects over ten million people annually in the US alone, adversely affecting their quality of life and reducing life expectancy. For assessment of bone health, the current diagnostic standard is Bone Mineral Density (BMD), as measured by the Dual Energy X-ray Absorptiometry (DEXA) projection technique. This modality yields an areal bone density integrating the attenuation from both cortical and trabecular bone, similar to the imaging mechanism of standard x-ray, but provides only limited information on trabecular architecture within the bone, which is the marker linked most closely to bone strength. (KANIS, J. AND GLUER, C.; "An update on the diagnosis and assessment of osteoporosis with densitometry"; Osteoporosis International, Vol. 11, issue 3, 2000. LEGRAND, E. et al.; "Trabecular bone microarchitecture, bone mineral density, and vertebral fractures in male osteoporosis"; JBMR, Vol. 15, issue 1, 2000.) BMD correlates only loosely with fracture risk. A post-processing technique, TBS (Trabecular Bone Score) attempts to correlate the pixel gray-level variations in the DEXA image, to yield information on bone microarchitecture. A comparison study determined that BMD at hip remains a better predictor of fracture. But, though TBS does not yield a detailed assessment of trabecular architecture. (BOUSSON, V., et al.; "Trabecular Bone Score (TBS): available knowledge, clinical relevance, and future prospects"; Osteoporosis International, Vol. 23, 2012. DEL RIO, et al.; "Is bone microarchitecture status of the spine assessed by TBS related to femoral neck fracture? A Spanish case-control study": Osteoporosis International, Vol. 24, 2013.) TBS is a relatively new technique and is still being evaluated.

Measurement of bone microarchitecture, specifically trabecular spacing and trabecular element thickness, requires resolution on the order of tenths of a millimeter. MRI, ultrasound imaging, CT, and microCT have all been applied to this problem. In MRI, though high contrast between bone and marrow is readily obtained, resolution is limited by patient motion over the long time needed to acquire an image with sufficient resolution to characterize the trabecular network. The finer the texture size of this network, the greater the blurring from motion. An attempt to mitigate the effects of patient motion by looking only at the skeletal extremities, removed from the source of cardiac and respiratory motion sources, has been tried using both MRI and microCT. However, the correlation between bone microarchitecture in the extremities and that in central sites in not known. Further, a large data matrix, hence long acquisition time, is still required to obtain sufficient image information to determine trabecular spacing and element thickness. This long acquisition time results in varying levels of motion-induced blurring, depending on patient compliance—twitching is still a serious problem even when measuring extremities. A proposed MR-based technique, fineSA (JAMES, T., CHASE, D.; "Magnetic field gradient structure characteristic assessment using one dimensional (1D) spatial-frequency distribution analysis"; U.S. Pat. No. 7,932,7207; Apr. 26, 2011.), attempts to circumvent the problem of patient motion by acquiring a much smaller data matrix of successive, finely-sampled, one-dimensional, frequency-encoded acquisitions which are subsequently combined to reduce noise. Imaging in this case is reduced to one dimension, reducing the size of the data matrix acquired and, hence, the acquisition time. However, as the gradient encoded echoes, are very low Signal to Noise (SNR), noise averaging is required. Though some resolution advantage is gained by this method relative to 2 and 3-d imaging, the need to acquire many repeat spatially-encoded echoes over several response times (TRs) for signal averaging results in an acquisition time on the order of minutes—too long to provide motion immunity. Thus, resolution improvement obtainable by the technique is limited.

What is needed is an accurate, robust, non-invasive, in vivo measure of trabecular spacing and trabecular element thickness capable of assessing bones in the central skeleton, as these are the key markers for assessing bone health and predicting fracture risk. Until now, no clinical technique has been able to provide this capability.

Fibrotic diseases occur in response to a wide range of biological insults and injury in internal organs, the development of collagen fibers being the body's healing response. The more advanced a fibrotic disease, the higher the density of fibers in the diseased organ. Fibrotic pathology occurs in a large number of diseases, from lung and liver fibrosis, to cardiac and cystic fibrosis, pancreatic fibrosis, muscular dystrophy, bladder and heart diseases, and myelofibrosis, in which fibrotic structures replace bone marrow. Fibrotic development is attendant in several cancers, such as breast cancer. A different pathology development is seen in prostate cancer, where the disease destroys healthy organized fibrous tissue. In all cases, textural spacings highlighted in the tissue change in response to disease progression, as collagen fibers form along underlying tissue structures. In liver disease, the textural wavelength changes as the healthy tissue texture in the liver is replaced by a longer wavelength texture originating from the collagen "decoration" of the lobular structure in the organ. In other organs/diseases, textural change reflects the upset in healthy tissue with development of texture indicative of fibrotic intervention.

To span the range of disease progression in most fibrotic pathologies, evaluation of textural changes from fibrotic development requires resolution on the scale of tenths of a mm One of the most prevalent of such pathologies, liver disease, is representative of the difficulty of assessing fibrotic structure. Currently, the gold standard for pathology assessment is tissue biopsy—a highly invasive and often painful procedure with a non-negligible morbidity—and mortality—risk (patients need to stay at the hospital for post-biopsy observation for hours to overnight), and one that is prone to sampling errors and large reading variation. (REGEV, A.; "Sampling error and intraobserver variation in liver biopsy in patients with chronic HCV infection"; American Journal of Gastroenterology; 97, 2002. BEDOSSA, P. et al.; "Sampling variability of liver fibrosis in chronic hepatitis C"; Hepatology, Vol. 38, issue 6, 2004. VAN THIEL, D. et al.; "Liver biopsy: Its safety and complications as seen at a liver transplant center"; Transplantation, May 1993.) Ultrasound, another modality often used to assess tissue damage in liver disease, is only able to provide adequate assessment in the later stages of the disease—it is used to diagnose cirrhosis. Magnetic Resonance-based Elastography (MRE), which has been under development for some time for use in assessment of liver disease, is not capable of early-stage assessment—the read errors are too large prior to significant fibrotic invasion (advanced disease). Further, this technique requires expensive additional hardware, the presence of a skilled technician, and takes as much as 20 minutes total set up and scanning time, making it a very costly procedure. The ability to image fibrotic texture directly by MR imaging is compromised both by patient motion over the time necessary to acquire data and by lack of contrast between the fibers and the surrounding tissue. Even acquisition during a single breath hold is severely compromised by cardiac pulsatile motion and noncompliance to breath hold, which results in significant motion at many organs, such as liver and lungs. And SNR is low enough that motion correction by combining reregistered MR-intensity profiles obtained from successive echoes is extremely problematic. Similarly, assessment of the amount of cardiac fibrosis in early stage disease using MRI is seriously hampered by cardiac pulsation over the time of the measurement. As motion is, unlike Gaussian noise, a non-linear effect, it can't be averaged out—there must be sufficient signal level to allow reregistration before averaging for electronic noise-reduction. A more sensitive (higher SNR), non-invasive technique, capable of assessing textural changes throughout the range of fibrotic development, from onset to advanced pathology, is needed to enable diagnosis and monitoring of therapy response.

Onset and progression of a large number of neurologic diseases are associated with changes in repetitive fine neuronal and vascular structures/textures. However, ability to assess such changes in the brain is only available post mortem. Currently, definitive diagnosis of Alzheimer's Disease (AD) is by post mortem histology of brain tissue. AD and other forms of dementia such as Dementia with Lewy Bodies, motor diseases such as Amyotrophic Lateral Sclerosis (ALS), Parkinson's disease, conditions precipitated by Traumatic Brain Injury (TBI) such as Chronic Traumatic Encephalopathy (CTE), as well as those caused by other pathologies or trauma, or conditions that involve damage to brain structures such as Multiple Sclerosis (MS), Cerebrovascular Disease (CVD), and other neurologic diseases, are often only diagnosable in advanced stages by behavioral and memory changes, precluding the ability for early stage intervention. Further, conditions such as epilepsy and autism have been associated with abnormal variations in fine neuronal structures, which, if clinically diagnosable, would allow targeted selection for testing therapy response.

Various in vivo diagnostic techniques are available for AD and other dementias, but none of them are definitive. These techniques range from written diagnostic tests, which are prone to large assessment errors, to PET imaging to assess amyloid plaque density or glucose metabolism (FDG PET). As discussed previously, PET imaging is extremely expensive, cannot provide high resolution, and relies on use of radioisotopes and positioning x-ray beams, complicating approval for longitudinal use due to dose concerns. Further, neither amyloid imaging nor FDG PET has been shown to provide a definitive indication of AD. (MOGHBEL, M. et al. "Amyloid Beta imaging with PET in Alzheimer's disease: is it feasible with current radiotracers and technologies?"; Eur. J. Nucl. Med. Mol. Imaging.)

Use of CSF biomarkers for dementia diagnosis is painful and highly invasive and cannot differentiate signal levels by anatomic position in the brain, as is possible with imaging biomarkers. As various forms of dementia are found to have different spatial/temporal progression through the brain, this is a serious drawback to use of liquid biopsy. Another disease associated with various forms of dementia is CVD (Cerebrovascular Disease), which induces cognitive impairment as a result of reduced blood flow through blocked vessels leading to brain tissue. Something capable of high-resolution assessment of pathology-induced changes in micro-vessels is needed here.

Tissue shrinkage due to atrophy in many forms of dementia including AD is measurable with careful registration of longitudinally-acquired data in MRI, but the disease is advanced by the time this shrinkage is measurable. Early stages of disease are indicated in post mortem histology by degradation in the columnar ordering of cortical neurons, the normal spacing for these columns being on the order of 100 microns in most cortical regions. (CHANCE, S. et al.;

"Microanatomical correlates of cognitive ability and decline: normal ageing, MCI, and Alzheimer's disease"; Cerebral Cortex, August 2011. E. DI ROSA et al.; "Axon bundle spacing in the anterior cingulate cortex of the human brain"; Journal of Clinical Neuroscience, 15, 2008.) This textural size, and the fact that the cortex is extremely thin, makes speed of acquisition paramount, as even tiny patient motion will make data collection impossible. Assessment of textural changes on the order of tens of microns is extremely problematic in vivo, but would, if possible, enable targeting a range of fine textural changes in neuronal disease diagnosis and monitoring, and would play an important role in therapy development.

Another possible neurologic application for the claimed method is to, in vivo, determine the boundaries of the various control regions of the cerebral cortex or the different Brodmann's areas of which these are comprised. Such ability would greatly aid data interpretation in brain function studies, such as those performed using, for example, FMRI (Functional Magnetic Resonance Imaging).

The three classes of diseases listed above, bone disease, fibrotic diseases, and neurologic diseases are not an all-inclusive list. Other disease states in which pathology-induced changes of fine structures occur, for instance angiogenic growth of vasculature surrounding a tumor, or fibrotic development and changes in vasculature and mammary gland ducting in response to breast tumor development, also are pathologies wherein the ability to resolve fine tissue textures would enable early detection of disease, and monitoring of response to therapy.

The ability to measure changes in fine textures would be of great value for disease diagnosis. Non-invasive techniques that do not rely on use of ionizing radiation or radioactive tracers allow the most leeway for early diagnosis and repeat measurement to monitor disease progression and response to therapy. Magnetic Resonance Imaging (MRI), which provides tunable tissue contrast, is just such a non-invasive technique, with no radiation dose concerns. However, in order to circumvent the problem of signal degradation due to patient motion, data must be taken on a time scale not previously possible.

SUMMARY OF THE INVENTION

The embodiments disclosed herein provide a method for pathology assessment employing tissue texture using magnetic resonance (MR) which may be used integrally with an MR imaging technique. A contrast mechanism is selected for enhancing the contrast between component tissue types in a multiphase biologic sample for measurement with a MR imaging process. The selected contrast mechanism is then applied and a volume of interest (VOI) is selectively excited employing a plurality of time varying radio frequency signals and applied gradients. An encoding gradient pulse is applied to induce phase wrap to create a spatial encode for a specific k-value and orientation, the specific k-value determined based on texture within the VOI. A series of gradients is initiated to produce k-value encodes, a resulting k-value set being a subset of that required to produce an image of the VOI. Multiple sequential samples of the NMR RF signal encoded with the k-value set are recorded. Post processing the recorded NMR signal samples is accomplished to produce a data set of signal vs k-values for k-values in the k-value set, to characterize textural features of tissue in the VOI. The MR imaging process is then performed as an integral or hybrid pulse sequence with the texture measurement.

BRIEF DESCRIPTION OF THE DRAWINGS

The features and advantages of embodiments disclosed herein will be better understood by reference to the following detailed description when considered in connection with the accompanying drawings wherein.

DETAILED DESCRIPTION OF THE INVENTION

Figure 1:
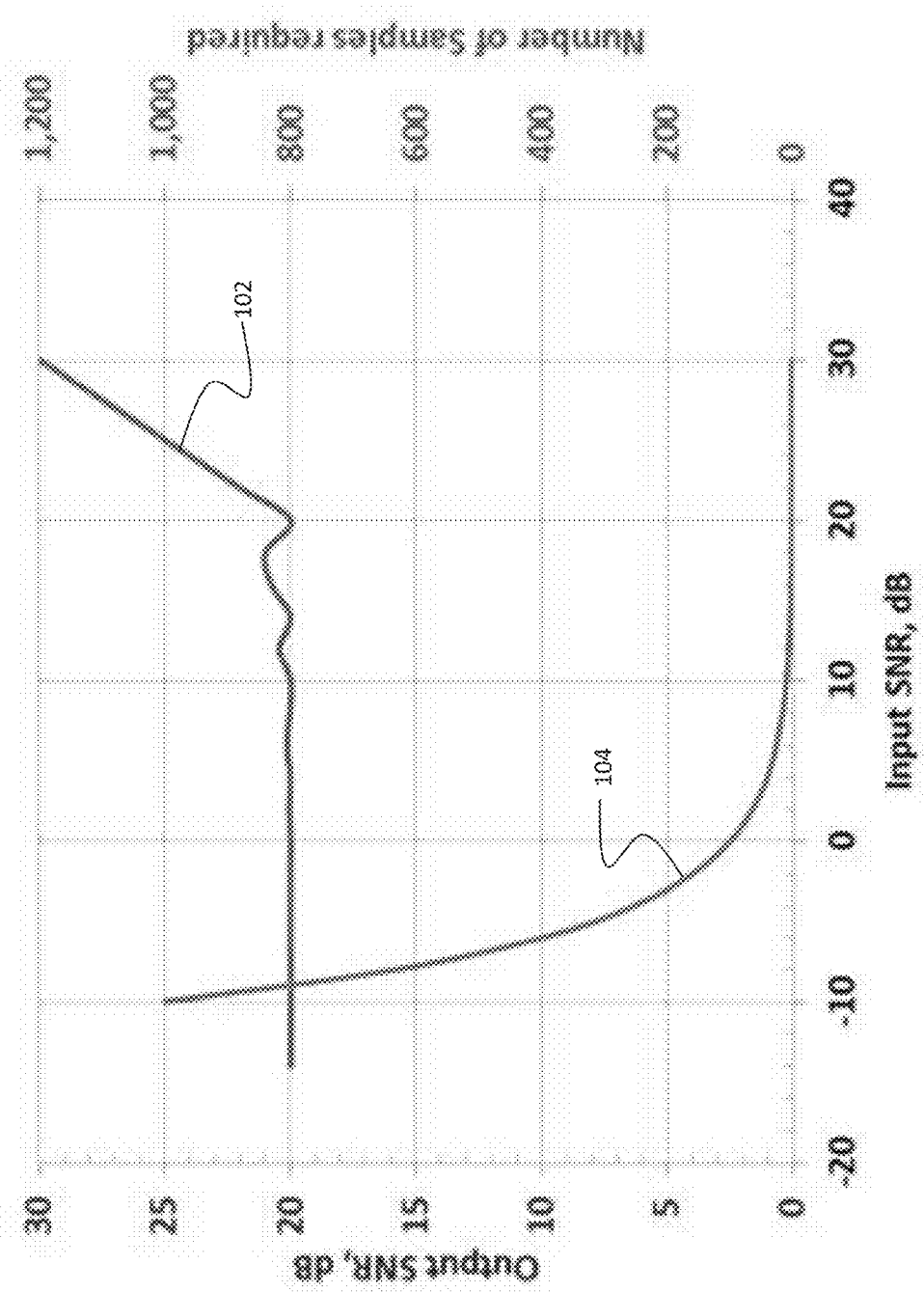
FIG. 1 is a simulation showing the number of data samples required for averaging to achieve an output SNR≥20 dB as a function of input SNR.

The following definition of terms as used herein is provided:

180° inversion pulse RF pulse that inverts the spins in a tissue region to allow refocusing of the MR signal.

180° pulse An RF pulse that tips the net magnetic field vector antiparallel to $B_0$ 90° pulse An RF pulse that tips the net magnetic field vector into the transverse plane relative to $B_0$ 3 T 3 Tesla A/D Analog to digital converter AD Alzheimer's Disease ADC Average diffusion coefficient measured in Diffusion Weighted Imaging Adiabatic pulse excitation Adiabatic pulses are a class of amplitude- and frequency-modulated RF-pulses that are relatively insensitive to 6 inhomogeneity and frequency offset effects.

ASL Arterial Spin Labelling

AWGN Additive White Gaussian Noise Additive white Gaussian noise (AWGN) is a basic noise model used in Information theory to mimic the effect of many random processes that occur in nature.

BPH Benign Prostatic Hyperplasia

Biopsy A biopsy is a sample of tissue extracted from the body in order to examine it more closely.

BOLD Blood Oxygenation Level Dependent

C/N Contrast to Noise, a measure of image quality based on signal differences between structural elements rather than on overall signal level CAWGN Complex-valued, additive white Gaussian noise CBF Cerebral Blood Flow Chemical shift Small variations in MR resonant frequency due to the different molecular environments of the nuclei contributing to an MR signal.

CJD Creutzfeld-Jakob Disease

Crusher gradients Gradients applied on either side of a 180° RF refocussing slice selection pulse to reduce spurious signals generated by imperfections in the pulse.

CSF Cerebrospinal fluid

CVD Cerebrovascular disease

DCE Dynamic Contrast Enhanced

DEXA Dual Energy X-ray Absorptiometry is a means of measuring bone mineral density using two different energy x-ray beams.

DSC Dynamic susceptibility contrast

DTI Diffusion Tensor Imaging

DWI Diffusion Weighted Imaging

Echo The RF pulse sequence where a 90° excitation pulse is followed by a 180° refocusing pulse to eliminate field inhomogeneity and chemical shift effects at the echo.

Frequency encodes Frequency-encoding of spatial position in MRI is accomplished through the use of supplemental magnetic fields induced by the machine gradient coils Gaussian noise Gaussian noise is statistical noise having a probability density function (PDF) equal to that of the normal distribution, which is also known as the Gaussian distribution.

Gradient pulse a pulsing of the machine magnetic field gradients to alter the k-value encode Gradient set the set of coils around the bore of an MR scanner used primarily to spatially encode signal or to set a particular phase wrap in a selected direction GRE Gradient Recalled Echo Interleaved acquisition Signal acquisition from a multiplicity of VOIs, successively excited within a single TR Isochromat A microscopic group of spins that resonate at the same frequency.

k-space The 2D or 3D Fourier transform of the MR image.

k-value coefficient The coefficient in a Fourier series or transform reflecting the relative weight of each specific k-value in the series.

k-space The 2D or 3D Fourier transform of the MR image.

k-value One of the points in k-space reflecting the spacing of structural elements in a texture field.

k-value selection pulse The gradient pulse used to select a specific k-value encode along the sampled direction Library of k-space values the net collection of k-space coefficients acquired in a particular region of tissue for tissue characterization Machine gradients the magnetic field gradients imposable through use of the set of gradient coils in an MR scanner MRE Magnetic Resonance Elastography—an imaging technique that measures the stiffness of soft tissues using acoustic shear waves and imaging their propagation using MRI.

MRI Magnetic Resonance Imaging

MRS Magnetic Resonance Spectroscopy

MS Multiple Sclerosis

MTI Magnetization Transfer Imaging

Noise floor In signal theory, the noise floor is the measure of the signal created from the sum of all the noise sources and unwanted signals within a measurement system NMR Nuclear Magnetic Resonance PET Positron Emission Tomography is a functional imaging technique that produces a three-dimensional image of functional processes in the body using a positron-emitting radiotracer.

Phase coherence (spatial) When referring to multiple measurements within a common VOI of a or multiple k-values indicates that the sample has the same position relative to the measurement frame of reference Phase encode A phase encode is used to impart a specific phase angle to a transverse magnetization vector. The specific phase angle depends on the location of the transverse magnetization vector within the phase encoding gradient, the magnitude of the gradient, and the duration of the gradient application.

Phase wrap The helical precession of the phase of the transverse magnetization along a phase encoded sample Pitch with reference to the pitch of a screw, the tightness of the phase wrap along the direction of k-value encode Profile A one dimensional plot of signal intensity RF Radio Frequency electromagnetic signal Semi-crystalline texture a texture exhibiting regular spacing along one or more directions slice (slab) Used interchangeably to indicate a non-zero thickness planar section of the Slice-selective refocusing Refocussing of spins through combination of a slice selective gradient and an RF pulse such that the bandwidth of the RF pulse selects a thickness along the direction of the gradient, and the RF pulse tips the net magnetization vector away from its equilibrium position Only those spins processing at the same frequency as the RF pulse will be affected.

SE Spin Echo

SNR Signal to Noise Ratio

Spoiler gradients see crusher gradients

T2 Defined as a time constant for the decay of transverse magnetization arising from natural interactions at the atomic or molecular levels.

T2* In any real NMR experiment, the transverse magnetization decays much faster than would be predicted by natural atomic and molecular mechanisms; this rate is denoted T2* ("T2-star"). T2* can be considered an "observed" or "effective" T2, whereas the first T2 can be considered the "natural" or "true" T2 of the tissue being imaged. T2* is always less than or equal to T2.

TBS Trabecular Bone Score is a technique that looks for texture patterns in the DEXA signal for correlation with bone microarchitecture for assessing bone health TbTh trabecular thickness for bone measurement.

TbSp trabecular spacing for bone measurement.

TbN trabecular number for bone measurement.

TE Spin Echo sequences have two parameters: Echo Time (TE) is the time between the 90° RF pulse and MR signal sampling, corresponding to maximum of echo. The 180° RF pulse is applied at time TE/2. Repetition Time is the time between 2 excitations pulses (time between two 90° RF pulses).

Textural frequency the number of texture wavelength repeats per unit length in a texture Texture wavelength the characteristic spacing between structural elements in a texture TR Spin Echo sequences have two parameters: Echo Time (TE) is the time between the 90° RF pulse and MR signal sampling, corresponding to maximum of echo. The 180° RF pulse is applied at time TE/2. Repetition Time is the time between 2 excitations pulses (time between two 90° RF pulses).

Vector combination gradient A magnetic gradient resulting from any vector combination of the gradient coil set VOI Volume of Interest Windowing function In signal processing, a window function (also known as an apodization function or tapering function) is a mathematical function that is zero-valued outside of some chosen interval x-ray diffraction X-ray diffraction is a tool used for identifying the atomic and molecular structure of a crystal The embodiments disclosed herein provide an MR-based technique that enables in vivo, non-invasive, high-resolution measurement and assessment of fine biologic textures, enabling monitoring of texture formation and/or change in response to disease onset and progression in a range of pathologies. This same method can be applied to fine-texture characterization in other biologic and physical systems. It enables MR-based resolution of fine textures to a size scale previously unattainable in in vivo imaging.

In standard MR "imaging" the morphology of a large region of anatomy or an organ is imaged by using a pulse sequence that induces contrast from one tissue type/organ to the next. To obtain an image, signal must be averaged over individual voxels, the size of the voxels then setting the image resolution.

This imaging will be sensitive to tissue contrast near lesions, such as tumors, etc. that appear then at localized points of an organ in the image. Or, the image might show that an organ has changed, perhaps become enlarged, relative to a healthy organ. As such, the basic image is the anatomy and any localized pathology shows up on this anatomical image.

To acquire a 3D image, data acquisition can be by acquisition of multiple, spatially adjoining, slices, or as a 3D dataset directly. In effect, a 2D slice is a "map" of signal level, the individual pixels of the map being the individual voxels. The signal level of each voxel depends on the contrast mechanism applied. The relative signal levels of each voxel then form the image. Though, in effect, this is a map of voxel brightness, when the intent is to depict morphologic variation directly across a region of the anatomy, it is called an image.

Alternatively, mapping is the creation of a display of an indirect quantity that affects the brightness of an MR signal. It is not a map of morphology, but of an inferred tissue characteristic, such as Apparent Diffusion Coefficient, or Fractional Anisotropy, or organ stiffness. As such, the brightness in the voxels that make up the mapped quantity also form an "image" but in common usage this would be called a map. Often such a map is compared to an image from the same anatomical region. This would allow, for instance, a tumor region that shows up bright on, say, the brain in an image, to be compared to the diffusion coefficient in that region.

The terms imaging and mapping may be used interchangeably in the description herein and refer to a resulting dataset for display or manipulation not necessarily an attempted reproduction of a "picture" image of the morphology.

The method, while described herein with respect to biological systems for examination of tissue, is equally applicable for assessment of fine structures in a range of industrial purposes such as measurement of material properties in manufacturing or in geology to characterize various types of rock, as well as other uses for which measurement of fine structures/textures is needed.

The embodiments disclosed herein achieve this significant improvement in in vivo resolution of fine texture by acquiring the requisite data fast enough that the effect of subject motion, the factor that limits MRI resolution, becomes negligible. This fast acquisition is achieved by acquiring data incrementally—at a single location, orientation and at one, or a select set or range, of k-values at a time—within one TR, if multiple pulses are used, or within one excitation pulse. After applying an encoding gradient to select the k-value of interest, data is acquired with the gradient switched off, allowing multiple acquisition repeats of the signal at the encoded k-value for subsequent averaging to reduce electronic noise, thus enabling robust measure at individual k-values before motion blurring can occur. To build up measurements on a larger set of selected k-values present within the tissue, or towards development of a continuous spectrum of textural spacings within the tissue, the acquisition TR can be repeated as many times as necessary, changing the encode as needed to span the desired extent of real and of k-space required. The set of signals measured at one or more k-values output from each TR are now high SNR due to the ability to average repeats without motion effects, and since the measure of interest is textural spacing, and not development of an image, the lack of phase coherence between TRs is of no concern.

In its simplest form the embodiments disclosed herein consist of acquiring MR signal from within an inner volume to encompass a specific tissue region of interest, such as a lesion, an organ, a location in an organ, a specific region of bone, or a number of regions in a diseased organ for sampling. This inner volume may be excited by one of a number of methods, including but not limited to: intersecting slice-selective refocusing, selective excitation using phased-array transmit in combination with appropriate gradients, adiabatic pulse excitation to scramble signal from the tissue outside the region of interest, outer volume suppression sequences, and other methods of selectively exciting spins in an internal volume including physically isolating the tissue of interest, to name a few.

After definition of a volume of interest (VOI), in certain embodiments, the gradient is turned off, and multiple samples of signal centered at a specific k-value, the spread of which is defined by receiver BW and sampling length, are acquired. This measurement is repeated only at a set of k-values and in specified directions within the VOI, rather than trying to map all of k-space as is required to generate an image. One or more samples of signal at a particular k-value are acquired within an acquisition block during a single TR, or excitation pulse, and the k-value subsequently incremented or decremented, allowing further samples at other k-values as desired during the same TR, or excitation pulse. This method allows multiple sampling at each k-value of interest over a time period of milliseconds, providing immunity to subject motion. The process can then be repeated in further TRs, the requirement on motion between signal acquisitions at specific k-values being only that the VOI remain within the tissue region of interest. Buildup of a magnitude spectrum of textural frequencies may be accomplished without the need to acquire it in a spatially coherent manner Because the quantities of interest are the relative intensities of the various k-values (textural spacings) present in the sample volume, as long as the acquisition volume remains within a representative sample of tissue, any motion between the blocks does not compromise the measurement. In the case of motion of sufficiently large magnitude that an internally excited volume might be formed in other tissue volumes over the course of building up a spectrum of k-values contained in the tissue, use of fairly robust, real-time piloting and acquisition algorithms can be used for gross repositioning of the internal selectively excited volume and for rejecting data sets that have failed to stay in the proper tissue.

Repositioning the VOI to allow sampling of texture at multiple positions within or across an organ or anatomy allows determination of the variation in pathology through the organ. The data acquired can, with reference to positioning images, be mapped spatially. Either the VOI can be moved in successive TRs or interleaved acquisition done within a single TR by exciting additional volumes during the time that the signal is recovering in advance of the next TR. The requirement is that successive VOIs be excited in new tissue, that does not overlap the previous slice selects. Spatial variation of pathology can be determined by this method. This can also be used to monitor temporal progression of a pathology through an organ if the measure is repeated longitudinally.

Tailoring the pulse sequence to pre-wind phase in the sample volume can position the measure of signal at the highest k-values of interest at the echo peak where the signal is strongest, providing best SNR measurement.

Sampling of signal at k-values, with the acquisition axis oriented along varying directions, aligned at varying angles and along varying paths, either rectilinear or curved, within the volume(s) under study can yield important information on texture, especially textures with semi-ordered structure in specific directions, such as neuronal minicolumns. Measurement of signal vs. k-values associated with columnar spacing is extremely sensitive to alignment of the sampling path, as slight variations in sampling direction on either side of perpendicular show a rapid drop off in signal for that k-value. Rocking the acquisition path on either side of the signal maximum can yield a measure of pathology-induced randomness which is indicated by the width of the signal vs. k-value peak.

With the gradient switched off for data acquisition, tuning the bandwidth to particular chemical species can enhance structural information when the chemical composition of the structure under study is known.

The embodiments disclosed herein can be used in conjunction with time-dependent contrast schemes that target blood flow. Some of these contrast techniques are Blood Oxygenation Level Dependent (BOLD) imaging, Arterial Spin Labeling (ASL) imaging, and Dynamic Susceptibility Contrast (DSC) imaging. As these methods use various techniques to highlight vasculature, changes in the texture of the vasculature associated with many pathologies, including CVD (cerebrovascular disease) and tumor growth can be measured.

The embodiments disclosed herein can also be used in conjunction with various novel MR-contrast mechanisms, including DWI, DTI and MTI, to provide front end information toward parameter selection for the diffusion techniques as well as correlation with their measurements of tissue health.

The rapid repeat measurement of signal at a single k-value, with the total time to acquire a block being on the order of a msec, reduces patient and machine motion-induced blurring to a negligible level, enabling robust assessment of fine textures previously not accessible in vivo. (For comparison, standard MR image acquisition times are much longer in duration over which patients are asked to remain completely stationary.) Since the excited tissue defining the VOI moves with any tissue motion, acquisition within one TR, or excitation pulse, is largely immune to subject motion. The SNR of signal measured at each k-value selected is significantly improved through combination of the individual samples at each k-value within a block; this averaging can be done without concern for subject motion, which is eliminated due to the rapid sequential acquisition of the individual samples in the block.

This significant improvement in SNR is made possible because the embodiments disclosed herein focus on acquiring signal at only the k-values of interest for determination of fine texture pathology signatures, rather than on acquisition of the large number of spatially-encoded echoes required for image formation. The significantly reduced data matrix enables the increased number of coherent repeats at the targeted k-values, and hence significant improvement in SNR.

Energy density within a range of textural spacings is proportional to textural wavelength, or inversely to k-value—i.e. the higher the k-value, the lower the associated signal intensity. The fast acquisition enabled through use of the embodiments disclosed herein, enables tailoring the number of acquisition repetitions at a particular k-value to acquire k-values for which there is low signal first, before $T_2$ and $T_2^*$ effects have degraded signal amplitude. In this way, the SNR of each repeat to be averaged for noise cancellation (or spatial-phase-corrected before combining it with the measurements of k-value from subsequent TRs) will be above this threshold. It does not matter that there is motion between acquisition cycles at different k-values as long as each acquisition lies within the tissue volume of interest (VOI). As the claimed method targets only assessment of pathology-induced changes in tissue texture, there is no requirement for phase coherence over an entire cycle of data acquisition, as is required in imaging.

Several benefits result from acquiring data after the gradient is switched off for single-k-value sampling in a reduced volume (the VOI). By proper pulse sequencing, the echo record window can be designed such that recording begins with the highest k-values of interest, as signal level is highest at the echo peak. This enables recording of fine structures currently unachievable with in vivo MR imaging.

Additionally, T2* is longer with the gradient off, so SNR is improved by the longer acquisition times possible. This allows acquisition of an increased number of samples, N.

Coil combination is also simplified by having higher SNR for each k-value, hence providing a significant improvement in overall SNR. This is especially beneficial as the trend in MRI is towards coil arrays composed of many small element coils. As the acquisition volumes targeted in the embodiments disclosed herein are small, correction for phase across the sample volume is not needed. Only one phase and gain value for each coil is needed for combining the multiple element channels. These can be combined using the Maximal Ratio Combining (MRC) method, which weights the coil with the highest SNR most heavily, or other multi-signal combination methods. (Phase and gain for the elements of a given coil array can be determined once from a phantom and applied to patient data.)

Signal acquisition and data sampling in a standard MRI scan is done by acquiring complex-valued samples of multiple echoes, while applying a gradient sequence concurrently, as well as in sequence with the echoes. Imaging relies on frequency encode for one of the dimensions because this allows a line in k-space to be acquired with each phase encode rather than a single point. For 3-dimensional imaging, two dimensions in k-space normally rely on phase encode to generate the targeted filling of k-space, with the third dimension frequency-encoded. Phase encode acquisition in imaging usually entails acquisition of on the order of 256 k-values in each of the phase-encode directions, hence is a relatively slow process. Clinical MRI scans take on the order of 10-15 minutes to generate an image. The aim in image construction is to acquire sufficient k-space coverage to fill out all the coefficients in the 2 or 3-dimensional Fourier series, which is why in standard MR resolution is limited by subject motion.

The embodiments disclosed herein is in direct contrast to standard MR data acquisition, with its focus on image generation Image formation is plagued by blurring resulting from subject motion over the long time necessary to acquire the large data matrix required. Since the target of the embodiments disclosed herein is texture rather than image, the only requirement on subject motion is that the sampled volume remain within a region of similar tissue properties over the course of acquiring data. This is a much less stringent and easy to achieve target than the requirement of structural phase coherence, as the scale of the allowable motion is then large enough, and of a temporal order, to be easily correctable by real-time motion assessment and correction techniques. The speed of acquisition for the embodiments disclosed herein is such that, in most cases, real-time motion correction may not be necessary at all. While other methods have focused on post-processing of images to try to extract textural measures, the embodiments disclosed herein eliminates the need for image generation, focusing instead on directly measuring texture, hence enabling a more sensitive and robust measure.

Frequently, k-space sampling is considered synonymous with sampling of an echo in the presence of a gradient set. In certain embodiments disclosed herein, the approach to k-space filling is to acquire only the set of k-values needed for texture evaluation in the targeted pathology, with data acquired after the gradient is switched off. This method enables such rapid acquisition of single-k-value repeats for averaging for noise reduction that subject motion does not degrade the data.

Along with the huge improvement in SNR that arises from sampling k-values individually, with many repeats of a select set of k-values acquired in a single TR, or single excitation pulse, acquisition after the gradient is switched off allows further significant improvement in SNR and hence, increase in measurement robustness. This is explained in the following discussion.

These same benefits of improved SNR can be achieved with the gradient ON during signal acquisition, allowing acquisition across an evolving range of k-values, as long as the gradient is low enough. Signal can be acquired in the presence of a low gradient used to provide specified trajectory across a small range in k-space during data acquisition.

MR echo sampling provides specific samples vs. time of a time-dependent echo. The echo is comprised by the gradients applied concurrently (for the frequency-encode axis) and prior to (for a phase encode axis), but also contains the isochromats associated with the different chemical species of the sample, as well as the envelope (T2 & T2*) associated with spin-spin interactions.

Conventional frequency-encoded spin acquisitions impose a time-varying gradient upon the sample, which effectively travels in k-space along a pre-defined path. For rectilinear sampling, the path is along a straight line.

Frequency encodes generate only one measurement at a given k-value—at a given point in time, the acquired sample of the echo represents the one value which corresponds to the Fourier coefficient at a specific k-space location. The next echo sample represents the value at a different k-space location, the next k-value dependent on the slope of the gradient applied concurrently. As long as there is sufficient signal at the corresponding k-value, this approach works well. However, in cases where the signal of interest is near or even below the noise floor, usually additional samples and subsequent post-processing will be required.

One way to reduce the noise floor in a frequency-encoded gradient read-out is to reduce the gradient strength and lower the receiver bandwidth. Decreasing the receiver bandwidth will indeed decrease the noise level, and improve lower signal level detection (proportional to the term $k_B$ TB, with $k_B$ corresponding to Boltzmann's constant, T corresponding to Temperature in Kelvin, and B is the receiver bandwidth in Hz.) However, this comes at the expense of larger chemical shift artifacts.

Chemical shift artifacts arise as a consequence of the different isochromats associated with different chemical species within the biological sample. In a frequency-encoded k-space read-out, those chemical species which resonate at a slightly higher frequency will appear to be displaced from their actual location in image space towards the direction of increasing frequency. If the spatial frequency encoding gradient is shallow, the apparent displacement can be quite large.

As such, to minimize chemical shift artifacts, the gradient slope is typically made as steep as possible to minimize the apparent shift to within a narrow range (i.e. within 1 or two pixels in the image domain). However, this then requires a larger receiver bandwidth to accommodate the larger frequency range. This in turn increases the overall noise floor at a level proportional to the receive bandwidth.

The conclusion is that frequency readouts generally force a trade-off between gradient strength, noise level, and chemical shift artifacts.

A common technique for noise reduction in signal acquisition is through repeat sampling of a signal and subsequent combination of the multiple measurements. For linear noise sources, such as Gaussian noise, this technique improves SNR through cancellation of the random noise on the signal, the cancellation effect increasing with the number of samples, N.

Noise reduction by this cancellation technique works for static subjects. However, motion-induced blurring is a non-linear effect, so signal combining for which the individual measurements have shifted through large spatial phase angles (relative to the textural/structural wavelengths under study) does not lead to an improved SNR. A fairly standard technique to correct for motion is to look at the MR intensity data in real space and reregister successive traces/images to each other to maximize overlap. It is assumed that, as with the reduction in white noise, linear combination of these reregistered signals will result in reduction of the blurring caused by the motion. However, this only works if the SNR on each individual acquisition is high enough. Reregistering low SNR samples results in a high variance in the estimated position. Threshold theory defines that combining reregistered signals with non-linear blurring, when the original signals are below a certain noise threshold, only increases signal error.

The nonlinearity introduced by subject motion increases at higher k-values, since the motion-induced textural phase shift increases with k—i.e. as the size of the structures of interest decrease, the adverse consequence of motion become more acute. This implies that the multiple samples to be combined need to be derived from the same acquisition sequence, acquired in a sufficiently short time span, to ensure there is negligible motion between samples.

The Cramér-Rao Lower Bound provides insight into the number of samples that are required for a lower bound on the residual variance of an estimate, i.e. the SNR vs. number of samples, in Additive White Gaussian Noise (AWGN). For low source SNRs in AWGN, one needs a large number of samples to average in order to obtain a usable SNR. The primary assumption is that multiple acquisitions can be taken, then averaged to achieve the higher SNR. (CRAMÉR, H.; "Mathematical Methods of Statistics"; Princeton University Press, 1946. RAO, C. R., "Information and the accuracy attainable in the estimation of statistical parameters"; Bulletin of the Calcutta Mathematical Society 37, 1945.)

Referring to the drawings, the graph in FIG. 1 comparing output SNR shown in trace 102 with number of samples required shown in trace 104 demonstrates that, for high input SNRs, a single sample is sufficient to yield a low noise measure. For lower SNRs, multiple samples are required to "average out" the noise contribution. The ability to combine the samples explicitly assumes that the underlying signal of interest is relatively constant during the multiple sample acquisition process (i.e. the only component which changes is the noise).

Figure 2:
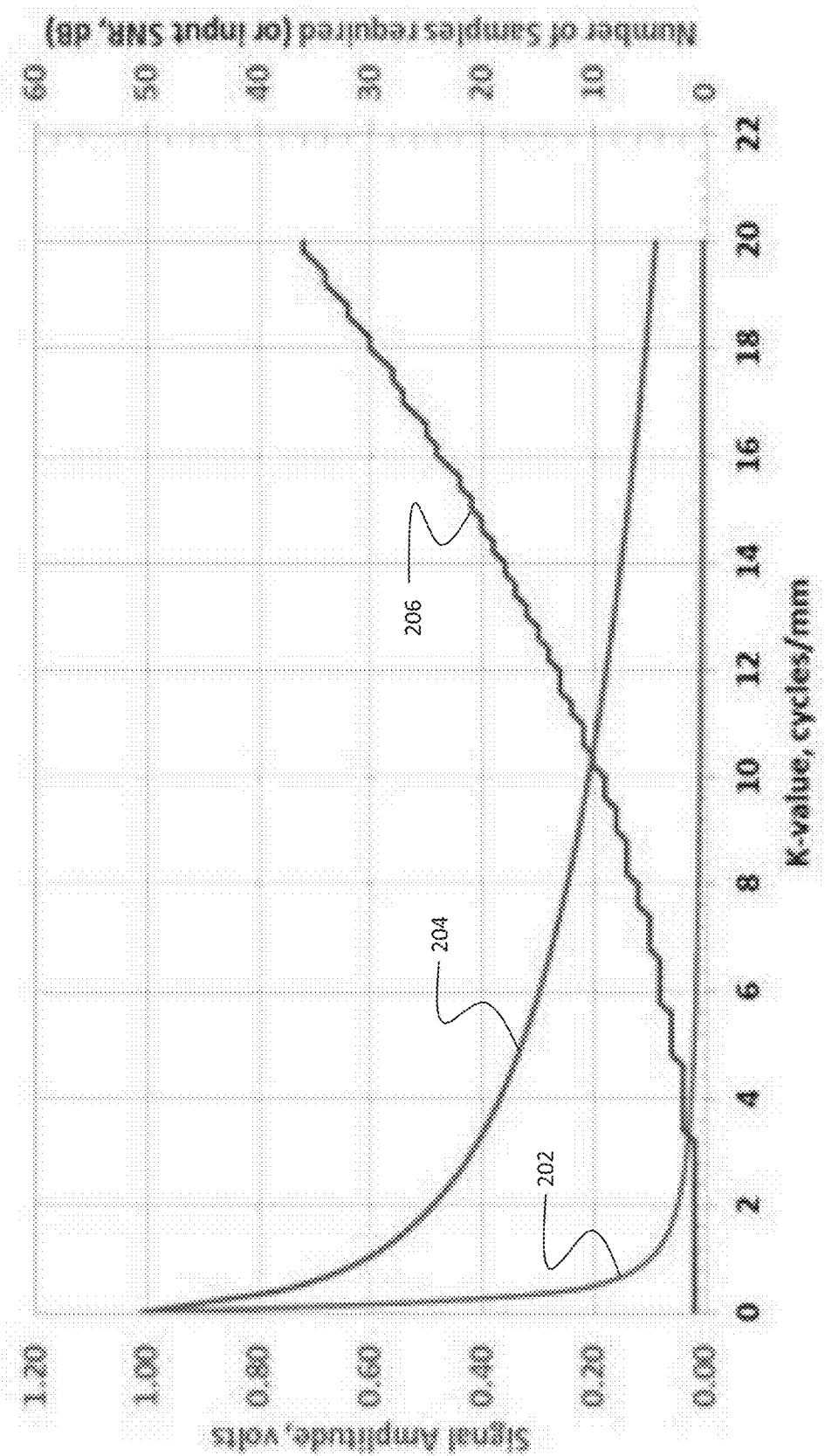
FIG. 2 is a simulation showing the number of data samples needed for averaging to achieve a SNR≥20 db as a function of location in k-space.

The graph in FIG. 2 is a simulation with signal model, trace 202, providing an input SNR, trace 204, showing number of samples of k-value, trace 206, needed to yield a SNR of 20 dB as a function of location in k-space, given an input noise level of 3 mV rms. Since spectral energy density is generally proportional to $k^{-1}$, to maintain adequate SNR a larger number of input samples is required at higher spatial frequencies (higher k-values). The noise level for the simulation is adjusted for ~10 dB SNR at k=2 cycles/mm ($\lambda$=500 µm).

As pointed out above, this type of averaging is possible for purely static samples with no displacement or deformation of the targeted tissue occurring over the temporal span of data acquisition. However, for in vivo applications, natural motion occurs even if the patient is compliant. As the texture spacing of interest decreases, the adverse consequences of motion become more acute. More to the point, this type of averaging is based upon the assumption that the underlying signal is the same across acquisitions, and that only the zero-mean, complex-valued, additive, white Gaussian noise (CAWGN) changes. If the signal itself changes, the result will be an average, not only of the noise, but also of the N different versions of the underlying signal, which really doesn't improve SNR.

Using low SNR samples to estimate and correct for motion will result in a high variance of the estimated position. This in turn yields a large variance in the "corrected" acquisitions and does not yield the anticipated increase in SNR when these acquisitions are averaged. This implies that the multiple samples need to be derived from the same acquisition sequence, where motion between samples is extremely small. This is enabled by the embodiments disclosed herein.

The issue becomes more acute with shorter structural wavelengths. Consider two acquisitions, noise-free for the moment, one of which has been displaced by an amount d. For a given k-value, an attempt to average them produces:

$$Y(2\pi k):=S(2\pi k)[1+e^{-j2\pi kd}]/2 \qquad (0.1)$$

Where $S(2\pi k)$ the complex-valued signal, and $Y(2\pi k)$ represents the average of the two acquisitions.

This can be expressed as:

$$Y(2\pi k):=S(2\pi k)e^{-j\pi kd}\cos(\pi kd) \qquad (0.2)$$

Which shows both a magnitude attenuation and phase shift, due to the displacement d. Limiting the magnitude attenuation to a floor value a, where 0<a<1, limits d to:

$$|d| \le \frac{\cos^{-1}(a)}{\pi k} \qquad (0.3)$$

This shows that, for a given magnitude error, the allowable displacement decreases with increasing values of k.

This is because, the smaller the textural spacing of interest, the less motion can be tolerated over the course of data acquisition.

To deal with this problem, an alternate approach is taken in the embodiments disclosed herein, which is to dispense with the frequency-encoded readout and to sample specific k-space points, acquiring one or multiple measurements at each k-value of interest at a single spatial location and orientation at a time.

Within a given acquisition in standard MR practice, there are M samples which are acquired of the echo. Instead of acquiring a sample at each k-value, N≤M of those samples could be used for estimation of the (complex-valued) underlying signal value at a specific k-value. Multiple samples within an acquisition can be combined with much less concern of movement than across acquisitions because they are much closer in time.

If the entire echo is used to measure one k-value, the receive bandwidth can be adjusted so as to pass the most abundant resonant peaks in the underlying NMR spectrum, and attenuate frequencies above them.

Taking a straight MRS spectrum (no structural phase encodes), would yield a spectrum consisting primarily of peaks corresponding to H$_2$O (with a chemical shift of δ=4.7 ppm), as well as Carbon-Hydrogen bonds which occur in fat (e.g. CH3, CH2, CH═CH, etc.), each with a different chemical shift ranging from 0.9-5.7 ppm, with the most abundant resonance coming from CH2 in the aliphatic chain which occurs at δ=1.3 ppm.

Assuming use of a 3T machine, since the Gyromagnetic ratio of Hydrogen is γ=42.576 MHz/T, the chemical shift values are in the range of 166 Hz (for CH2) to 600.3 Hz (for H2O). As long as a (single sided) receiver bandwidth in excess of 600.3 Hz is used, the H$_2$O peak will pass. Assuming baseband sampling, this implies a sampling rate >1.2 kHz (note, if complex base-band sampling is used, this could theoretically be reduced by about ½.) The point here is that a narrow bandwidth can be used by this method, and sample rates on the order of 800 μs. Noise on the signal is thereby reduced and multiple repeats of the k-value acquisition data are acquired in milliseconds, thereby making the acquired data immune to patient motion. For comparison, a single imaging acquisition is made with a TE of ~30 ms, and TR on the order of 500 ms-2000 ms. To acquire the repeats necessary for signal averaging can take minutes—a temporal range wherein respiratory, cardiac, and twitching motion limits resolution through motion-induced blurring. The claimed method enables acquisition of values in regions of k-space which have very low signal levels, such as would be found for higher k-values (shorter textural-wavelengths)— the fine texture range that has hitherto remained elusive.

To maximize the signal, the non-zero frequencies of abundance are selected. In general, this does not correspond to a mere averaging of all of the samples acquired. Instead it is akin to a matched filter which is "tuned" to the frequency of interest, corresponding to the specific chemical species of interest.

As a side note, the full NMR spectrum may be extracted (without any phase encoding gradients: just volume selection) to obtain a baseline of the underlying signal strength (and associated frequencies), which in turn will be spatially modulated, providing insight into textural wavelengths through knowledge of the chemical species expected in the textural elements under study.

The isochromats of interest can be extracted by acquiring N samples of the echo, then taking the Fourier transform. Since the echo is being played out with no gradient, the strength of the resulting signal at the Isochromat of interest will correspond to the (complex-valued) k-value coefficient of interest.

Given the goal is to extract the relative magnitude of textural wavelengths, just the magnitude vs. textural wavelength measurement is the required information. However, in order to extract sufficient signal strength and differentiate it from the underlying noise floor, the complex phasor values must be preserved until the end.

The relationship between the noise floor, the signal strength (at a specific isochromat where there is an abundance of chemical species), the number of samples required, and the max tolerated error can be approximated as $$N \geq \frac{\sigma^2}{|A|^2 \varepsilon^2} \tag{0.4}$$

Where $\sigma^2$ represents the noise variance, $|A|^2$ represents the squared magnitude of the isochromat(s) of interest, and $0 < \varepsilon < 1$ represents the allowable error of the estimate. Further assuming that the noise is mostly sourced from the biological sample, this can be further approximated as:

$$N \geq \frac{NF_{eff} \cdot k_B TB}{|A|^2 \varepsilon^2} \tag{0.5}$$

Where $NF_{eff}$ is the effective noise figure of the receiver, $k_B$ is Boltzmann's constant, T is the temperature in Kelvin of the biological sample, and B is the receiver bandwidth. In this case, N can be used as a guide to the number of samples that need to be acquired within a given acquisition in order to create a reasonable estimate.

If the number of samples required exceeds the number available in one acquisition, combination of measurements from a single acquisition may be needed to maximize the signal, prior to spatial reregistration between acquisitions. A reasonable estimate and displacement correction between the two or more acquisition sets is needed. Combination of measurements at a single k-value from a single TR block can now be used to boost the SNR such that reregistration between successive TRs has a much greater chance of success.

While the entire set of samples acquired in an echo or entire TR could be allocated to the estimate of one coefficient in k-space, if acceptable values can be estimated using fewer than the maximum number of echo samples, it opens up the possibility of being able to acquire more than one coefficient in k-space within a specific echo or TR.

Figure 3:
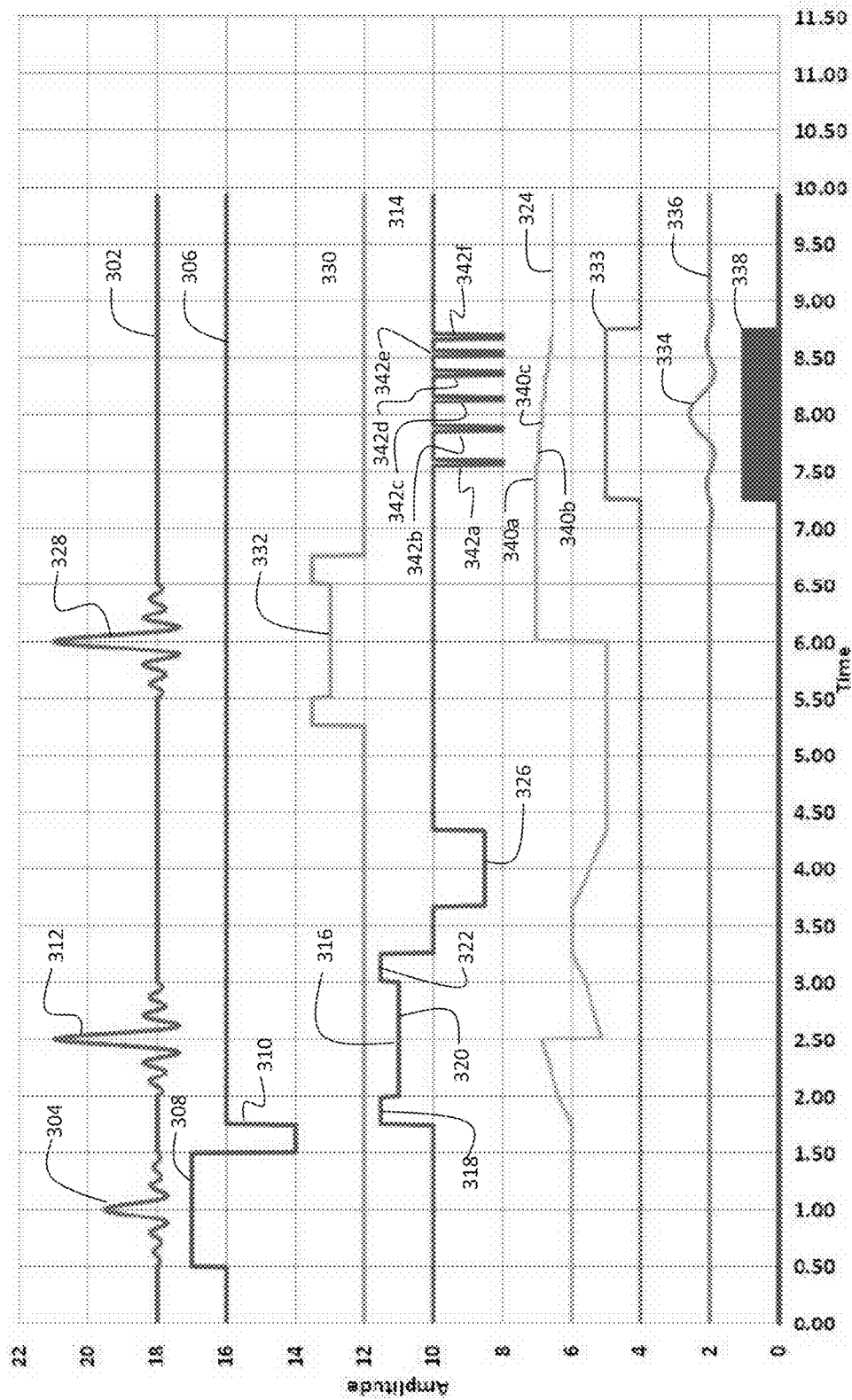
FIG. 3 is an example timing diagram of a pulse sequence for the claimed method showing the timing of a single TR.

Various pulse sequences are provided for exemplary implementations of the embodiments disclosed herein. The examples may be combined with each other and with other MR imaging techniques, in parallel and in integrated forms, to obtain the desired micro-texture imaging associated with investigation of diseases having various pathologies. FIG. 3 shows an example timing diagram for a pulse sequence for data acquisition using the embodiments disclosed herein. RF pulses included in trace 302 are employed to excite selected volumes of the tissue under investigation, as in typical MR imaging. A first RF pulse, 304, is transmitted coincidentally with a gradient pulse 308 on the first magnetic field gradient, represented in trace 306. This excites a single slice, or slab, of tissue the positioning of which is dependent on the orientation and magnitude of the first gradient, and the frequencies contained in the RF pulse. The negative gradient pulse, pulse 310, rephases the excitation within the defined thickness of the slice or slab.

A second RF pulse 312, at twice the magnitude of first RF pulse 304, is transmitted coincidentally with gradient pulse 316, on a second gradient, represented in trace 314, exciting a slice-selective refocus of spins, this second tissue slice intersecting with the first. (As this second RF pulse 312 tips the net magnetic vector to antiparallel to $B_0$, it results in inversion of spins and subsequent refocusing, thus leading to a signal echo at a time after the 180 degree RF pulse equivalent to the time between the 90° and 180° RF pulses.) An initial higher value gradient pulse, 318, at the start of gradient pulse 316 is a crusher, or "spoiler" gradient, designed to induce a large phase wrap across the tissue volume. A similar gradient pulse, 322, at the trailing end of pulse 316, as it comes after the 180 degree RF inversion pulse, unwinds this phase wrap. In this way, any excitation that is not present prior to the 180 degree RF pulse, such as excitations from imperfections in the 180 pulse itself, will not have this pre-encode so will not be refocused by the second crusher, hence will not contribute to the signal. In summary, the second RF pulse, in combination with the applied second gradient, provides slice selective refocusing of the signal in a region defined by the intersection of the first slice and the second slice set by this second gradient.

An encoding gradient pulse 326, on trace 314, sets an initial phase wrap, hence k-value encode, along the direction of gradient pulse 326. In general, the k-value encode can be oriented in any direction, by vector combination of the machine gradients but for ease of visualization is represented as on the second gradient.

A refocusing third RF pulse 328, applied in combination with gradient pulse 332 on a third gradient, represented by trace 330, defines a third intersecting slice selective refocus to define the VOL. Gradient pulse 332 again employs crusher gradients.

The negative prephasing gradient pulse 326 winds up phase such that, at the signal echo following the second 180° RF pulse, signal acquisition starts at high k-value, which may then be subsequently decremented (or incremented or varied in orientation) for further acquisitions, as will be described below. As energy density in the signal is generally proportional to $k^{-1}$, this method ensures k-values with lower SNR are acquired first, before $T_2$ effects have caused much overall signal reduction.

With all gradients off, a receive gate 333 is opened to receive the RF signal, which is shown in FIG. 3 as pulse 334 on trace 336. The RF signal in trace 336 is a representation showing only the signal present in the receive gate window without showing the actual details of the RF signal outside the window. Sampling occurs as represented by trace 338 beginning with the initial k-value, 340a, seen on trace 324. Note that, at the scale of the drawing, the sampling rate is high enough that the individual triggers of the analog to digital converter (A/D) have merged together in trace 338. (The expanded time scale in FIG. 4 described below shows the individual A/D triggers.)

In regions of k-space where the corresponding coefficients are sufficiently large that they can be well-estimated using a small subset of the samples of one echo, acquisition of another k-value, obtained by applying a gradient pulse 342a shown on trace 314, to select a new k-value, during the time the echo is being recorded, is accomplished. After a suitable settling time, another set of samples of the echo (now derived from the new k-value coefficient) can be collected. This process can be repeated, acquiring multiple samples at each of a select set of k-values within one TR. A plurality of samples are taken at the initial k-value 340a. A k-value selection gradient pulse 342a is then applied and the resultant k-value 340b is sampled. (Though shown in the figure as a negative pulse on the second gradient, decrementing the k-value, in practice this pulse and subsequent k-value gradient pulses can be designed through any vector combination of gradients to select any k-value or orientation.) Similarly, the k-value selection gradient pulse 342b, selects a third k-value 340c which is sampled by the A/D. Each gradient pulse changes the phase wrap, selecting a new k-value. Application of a k-value selection gradient pulse (342c-342f) followed by multiple sampling of the resultant k-value coefficient is repeated as many times as desired. While data is being acquired throughout, the samples of interest are acquired when all gradients are off. The gradient orientations for slice and k-value select may be coincident with the machine gradients, which are aligned to lie coincident or orthogonal to the $B_0$ field. Alternatively, the acquisition directions and k-value encodes may be selected using gradients that are a vector combination of all three machine-gradient axes.

In the circumstance where it is desired to measure a low SNR k-value the prewinding encoding gradient pulse can be set such that the first k-value to be measured is the desired low SNR k-value. Alternatively, the prewinding gradient pulse can be set to zero so that the first k-value measured is k0. A measurement of k0 may be desired for the purpose of determining the systems receiver sensitivity to the particular VOI, determining the relative prevalence of isochromats (e.g., water vs. lipids) irrespective of texture in the VOI, or for the purpose of establishing a reference value for normalization of the other k-values measured in a VOI or for comparison with k-values from other VOI. Furthermore a strategy for gathering a specified set of k-values for a VOI may include measuring the low SNR k-values (typically the higher k-values) in a first set of multiple TR and then measuring k0 and other higher SNR k-values in other TRs while remaining in the same VOI.

As is shown diagrammatically in FIG. 3, the signal reaches a maximum at the time of the spin echo. It is also shown diagrammatically that the signal is varying throughout the acquisition of the multiple RF measurements of a k-value and more so between successive blocks of measurements of k-values. Alignment in time of the measurement of the low SNR k-values with the highest echo signal enhances the SNR of the k-value measurement, alternatively alignment of higher SNR k-values with lower echo signal allows gathering additional useful k-value acquisitions during the echo. The term k-value measurement is understood in the art to be a "shorthand" term for measurement of signal at a k-value.

Figure 4:
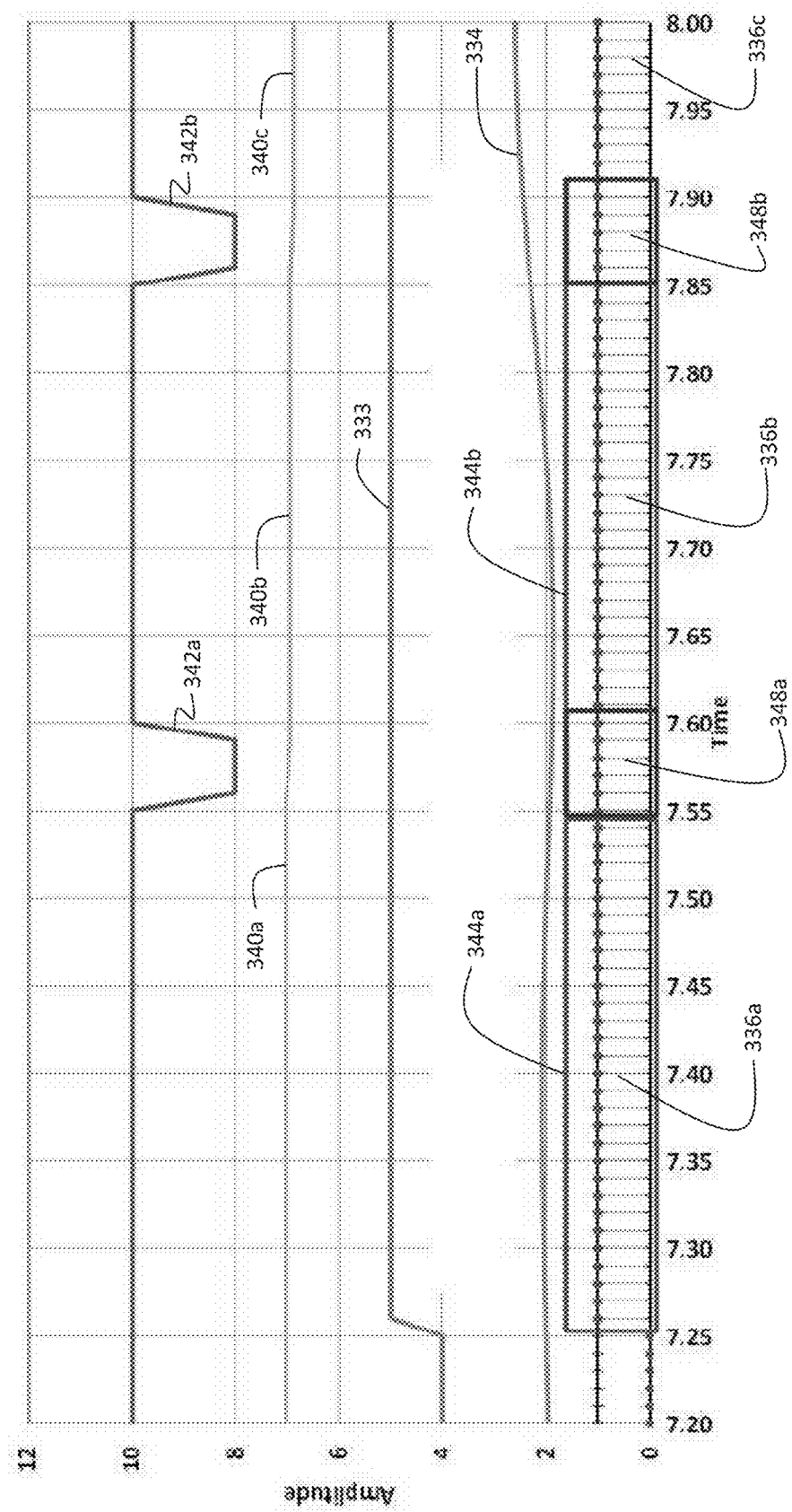
FIG. 4 is a close-up of the example timing diagram of FIG. 3.

FIG. 4 shows a close-up of the pulse sequence of FIG. 3 during the initial portion of the RF sampling window 338 between 7.25 and 8.00 msec. Multiple samples of the same k-value, taken in rapid succession with all gradients off, provide the input for signal averaging to reduce AWGN when SNR is low. In a first block 344a of the sampling window 338, multiple samples 346a are taken of the first k-value 340a. During application of the k-value selection gradient pulse 342a, transition samples 348a are taken. When the k-value selection gradient is switched off, multiple samples 346b are taken at the second k-value 340b. Application of k-value selection gradient pulse 342b then occurs with associated transition samples 348b, and subsequent acquisition of samples 346c of the third k-value 340c after the gradients are switched off. The underlying signal is minimally impacted by motion due to the very short time window used to acquire data at each given k-value. Since the data is acquired with gradients off, there is no issue with chemical shift and the effective $T_2^*$ is longer, boosting the signal value.

The sampled values of the echo, acquired while the k-value selection gradient pulse is ramped up, held steady, and then ramped down to zero, will necessarily be influenced by the applied gradient. These transition samples may provide other interesting information, but are not used in the consideration of a straight measurement of the k-value coefficient; only those samples which are recorded when there is no gradient currently active are used for this.

Figure 5:
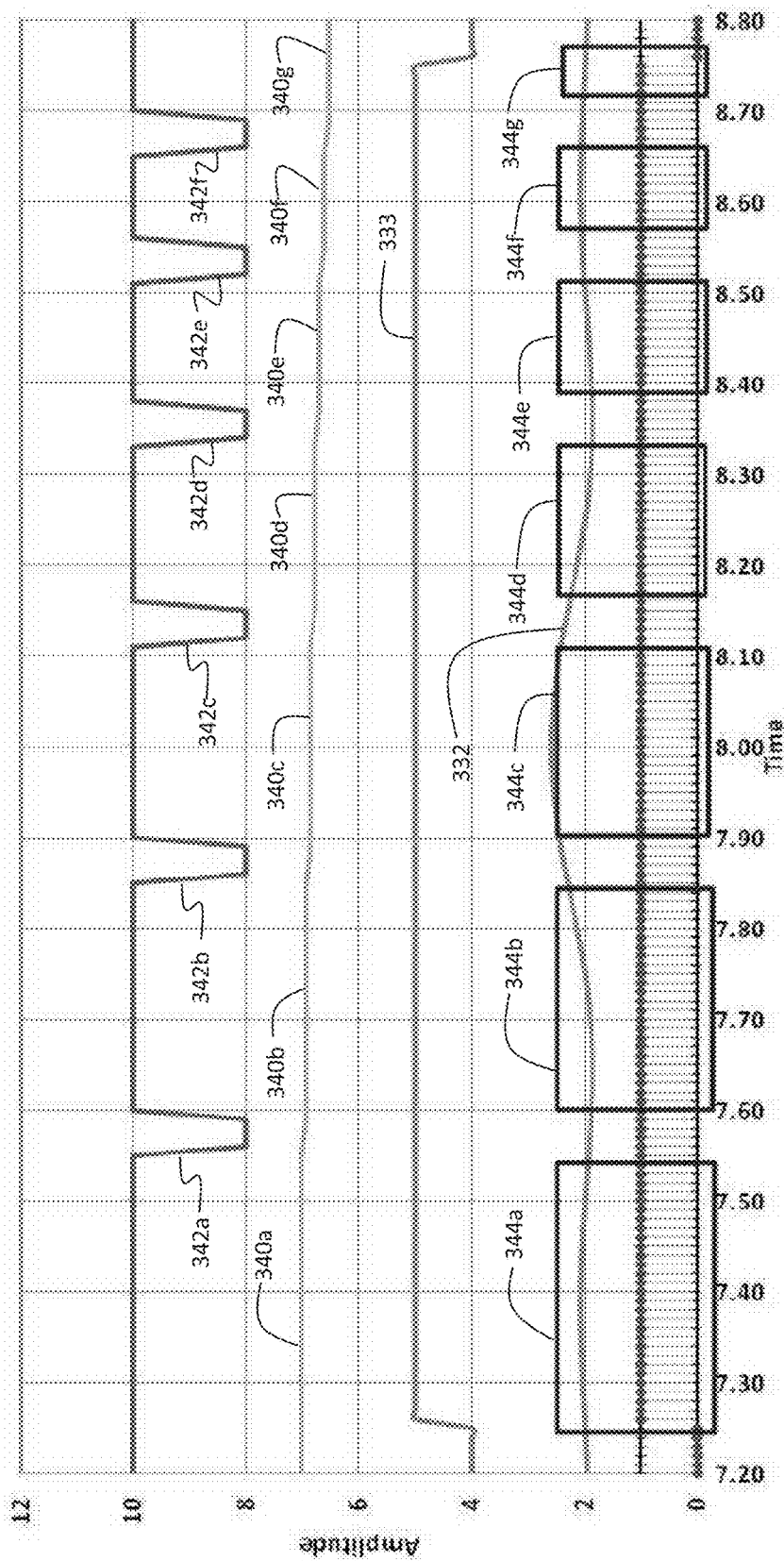
FIG. 5 is an example of a timing diagram for the claimed method, designed to acquire multiple measures of a select set of k-values, with a different number of samples acquired at each k-value to counteract the decrease in energy density at increasing k-value.

A consistent number of samples at each k-value can be acquired, or an alternative sequence may be employed where, as k-values decrease, hence increasing in signal amplitude, fewer samples are acquired. A pulse sequence designed for this type of acquisition is illustrated in FIG. 5. Multiple samples of each k-value targeted in the acquisition are acquired in rapid succession, with all gradients off. These repeats provide the input for signal averaging in low SNR signals. As with the pulse sequence, depicted in FIGS. 3 and 4, the underlying signal is minimally impacted by motion due to the very short time window in which data is acquired for a given k-value.

Samples within the portions of the sample window 344a-344g outlined on FIG. 5 correspond to the number of samples acquired for a given k-value 340a-340g each induced by an unwinding pulse 342a-342f of the k-value selection gradient. $N_k$, the number of samples associated with a given k-value, can be selected based upon expected SNR, tissue contrast, contrast to noise, pathology, texture size, and/or texture bandwidth. For the example in FIG. 5 it can be seen that a decreasing number of samples are taken for progressively smaller k-values (larger textural features). This is because, as previously discussed, to first order signal amplitude increases with decreasing k-value—energy density is generally proportional to $k^{-1}$. For this same reason, larger k-values are acquired first in this scheme, when T2 effects are least, the longer wavelength, higher signal strength, k-values being recorded later in the acquisition.

Refocusing the echo, and/or a new TR can be used to build up a library of k-space samples. Acquisition of multiple k-values within one TR can be facilitated by application of multiple refocusing gradients and/or RF pulses, to increase the time over which the additional k-values can be sampled within a TR. These later echoes would presumably be used to acquire the coefficients of the lower k-values in the selected set, as their energy density in the continuum of values is generally higher so the effect of $T_2$ decay on overall signal will not affect them as severely as it would the higher k-values. In this way a larger portion of the required k-space filling can be accomplished over fewer TRs, allowing more rapid data acquisition, minimizing the need for repositioning the VOI.

Figure 8:
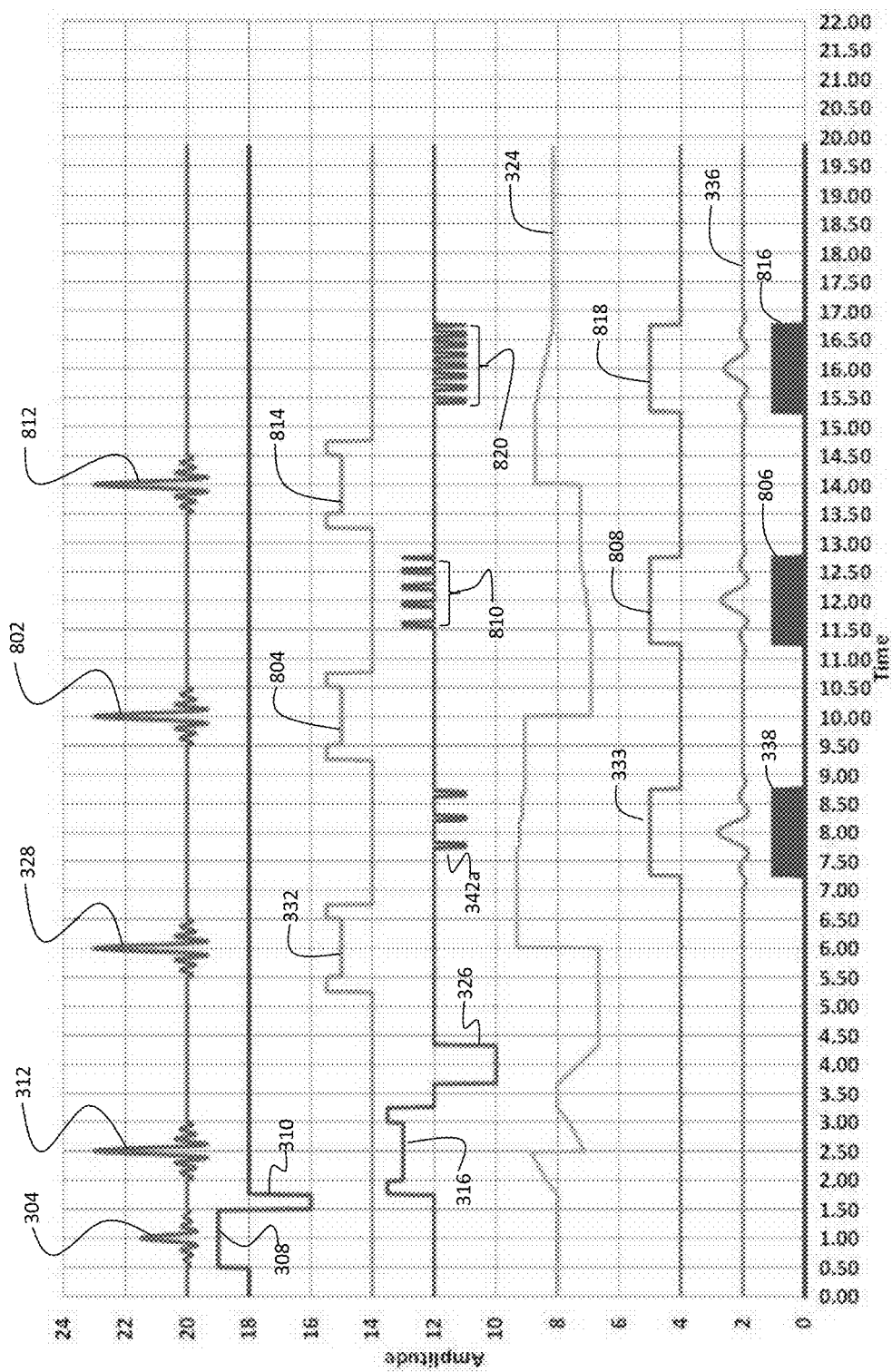
FIG. 8 is an example timing diagram for the claimed method designed to provide data acquisition over multiple refocused echoes within a single TR; and, FIGS. 9 and 10 are a depiction of two possible shapes for the acquisition volume of interest (VOI)

FIG. 8 shows an extension of the basic sequence of the embodiments disclosed herein, using spin-echo refocusing to extend the record time for the TR. Application of a refocusing RF pulse 802 with an associated gradient pulse 804 results in slice-selective refocusing. After an appropriate settling time, a second sampling window 806 is opened by the receive gate 808. Multiple k-value selection gradient pulses 810 are applied to increment the selected k-value and, after switching off each successive gradient pulse, multiple samples of the selected k-value are acquired in the sampling window. A second slice-selective refocusing RF pulse 812 with associated gradient pulse 814 again inverts the spins and, after application of each in the multiplicity of k-value selection gradient pulses 820, data is acquired in a third sampling window 816, opened by the receive gate 818. As shown in the drawing, an increasing number of k-values may be sampled with each refocusing. Refocusing can be repeated until the decrease in signal level from T2 and other effects makes further signal acquisition ineffective. Another method to extend the record time by exciting multiple signal echoes, is to use one, or a series of, gradient recalled echoes (GRE). GRE are different from the SE in that they cannot refocus the effects of stationary inhomogeneities, so T2* effects limit the number of repeats.

In addition to the tissue contrast available, the k-values associated with particular pathology will be part of the determination of the number of samples needed for signal averaging, $N_k$. In liver fibrosis, as an example, the wavelength of pertinent textures is in the range of 400 microns, i.e. a k-value of 2.5 cycles/mm. This is similar to the textural spacings seen in fibrotic development in many other diseases, such as cardiac fibrosis. The spacing of elements in trabecular bone varies a lot, but the minimum spacing of interest is the width of trabecular elements, which are approximately 80 microns, setting a maximum k-value of 12.5 cycles/mm. In neuropathology, many of the textures of interest are very fine, on the scale of 50 microns, equivalent to a k-value of 20 cycles/mm.

Each pathology will dictate what exactly is needed as quantitative data, i.e. what part of the continuum of k-values needs to be monitored, and with what resolution and sensitivity. In some pathologies, short (long) wavelength features increase at the expense of long (short) wavelength features (e.g. liver fibrosis). In other pathologies, an amplitude decrease and broadening of short wavelength features indicates disease progression—e.g. degradation of the ordered formation of cortical neuronal minicolumns (approximately 80-micron spacing) with advancing dementia. In bone, with increasing age, first the highest k-value features disappear in the structural spectrum. Next the major structural peaks shift slowly towards lower k-values with advancing osteoporosis, the pace of this shift accelerating as an increasing percentage of trabecular elements thin to the point that they break.

The signal level obtainable will depend on anatomy to some extent. For instance, though the resolution needed is highest in brain, the proximity of the cortex to the surface of the head ensures that use of a surface coil will provide significant signal boost for cortical structures. Lower resolution is required in liver, as the structures of interest are on the order of several hundred, rather than tens of microns. But, the organ is deeper (further from the coil) reducing the measured signal. Using the in-table coil for spine data acquisition yields modest signal level and good stabilization. Also, bone is a high contrast target, so the SNR requirement is not as stringent. For all these reasons, the exact number of repeats needed for averaging depends on more than the k-value range targeted.

Figure 6:
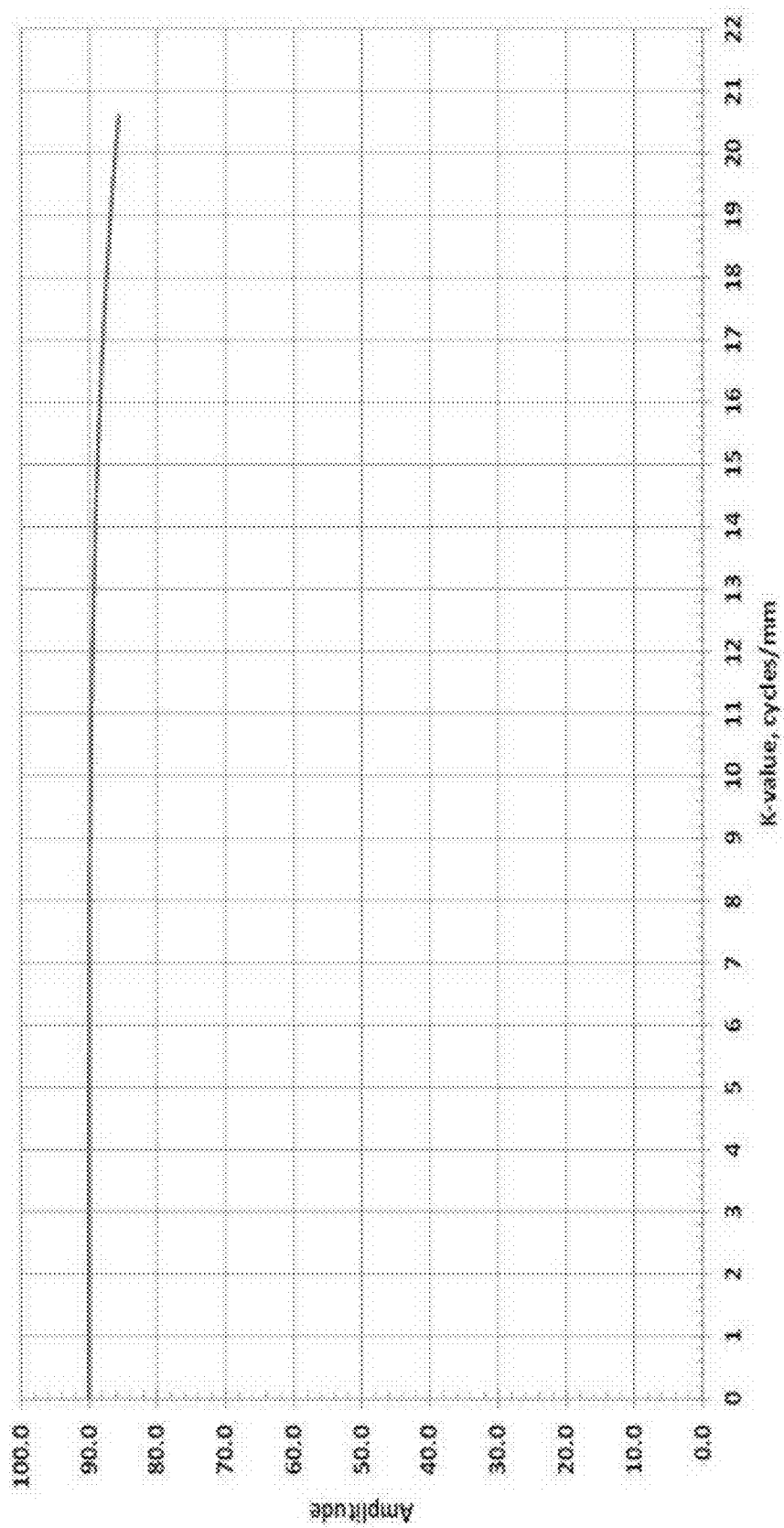
FIG. 6 is a simulation showing that the ability provided by the claimed method to acquire many repeats of signal at each targeted k-value within a single TR enables robust signal averaging to boost SNR.

FIG. 6 shows a simulation demonstrating that the ability provided by the claimed method to acquire many repeats of a targeted k-value within a single TR, or single excitation pulse, enables robust signal averaging to boost SNR. Assuming a subject displacement rate (which has in practice been measured clinically over the course of several scans) of 30 μm/sec, and a sampling rate=33.3 kHz (ΔTsample=30 μs), 90 repeat samples for averaging can be taken rapidly enough that, even up to a k-value of 20 cycles/mm (texture wavelength=50 μm), the acquisition remains immune to motion effects.

Figure 7:
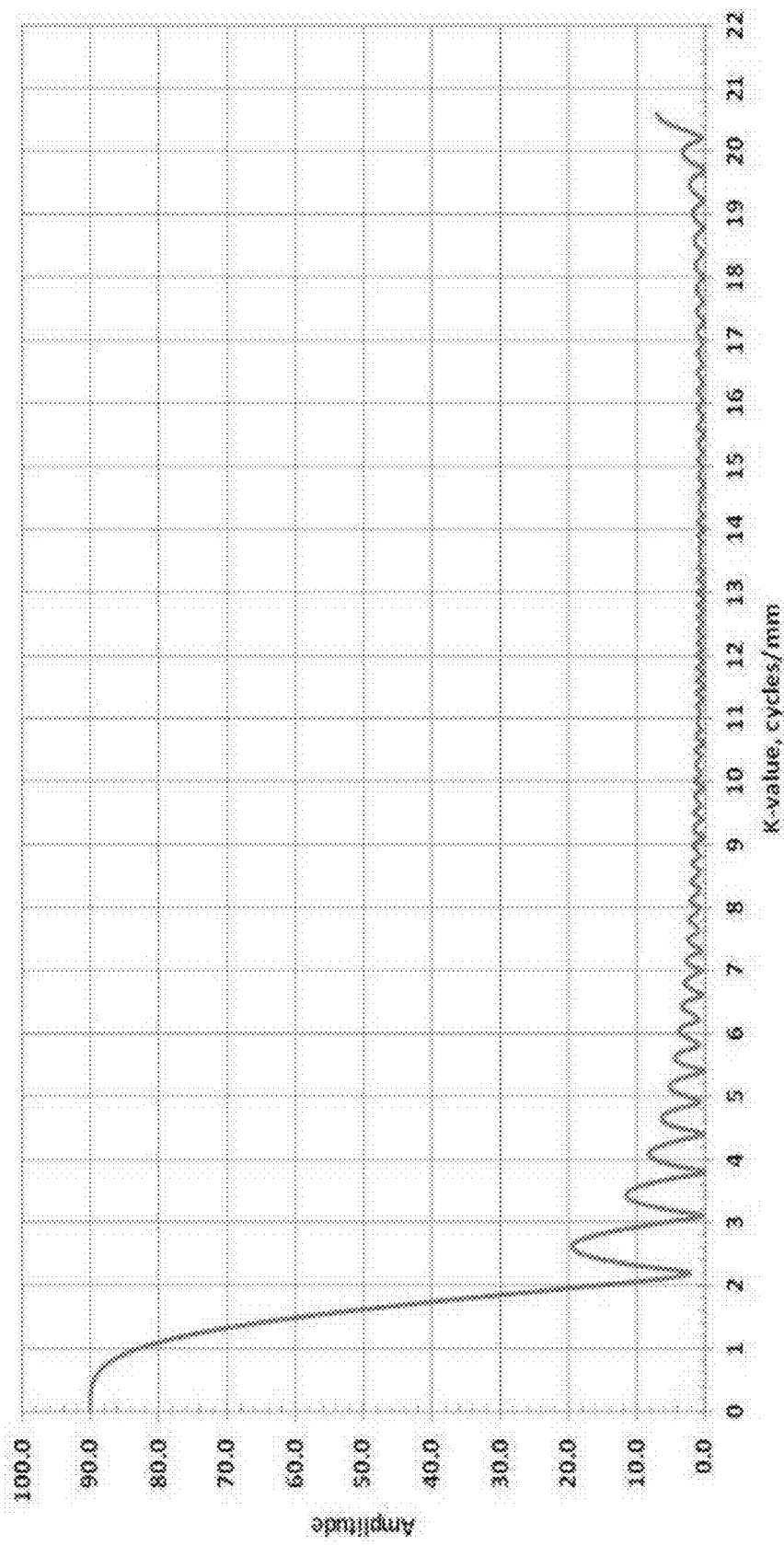
FIG. 7 is a simulation showing the results of attempting to acquire 90 samples for averaging using the conventional frequency-encoded echo approach, wherein acquisition of signal at only a small number of repeats of a particular k-value are possible in each TR due to the long record time for each echo.

FIG. 7 shows that, for comparison, using the conventional approach of acquisition of a spatially encoded echo, even assuming a relatively fast gradient refocus sequence, which would provide a sampling rate of about 67 Hz (ΔTsample=15 msec), subject motion over the time needed for 90 repeats would severely degrade the signal, and any ability to improve SNR by signal averaging. The situation is actually worse due to the fact that to acquire 90 repeats using conventional spatially-encoded echoes would require several TRs, making the acquisition time significantly longer, and the signal degradation due to motion much more severe. With the exception of the very lowest k-values, the potential SNR gain due to multiple sample combination has been nullified by the effects of motion.

By acquisition of a large enough selected range of k-values, construction of a structural profile in one or more dimensions becomes a possibility. As discussed above, refocusing echoes within a single TR or excitation pulse, or multiple TRs/pulses, can be used to build up a library of k-space samples. Phase coherence might not be maintained between different k-values if they are acquired in TRs separated temporally such that displacement has occurred between them. If a primary interest is in the relative strength of signals at particular k-values, this is not a problem. If creation of a profile or an image from this library of values is desired, the necessary post processing will have as input the high SNR measure obtained within each TR using the embodiments disclosed herein. These measures can then provide robust input for any required reregistration between echoes or TRs towards constructing a profile. As an example selection and measurement in a first TR of a set of selected k-values may be accomplished with at least one having a low k-value. In a subsequent TR, selection of the same set of k-values will allow re-registration of the data between the two TRs since even if significant motion has occurred the phase change in the low k-value phase shift will be less than for higher k-value textures and may be correlated between the two TRs. Basically, the higher the k-value, the greater the phase shift due to subject motion. Acquiring signal from successive encodes with a large difference in k-value enables a better estimate of phase shift by careful comparison of the apparent phase shift for each.

This is very similar to x-ray diffraction, wherein the magnitude-only information (no phase) obtained presents the challenge of determining a best estimate of the corresponding structural profile based on this magnitude-only information. Algorithms exist towards solving the problem, the chance of success depending on the range of k-value coefficients obtained, the SNR of each averaged coefficient, and the width of values contained in a nominally single-valued acquisition of k-value. The chance of success in this effort is greatly increased using the claimed method due to its immunity to subject motion.

The ability to reconstruct a profile from k-value data depends somewhat on the spectral broadness of each single-k-value acquisition. While this is influenced by the VOI (Volume of Interest) size and shape, it is also influenced by k-value and pathology, as degradation of tissue often tends to lead to more textural randomness within tissue.

Selection of the VOI—shape, dimensions, orientation, and positioning within an organ/anatomy affects the data measured and its interpretation. The VOI shape can be chosen to maximize usefulness of the acquired data. Data can be acquired in different directions, and at different textural wavelengths (k-values) within a VOI enabling assessment of textural anisotropy. Texture can be sampled in multiple VOIs, either interleaved within a single TR/excitation pulse, or in successive TRs, towards assessment of pathology variation across an organ. Standard interleaving processes for the VOI may be used within a TR to provide additional data by applying additional encoding pulses on vector combination gradients and associated k-value selection gradient pulses for k-values in the interleaved VOI. As previously described, additional excitation RF pulses with associated slice selection gradients may be repeated within the same TR by exciting a volume of interest with a gradient set in each repeat having at least a first gradient with an alternative orientation from the first gradient pulse 308 applied initially in the TR, to define an additional VOI for excitation in new tissue, that does not overlap any previous VOI in the TR (fourth, fifth and sixth gradients in a first repeat and succeeding incremental gradients in subsequent repeats). This response can be mapped, or the several measures taken and averaged, whatever is appropriate for the targeted pathology. This is similar to the multi-positioning of tissue biopsy. However, in the case of tissue biopsy, the number of repeats is limited due to the highly invasive nature of the technique. The minimum number of structural oscillations to be sampled at a specific k-value dictates a minimum VOI dimension in the direction of sampling—the length required varying inversely with targeted k-value.

To ensure adequate sampling of structure when targeting a range of k-values, the VOI dimension in the sampled direction can be held constant for all k-values in the targeted range, with the result that the number of structural oscillations sampled will vary with k-value. This is a simple solution, requiring the sampling dimension be set by the lowest k-value (longest wavelength structure). Using this approach, the sampling dimension of the VOI is larger than required for the highest k-value in the range, thus providing less localization within the tissue than would be otherwise possible.

Alternatively, data at widely differing k-values can be acquired in successive TRs, using changing VOIs tailored to the specific k-value targeted. Or, the dimensions of the VOI can be selected such that acquisition in different directions within the VOI will be tailored to sampling in a specific textural frequency (k-value) range.

Similarly, the VOI may be held constant and the vector combination gradient for the encoding and k-selection pulses may be altered from TR to TR for assessing feature size.

Figure 10:
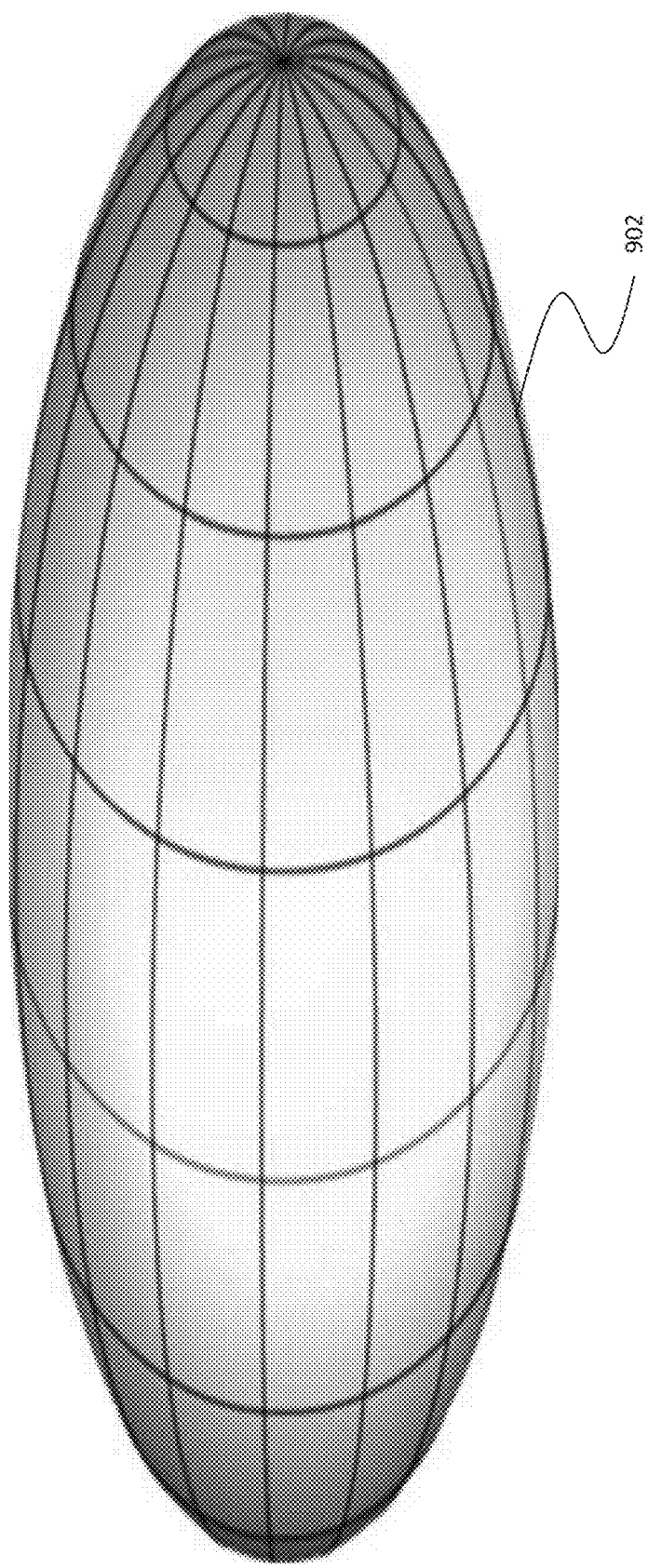

In some instances, it is desired to localize tightly in the spatial domain, to broaden the localization in k-space. By defining a non-cubic acquisition volume, it would be possible to acquire data from differing k-values along the different (orthogonal or other) directions within the VOI, within one TR. The elliptical cross-section VOI 902 in FIG. 10 is one such possibility. Acquisition along any radial direction, as well as along the axis of the shape, would be possible within one TR.

Additionally, the flexibility of the embodiments disclosed herein may be used to sample k-space in a linear or in a curved trajectory. For example, texture could be sampled along radial lines, or along an arc or a spiral, to extract information of textural sizes along different spatial directions. These methods can be used to determine the anisotropy of texture, or the sensitivity to alignment in structures that are semi-crystalline, such as cortical neuronal columns, or to more rapidly build up a library of k-values within a targeted extent of tissue in an organ.

During one TR (i.e., one 90 degree excitation) k-value encodes can be applied in multiple directions by changing the applied vector combination gradients for encoding and k-selection pulsing. The exact form of the VOI and sampling direction can be used to yield much textural information. For instance, the organization of cortical neuron fiber bundles is semi-crystalline, as the bundles in healthy tissue form in columns. Because of this, the measure of textural spacing perpendicular to the bundles is very sensitive to orientation. When the orientation is exactly normal to the columns, a very sharp signal maximum is expected, the signal falling off rapidly as the orientation varies on in either rotational direction away from this maximum. One way to measure the spacing and organizational integrity (a marker of pathology) would be to "rock" the acquisition axis around this maximum looking for a resonance in signal intensity. This approach of looking for "textural resonances" by looking for signal maxima can be applied in any tissue region. As pathology degrades the organizational integrity, the sharpness of this peak will degrade and the signal maximum will be reduced.

Similarly, the randomness of the spacing in certain textures can be assessed by varying the length of tissue sampled in a specific, or in multiple directions, with subsequent change in acquisition length. The selected value for that length can be varied over multiple TRs to test the sensitivity of the measured coefficient to this parameter.

Figure 9:
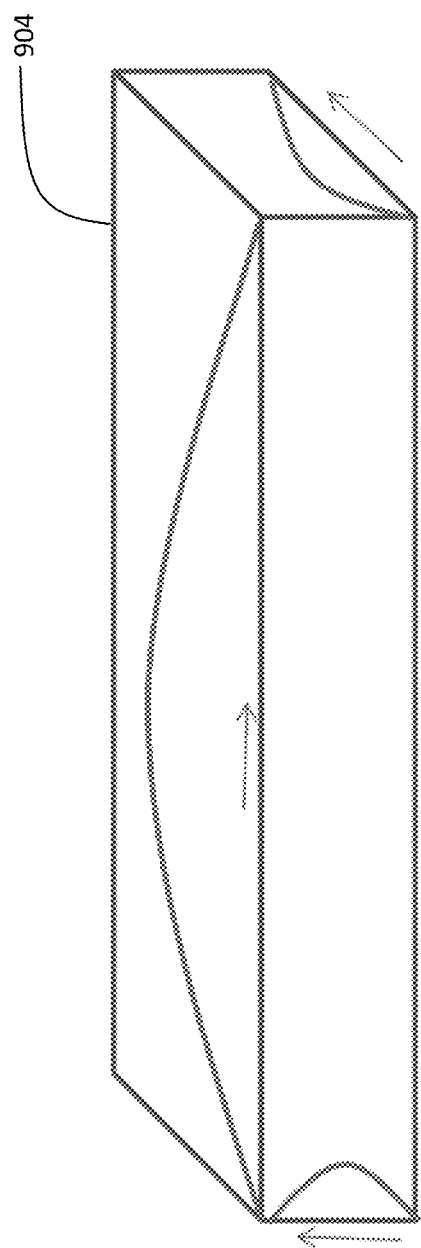

The VOI can be selectively excited by a number of methods, for instance intersecting slice-selective refocusing, selective excitation using phased-array transmit in combination with appropriate gradients, adiabatic pulse excitation to scramble signal from the tissue outside the region of interest, as examples. Parameter selection for the various methods can be done with SNR optimization in mind. For instance, the VOI generated by a slice selective excitation and two additional mutually-orthogonal slice selective refocusing pulses, as by VOI 904 in FIG. 9. Through careful RF pulse design, the shape of the VOI can be designed so that the edges are smooth and more approximate a windowing function, as shown in FIG. 10. These windowing functions provide the volume selection without adverse impact on the spatial frequencies. Recall, in Fourier theory, each spectral line is smeared by the convolution of a Fourier transform of the window function. It is desirable to minimize this smearing of the underlying spectrum, as it decreases the energy spectral density, and adversely impacts SNR.

Importantly, as has been discussed previously, the VOI can be moved from place to place within an organ or anatomy under study to measure the variation of texture/pathology. This response can be mapped, or the several measures taken and averaged, as appropriate for the targeted pathology. This is similar to the multi-positioning of tissue biopsy. However, in the case of tissue biopsy, the number of repeats is limited due to the highly invasive nature of the technique.

Different diseases and conditions affect tissue in different ways. Generally, pathology advancement entails: 1) a loss of energy density in specific regions of k-space, and/or 2) a shift in textural energy density from one part of k-space to another, both effects being accompanied by 3) changes in the width of existing peaks in the continuum of textural k-values. Using trabecular structure as an example—with decreasing bone health the average separation of trabecular elements widens (texture shifts to lower k-values) and becomes more amorphous (broader peaks in k-space), while in parallel the structural elements thin (a shift to higher k-values in a different part of the spectrum). Other tissues/organs are affected by diseases that have their own individual signatures in tissue texture.

Using the embodiments disclosed herein, k-space is probed to reveal texture in such a way as to eliminate the loss of signal resolution that results from subject motion blurring. Instead of measuring the large continuum of k-values needed to create an image, the focus here is on acquisition of a select few k-values per TR, with sufficient repeats of each to yield high SNR. Each of the individual acquisitions is centered on a single k-value. While the spatial encode is, to first order, a single spatial frequency sinusoidal encode, there are a number of factors which have the effect of broadening the spatial frequency selectivity of the k-value measurement. One significant factor affecting the broadness, or bandwidth, of the k-value measurement is the length of the sampled tissue region. A longer sampling length encompasses more textural wavelengths along the sampled direction, which has the effect of narrowing the bandwidth of the k-value measurement. (This is the inverse relationship between extent of a measurement in real and in k-space.) Hence, an aspect of the claimed method is the ability to set the bandwidth of the k-value measurements by appropriate selection of the sampling length determined by the VOI dimensions or determined by the acquisition dimensions. Using this method, the bandwidth of the measurement can be set according to the desired k-space resolution appropriate to the tissue being evaluated. (Need both high k-values for good texture resolution, and high resolution in k-space for sensitive monitoring of pathology-induced changes.) For highly ordered structures one could choose a set of narrow bandwidth measurements distributed over the expected range of texture wavelengths, whereas in a more randomly ordered structure, such as the development of fibrotic texture in liver disease, one could choose to use a single, or a few, broadband k-value measurements to monitor development of the fibrotic texture.

A measure of both the relative intensities of the various textural k-values present in a tissue and the broadness of the peaks along the continuum of textural k-values present within the texture under study is needed. As such, data acquisition can be designed to probe specific region(s) of k-space, with parameter selection that will enable measurement of the relative width of peaks arising from the underlying tissue, rather than that resulting from experiment parameters. It is necessary to recognize the interaction of the two components, and design experiments to yield the best measure of pathology-induced tissue changes.

It is desirable to obtain a good measure of texture by acquiring multiple measures of signal amplitude at specific k-values close in time before motion blurs the data, taking repeat measurements in minimal time to allow best inter-measure correlation for averaging. An alternative to acquiring many repeat measures at one point in 3D k-space, is to acquire data with a gradient on, such that the k-value is changing continuously across the acquisition, the extent in k-space being determined by the height of the gradient and its pulse width. In addition to varying the magnitude of the k-vector, its direction over the course of data acquisition can also be varied. Combination of direction and magnitude changes across an acquisition result in a curvilinear trajectory through k-space. If this deviation is small enough that the k-values remain correlated to some extent, they can be combined more effectively to increase SNR than if they were simply averaged. Gradient on acquisition can therefore be used to intentionally vary the direction and magnitude of the k-vector, for the purpose of smoothing signal speckle—which manifests as a time varying signal over the data acquisition, resulting from interference of the individual spin signals' varying phases and amplitudes. The selected variation in k-value direction and magnitude across the acquisition is chosen to provide sufficient combined measures to get an estimation of the representative power within a neighborhood of k-space.

Varying the k-value to reduce speckle can be accomplished within a single, or multiple, echoes. For a sphere in k-space, defined by the magnitude of the k-value under study, the k-value can be varied by keeping the magnitude of k-constant but sweeping the vector over the surface of the sphere, or the same angular orientation may be maintained, and the magnitude of k varied, or both can be varied simultaneously For the purpose of reducing speckle effects, these variations would usually be small enough deviation from either the k-magnitude or direction that there is a meaningful correlation between the measurements for the particular tissue under investigation.

The major components of the spatial frequency will be the same in all those measurements (they are correlated) unless the measured tissue is a highly crystalline texture. But the normal diffraction pattern for a micro-crystalline or amorphous structure has a lot of speckle. Consequently, by sampling a number of points in the same region of k-space they can be combined in various ways, selected to provide optimal smoothing to reduce the speckle-pattern. A better and more robust measure, from averaging out the fluctuations, is the result.

A number of approaches to "dither" k-value to reduce speckle or to tailor width in k-space may be employed. A first approach employs constant k-magnitude plus sweeping through a range of angles by keeping gradients on during acquisition and combining the measures using correlative information to eliminate speckle. Alternatively, the same direction in k-space may be maintained but the magnitude varied by leaving gradient on during acquisition and combining the measures using expected correlation. As yet another alternative, both magnitude and direction may be varied simultaneously or over an acquisition series, essentially performing the other two alternatives simultaneously to both reduce noise and provide a better assessment of the representative k magnitude in a structure in a "small" region around a specific k-value, i.e., to reduce speckle.)

For combining the measures at different k-magnitudes, for noise reduction averaging, there is a phase shift from one radius (magnitude) to the next from the gradient wind-up. Rephasing may be accomplished before averaging.

Combining the different magnitude measures in an amorphous structure is more well-known than combining different angled measures. Now in addition to the scheme of reducing thermal noise by rapid sampling the fluctuations due to speckle (which though real signal confounds good assessment of the spatial frequency) may be reduced.

A dynamic k-space acquisition is therefore employed. The acquisition mode is dynamically chosen based upon the Signal to Noise Ratio (SNR) of the signal at various k-space locations. The gradient, applied during signal acquisition, post-acquisition receive bandwidth, and estimation algorithms used are dynamically adjusted based upon the expected SNR values in k-space to optimize acquisition time and post-processed SNR. In regions of high SNR, a single sample at a given k value may be a sufficient estimator. This requires a relatively wide receive bandwidth to accommodate the relatively rapid signal variations in the receive chain as k is changed rapidly (due to the large gradient).

In regions of moderate-to-low SNR, the gradient magnitude is decreased so that, subsequent samples, while not taken at identical k values, are correlated, which in turn can be used to improve estimates of the underlying signal values within that range of k-values.

Correlation may be introduced in k-space due to selected windowing in profile space. To enable combination of sequential samples from the ADC so as to improve SNR, correlation among successive samples will be increased by proper choice of windowing in profile space, a shorter window driving a greater correlation distance across sequential values in k-space and a longer window resulting in lower sample to sample correlation. Inducing correlation of neighboring points in k-space by windowing in profile-space is a mathematical tool that can, in many cases, help to measure the underlying texture in a low SNR environment. Basically, windowing blurs the data so that the k-value power spectrum is smeared out through k-space, so that sequential measures can be averaged/combined more easily to increase SNR.

In a very high SNR environment as large a window as possible is used because a measure of the actual textural power distribution across a range of k-space is desired. The longer the sampled region in real (profile) space the more accurate the measurement when measuring amorphous textures. Reducing the sampled region by windowing to induce correlation in k-space actually obscures the specific desired measurement point.

However, while facilitating measurement, inducing correlation through windowing does blur to a greater or lesser degree the underlying relative power density profile in k-space arising from the underlying texture, which is the target of the measurement. As the sample-to-sample spacing (determined by the analog to digital converter speed and gradient height) in k-space decreases, there will be increased correlation, which can be used in post-acquisition processing to form better estimates. Additionally, the receive bandwidth in these regions can be decreased, which further decreases the noise floor.

In regions of very low SNR, multiple acquisitions of the measured signal level at a specific k value can be taken, with zero (and/or non-zero) gradient during acquisition. The multiple acquisitions can then be optimally combined to provide an estimate for specific k values.

Figure 11:
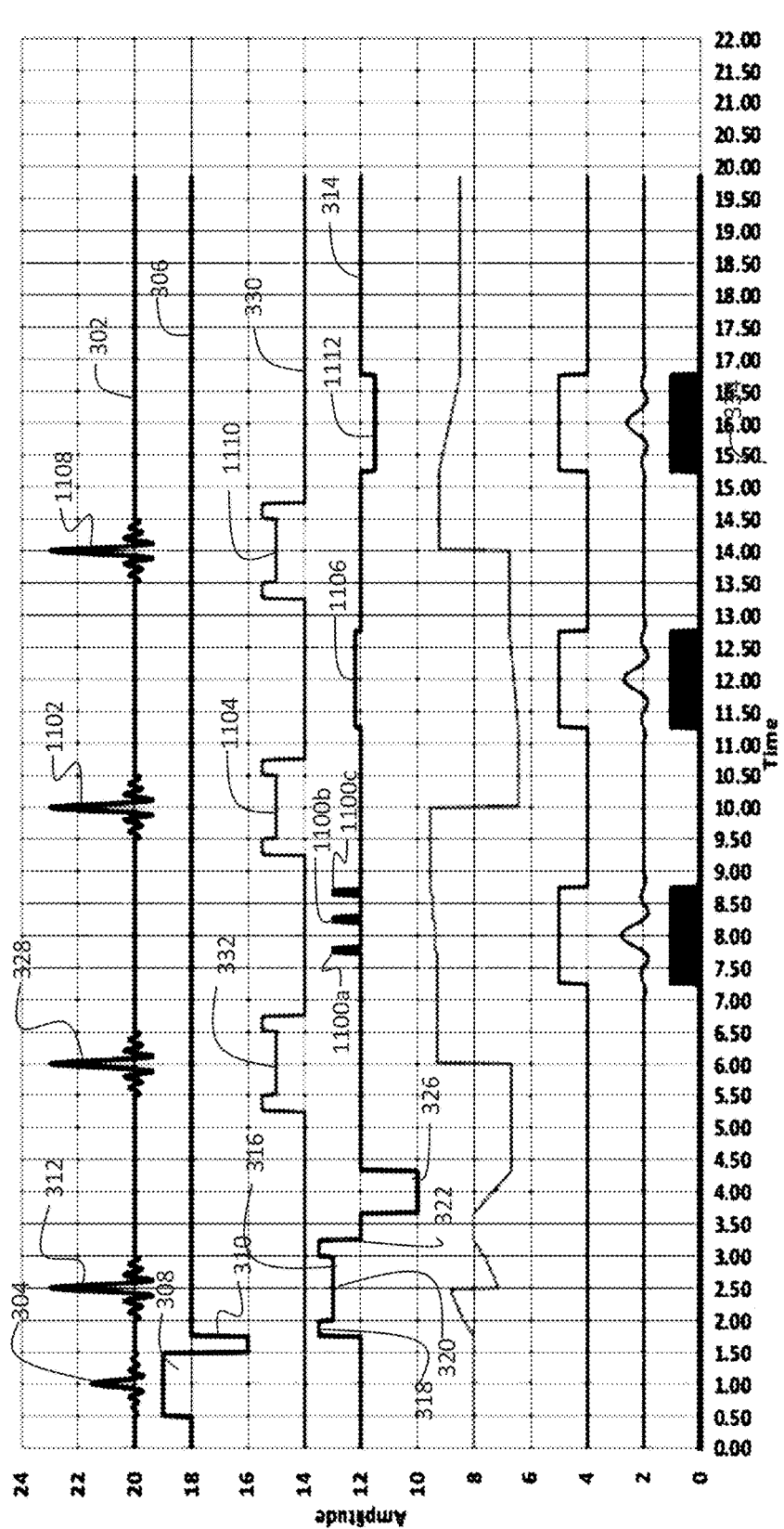
FIG. 11 is an example timing diagram of a pulse sequence for the claimed hybrid method showing the timing of a single TR.

An example Hybrid pulse sequence is shown in FIG. 11. This particular sequence is an example of a rapid acquisition with refocused echoes (RARE) type sequence wherein three different levels of gradient are used for acquisition as illustrated across three separate echoes. The shown pulse sequence for selecting the desired VOI and initial phase wrap for k is as described in FIG. 3 and is numbered consistently in FIG. 11. While this exemplary pulse sequence for establishing the VOI is employed in the various examples disclosed herein, the determination of VOI may be made by any of numerous approaches including, as an example, time varying RF pulses with commensurately time varying gradients applied. Similarly, during or after the pulse sequence employed for determining the VOI, the encoding gradient pulse may be applied for selection of the initial k-value. The data recording starts with acquiring values in regions where |k|>>0, given that the signals are smallest there and should be acquired first. The second echo samples values associated with |k|>0, but whose signal levels are still relatively small and require combination of multiple measures to provide robust SNR. The final echo samples values associated with |k| in the neighborhood near |k|~0 where the corresponding signals are largest. Note that this is just one example of how this hybrid approach, using both zero and non-zero gradient in one acquisition, could be used. Different amounts of k-value windup (as determined by the gradient height and pulse duration) can be acquired in one echo rather than in multiple echoes as will be described subsequently. Multiple combinations of the differing k-value windup also can be acquired within one echo. Additionally, while refocusing is disclosed in the drawings as employing an RF pulse, gradient refocusing may also be employed.

Figure 12:
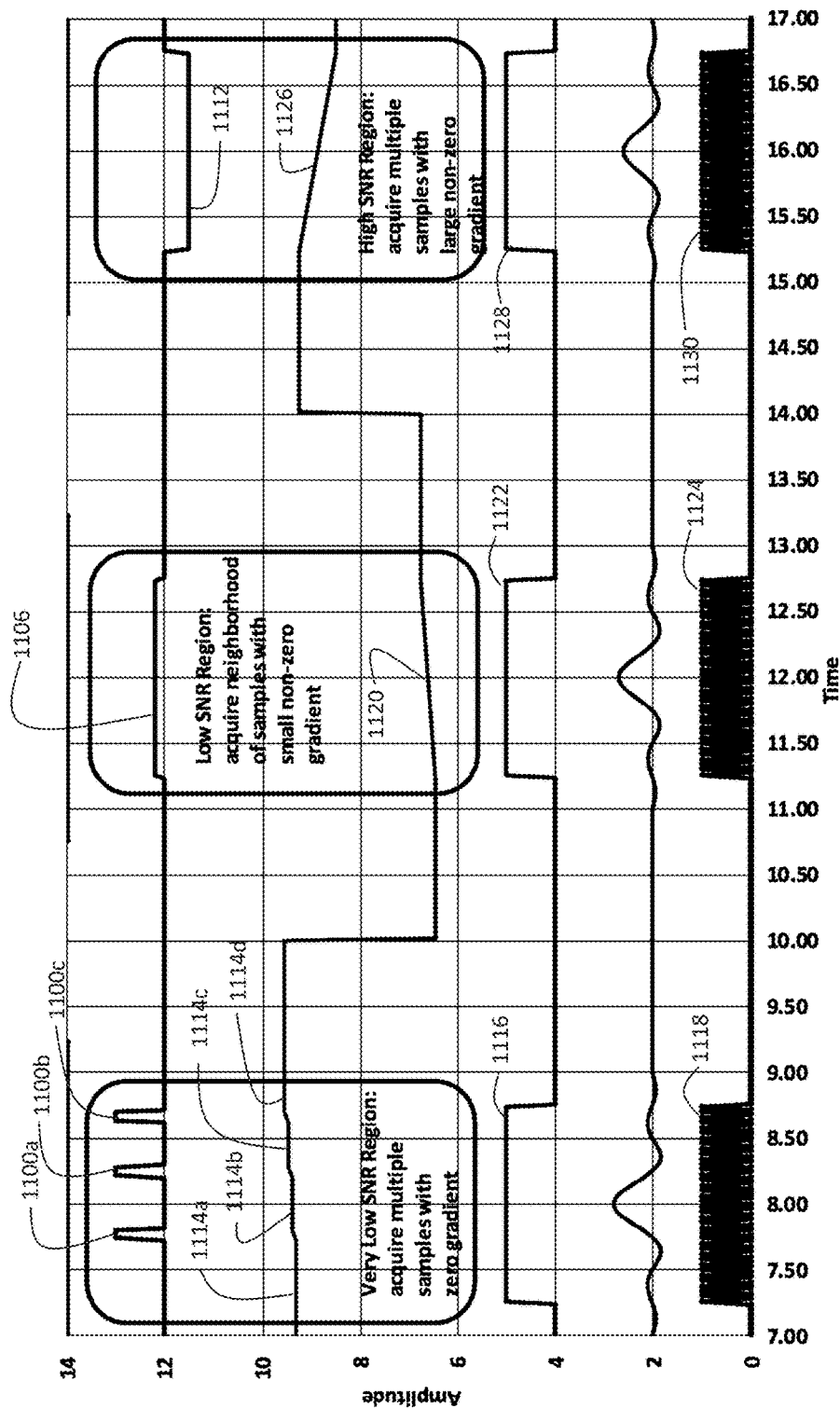
FIG. 12 is a detailed view of the hybrid elements of the method at an expanded scale.

Details at expanded scale of the pulse sequence/signal acquisition are shown in FIG. 12. In this sequence, the first echo from RF pulse 328 with gradient pulse 332 uses the a pulse sequence similar to that previously described with regard to FIG. 3 and acquisition of multiple samples with gradient=0 and incrementing of k values with k value selection gradient pulses 1100a, 1100b and 1100c. This samples multiple values of a given location in k-space, which values are then optimally combined. This is appropriate for regions of k-space whose values are very small and therefore have very low SNR. This typically occurs in regions where |k| is large.

The second echo from RF pulse 1102 with gradient pulse 1104 is acquired with a small non-zero gradient 1106 acting as a time dependent phase encode. A small gradient may be defined as: a gradient that induces samples in k-space which will be sufficiently closely spaced so that the samples are highly correlated. These samples can then be post-processed by an estimator which takes advantage of the high inter-sample correlation to improve the resulting SNR. Quantitatively an exemplary "small" gradient might be up to 20% of the magnitude of the encoding gradient pulse. As seen in the figure samples of multiple values in a relatively small neighborhood, Δk, in k-space are obtained. The spacing of Δk can be chosen such that, due to the windowing of the VOI, there is high correlation between neighboring samples. The correlation is exploited in the estimation algorithm to generate an optimal estimate of the signal levels across a neighborhood in k-space. This is appropriate for regions of k-space which have low SNR, but whose values, because of the correlation induced by the windowing function, vary slowly across k-space in a small neighborhood.

A third echo from RF pulse 1108 with gradient pulse 1110 is acquired with a relatively larger time dependent phase encode gradient 1112. The higher gradient employed herein creates sequential measurements in k-space which have a lower degree of correlation across the neighborhood of k-space under study. In this case, there is lower inter-sample correlation available for SNR improvement. A higher gradient may be employed for sampling k-space locations whose values have a high SNR to begin with (such as would be seen in lower textural frequency (low k-value) regions). As seen in the figure samples relatively widely spaced across k-space, well outside the inter-sample correlation imposed by the window function, are generated over the entire pulse. This is appropriate for rapid acquisition of values in k-space whose signal levels are relatively high and enable high SNR recording. In this case, a single sample at a given point in k-space provides a high enough signal. However, in such higher SNR regions, the higher gradient may be employed and selected bursts of data samples may be rapidly recorded. Each of these bursts will have substantial inter-sample correlation within the burst and may allow computation of results similar to that described for the lower gradient acquisition discussed above. This may be viewed as transitioning along the K-space line with the higher gradient while sampling blocks of data at closely spaced k values to maintain correlation.

Non-zero gradient acquisition allows sweeping across a curvilinear path in k-space. By a judicious choice of time increment, Δt, gradient magnitude, G, w(X), and the total number of samples acquired, N, the neighborhood of "high" correlation can be adjusted to be M<N. This in turn would allow estimation of a multiplicity of distinct values within k-space by using a subset of M samples for each output estimation. Textural data from within a tissue region defined by the VOI can be acquired with the non-zero gradient to enable determination of the local distribution of power density of k-values within a neighborhood in k-space. The extent of k-space sampled with a gradient pulse played out during acquisition is determined by the gradient height and the gradient pulse width (pulse duration). The spacing between signal samples in k-space is determined by the gradient height and the sampling rate (limited by the maximum speed of the analog to digital converter). The correlation between sequential samples in k-space is determined then by the spacing between samples, by subject motion, by the window used to bracket the acquisition in physical space, and by the underlying texture.

A useful method for selecting the acquisition parameters is with reference to the degree of correlation needed within a set of values to be combined. The wavelength of a repeating structure (texture) is defined as the inverse of the k-value associated with that texture, $\lambda_{texture}=1/\lambda_{texture}$. To be able to combine a set of values [measurements] to yield improvement in SNR, the underlying textural signals must not be shifted in phase by a significant percentage of $\lambda_{texture}$ relative to each other. In exemplary embodiments, the phase shift across the set of samples to be combined should be no greater than 80% of $2\pi$.

Resolution in MR imaging is limited by subject motion during image acquisition. This limitation can be very severe with non-compliant patients. In addition to patient motion/compliance, the resolution achievable in MR imaging which is exemplary art comparable to the present invention, depends on several factors, such as tissue contrast, organ, coil type, proximity to coil. Robust imaging of structures below about 5 mm in extent is problematic, and anything below about 1 mm is outside the realm of routine clinical imaging. This is a clear shortcoming as many tissue textures in the range of about 5 mm down to 10 μm develop and change in response to pathology development, hence measurement of these textures can provide much diagnostic information—these tissue changes are most often the first harbinger of disease. It is this textural wavelength range, from about 5 mm down to 10 μm that is targeted with the presently disclosed method.

To measure tissue texture, the range of wavelengths in real space which can be resolved, i.e. the wavelengths of the textures pertinent to the particular pathology, are in the range of several mm down to microns. This is the range made inaccessible (blurred) in imaging due to patient motion. As k is defined as 1/wavelength, a range of k-values from about 0.2 mm$^{-1}$ to 100 mm$^{-1}$ is employed in exemplary embodiments to define the textures of interest. This brackets the region of k-space of interest, and defines the gradient height and duration of the encoding gradient pulse to induce phase wrap to create a spatial encode for the specific k-value and orientation as well as for the non-zero gradients applied for measurement of the neighborhood around the initially selected k-value. The method of the embodiments herein for sample acquisition and post processing may all be conducted in k-space. The only localization in real space is the positioning of the VOI. Just enough of the neighborhood around a point in real-space is sampled to measure texture—i.e. to determine the power distribution within a neighborhood in k-space around the selected point in real space.

The exact range needed varies with the targeted pathology. For example:

Osteoporotic development in bone microarchitecture. As examples, the variation in average trabecular spacing (TbSp) from healthy to osteoporotic bone brackets a wavelength range of about 0.3 mm to 3 mm; the equivalent range of k-values is 0.34 mm-1 to 3.4 mm-1. With fibrotic liver disease monitoring change in liver tissue texture from the healthy collagen-highlighted vessel-to-vessel spacings to the diseased state in which the lobule-to-lobule spacing becomes the prominent tissue texture. Vessel-to-vessel range is 0.4 mm to 1.5 mm translating to k-values of 0.67 $mm^{-1}$ to 2.5 $mm^{-1}$ while lobule-to-lobule spacing of approximately 1 mm to 4 mm, translating to k-values from 0.25 $mm^{-1}$ to 1 $mm^{-1}$. Angiogenic vasculature development around a tumor site typically changes from the healthy vessel texture spacing of around 100 μm; k=10 $mm^{-1}$. Due to its chaotic nature, the spacings in angiogenic vasculature cover a broad range from about 10 μm to 1 mm, or 1 $mm^{-1}$ to 100 $mm^{-1}$. Diagnostic assessment of dementia-related changes to the cortical neuronal spacing involves measuring high k-values, the healthy structure being about 100 μm spacing or k=10 $mm^{-1}$. Variations of about 10-20% of this value, with increasing randomness in structure, mark the disease.

Therefore, the acquisition parameters can be chosen such that (1) the gradient height/duration generates a range of k-encodes spanning the neighborhood of k-space over which it is desired to inspect the power density present in the targeted tissue texture, (2) the samples to be combined must occur close enough in time that there is no significant blurring due to subject motion across the acquisition time of a block of samples to be combined, and (3) the tolerable amount of motion depends on the neighborhood of k-space under investigation (i.e., the wavelength).

Acquisition of textural data from within a targeted VOI with the non-zero gradient enables determination of the local variation of power density of k-values within a neighborhood of the initial k-value in k-space. The extent of k-space sampled at each gradient pulse is determined by the gradient height and the pulse width. Spacing between the samples in k-space is determined by the gradient height and the sampling rate.

These parameters are selected (1) to allow acquisition of sufficient data for combining toward significant SNR improvement, before subject motion can blur the data significantly relative to the texture to be measured, (2) to ensure sufficient correlation across the blocks of k-values from the acquisition to be combined to maintain a SNR≥0.5 dB, and (3) to set the extent of k-space over which the power density of k-values present in the texture is desired.

Blocks of sequential signal samples to be recombined for SNR improvement can be non-overlapping, or overlapping by a selected number of points, or a sliding block used so as to combine, for example, measures 1-4, 2-5, 3-6 and so on as will be described subsequently. Additionally, the number of samples in each block may be varied from block to block across the extent in k-space of the acquisition, this variation in number of samples to be combined being determined by the requirement for sufficient correlation to maintain SNR sufficient to provide a robust measurement. The approximate noise level can be determined independently by several methods well known to the industry including measuring noise in the absence of signal input.

Acquiring data with different magnitude gradients within one echo, TR, or scan may be accomplished with the successive gradient heights being selected to enable best SNR of the combined signal at the various targeted regions of k-space. To enable combination of sequential samples from the ADC to improve SNR, correlation among successive samples can be increased by proper choice of windowing in profile space, a shorter window driving a greater correlation distance across sequential values in k-space and a longer window resulting in lower sample to sample correlation. The window width selected is defined by both the desire for correlation across many samples in k-space, which dictates a shorter window, and the need to sample a sufficient extent of texture in real space to provide robust measure, especially when measuring highly amorphous textures.

Post-acquisition combination of the signals acquired in k-space in blocks, the number of samples to be combined determined by the requirement that the correlation between the individual signals to be combined be sufficient to achieve a SNR≥0 dB (the level of correlation is determined by subject motion, gradient height, sampling rate, window shape, and the underlying texture.)

Use of non-zero gradient acquisition may be employed to intentionally vary the direction and magnitude of the k-vector over a range during data acquisition, for the purpose of smoothing signal speckle—which will manifest as a time varying signal during the data acquisition—that results from interference of the varying phases and amplitudes of the individual spin signals. The selected variation in k-value direction and magnitude during data acquisition is chosen to provide sufficient combined measures to get a an estimation of the representative power within a neighborhood of k-space, with a SNR of 0 dB, where the neighborhood is within 20% of the 3D orientation and magnitude of the centroid of the neighborhood.

Correction for change in k across a set neighborhood created by application of a non-zero gradient may be accomplished by employing proscribed k encodes for a specific set of k measurement. Additionally, correlation within a set of k measurements acquired within a time period and from a selected VOI can be induced by selecting the time period such that the biological motion is sufficiently small that the phase shift in the data induced by patient motion is less than 50% of the wavelength corresponding to the targeted textural k-value range. Alternatively, a windowing function may be selected such that there is sufficient correlation between individual measurements and the set estimate that a desired SNR can be achieved.

Figure 13:
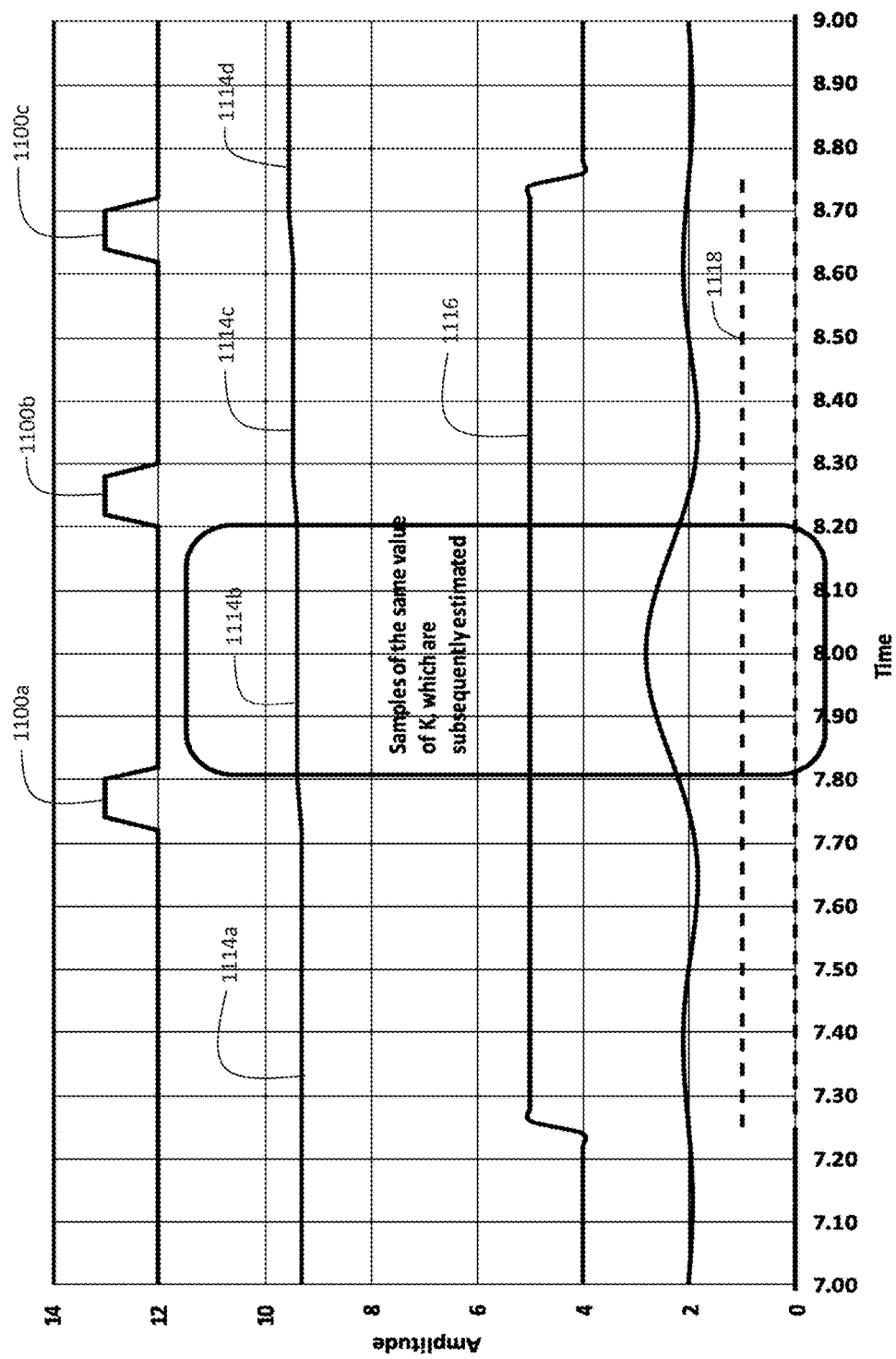
FIG. 13 is a further detailed view of the very-low SNR acquisition mode portion of FIG. 12.

Details of the very-low SNR acquisition mode at even further expanded scale are shown in FIG. 13. In this portion of the sequence, the k-value is constant at an initial value 1114*a*, a second value 1114*b* induced by k value selection gradient pulse 1100*a*, a third value 1114*c* induced by k value selection gradient pulse 1100*b* and a fourth value 1114*d* induced by k value selection gradient pulse 1100*c* in the region 1116 where the sample gate is open thereby producing samples 1118. This is the previously described pulse sequence where multiple repeats of signal at the same k value are rapidly sampled, all of which are then combined into one estimate.

Figure 14:
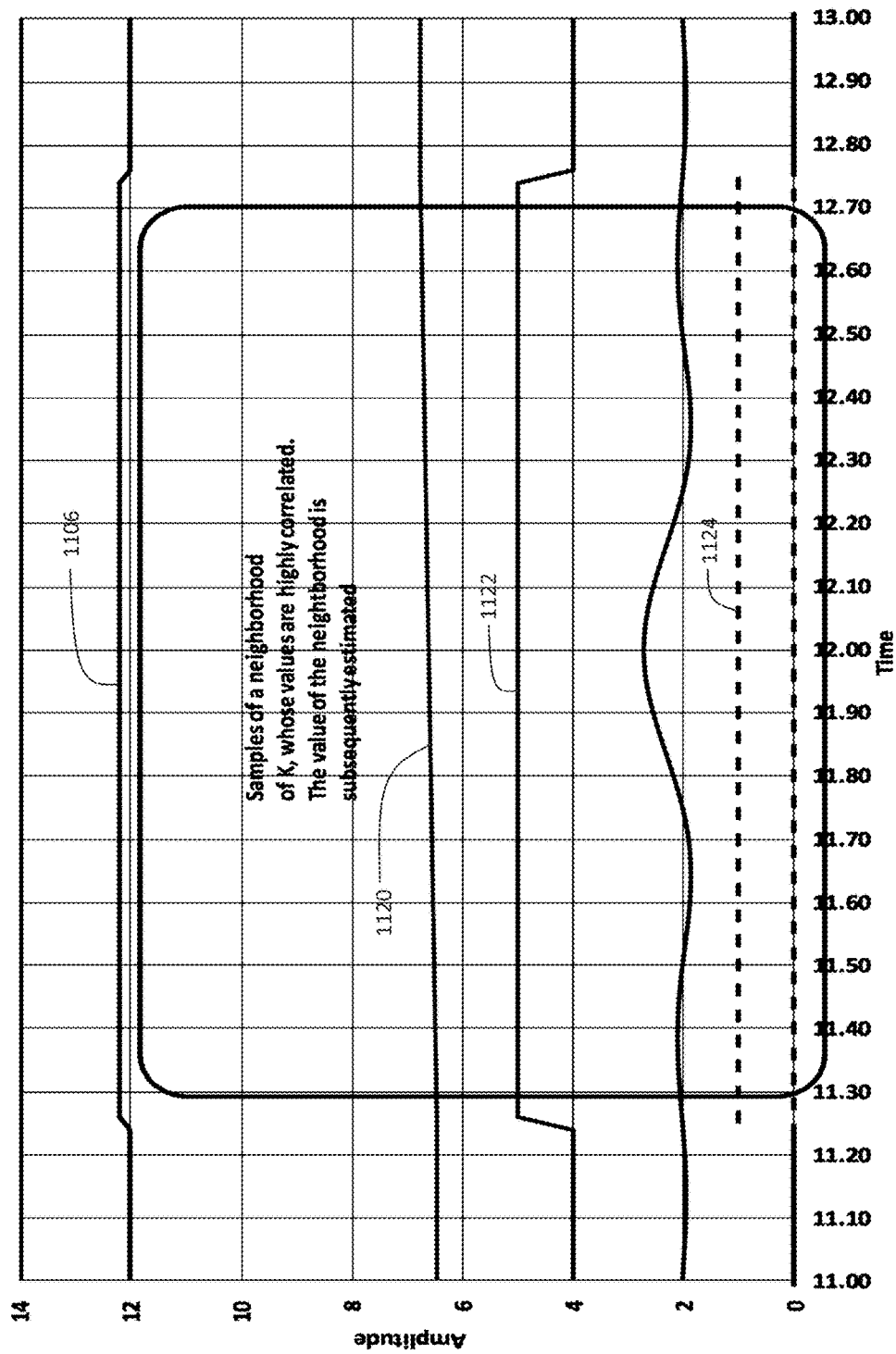
FIG. 14 is a further detailed view of the low SNR acquisition portion of FIG. 12.

Details of the low SNR acquisition at the further expanded scale are shown in FIG. 14. In this portion of the sequence, notice that the k-values do change as shown by trace segment 1120, albeit slowly, due to the non-zero time-dependent phase-encode gradient 1106 present during the recording of the region 1122 when the sample gate is open. However, the range of samples 1124 across k-space is a relatively compact neighborhood where the values are highly correlated due to the windowing function.

Figure 15:
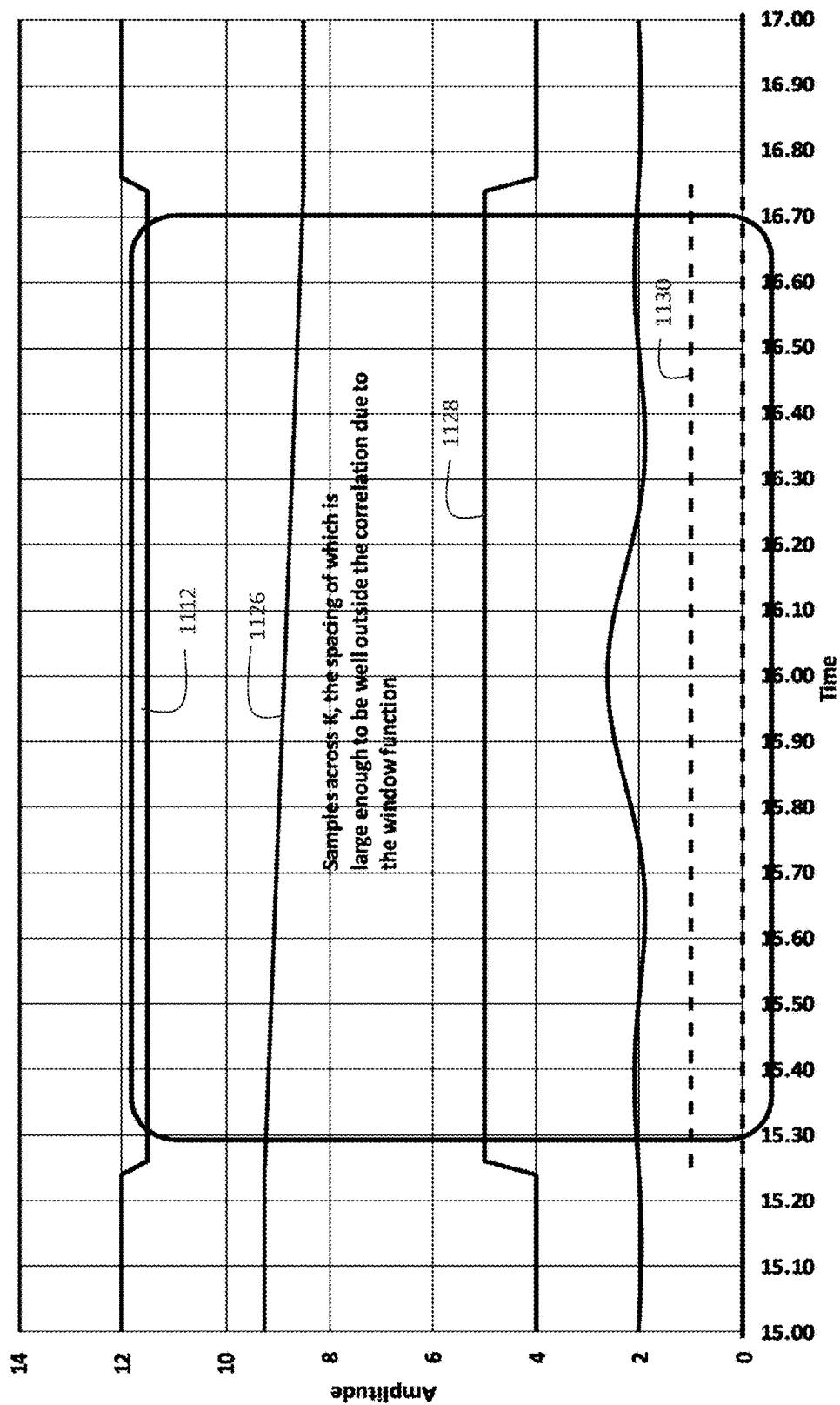
FIG. 15 is a further detailed view of the high SNR acquisition portion of FIG. 12.

Details of the high SNR acquisition at the further expanded scale are shown in FIG. 15. In this portion of the sequence, the k-values again change as shown by trace segment 1126, due to the non-zero time-dependent phase-encode gradient 1112 present during the opening of the sample gate in region 1128. The range of samples 1130 across K-space is still a relatively compact neighborhood, but outside the inter-sample correlation imposed by the window function.

The low SNR and high SNR acquisition modes with non-zero gradient are distinct from a standard frequency-encoded MRI sequence as the applied gradient is not used to establish a position, i.e. frequency encoding, but as a time dependent phase encode to rapidly acquire a number of individual samples across a relatively broader neighborhood of k-space.

Figure 16:
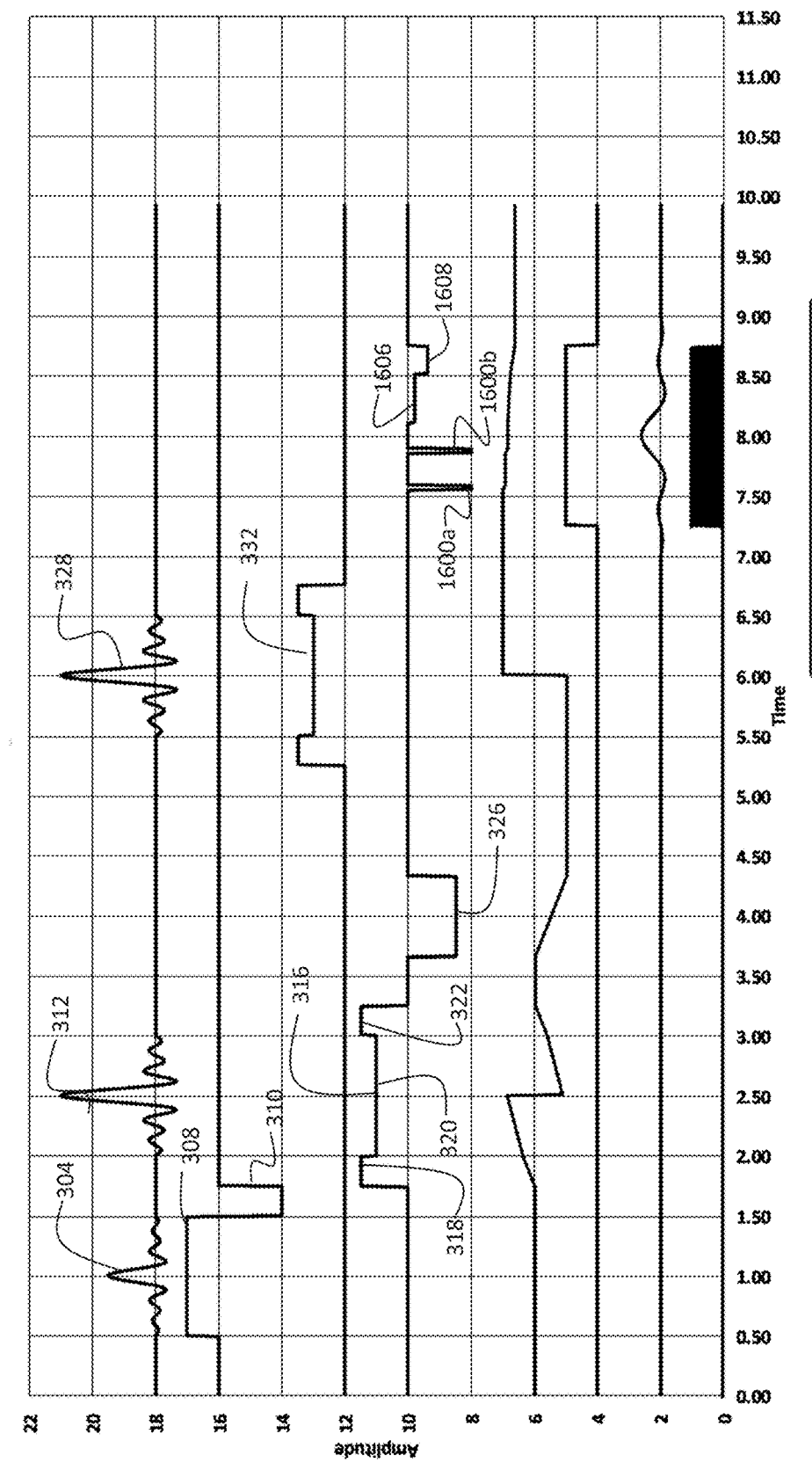
FIG. 16 is an example timing diagram of a pulse sequence for the claimed hybrid method showing data acquisition in a single echo.

As previously asserted, gradient acquisition can be acquired in one echo rather than in multiple echoes as seen FIG. 16. Again the illustrated pulse sequence for selecting the desired VOI and initial phase wrap for k is as described in FIG. 3 and is numbered consistently in FIG. 16.

Figure 17:
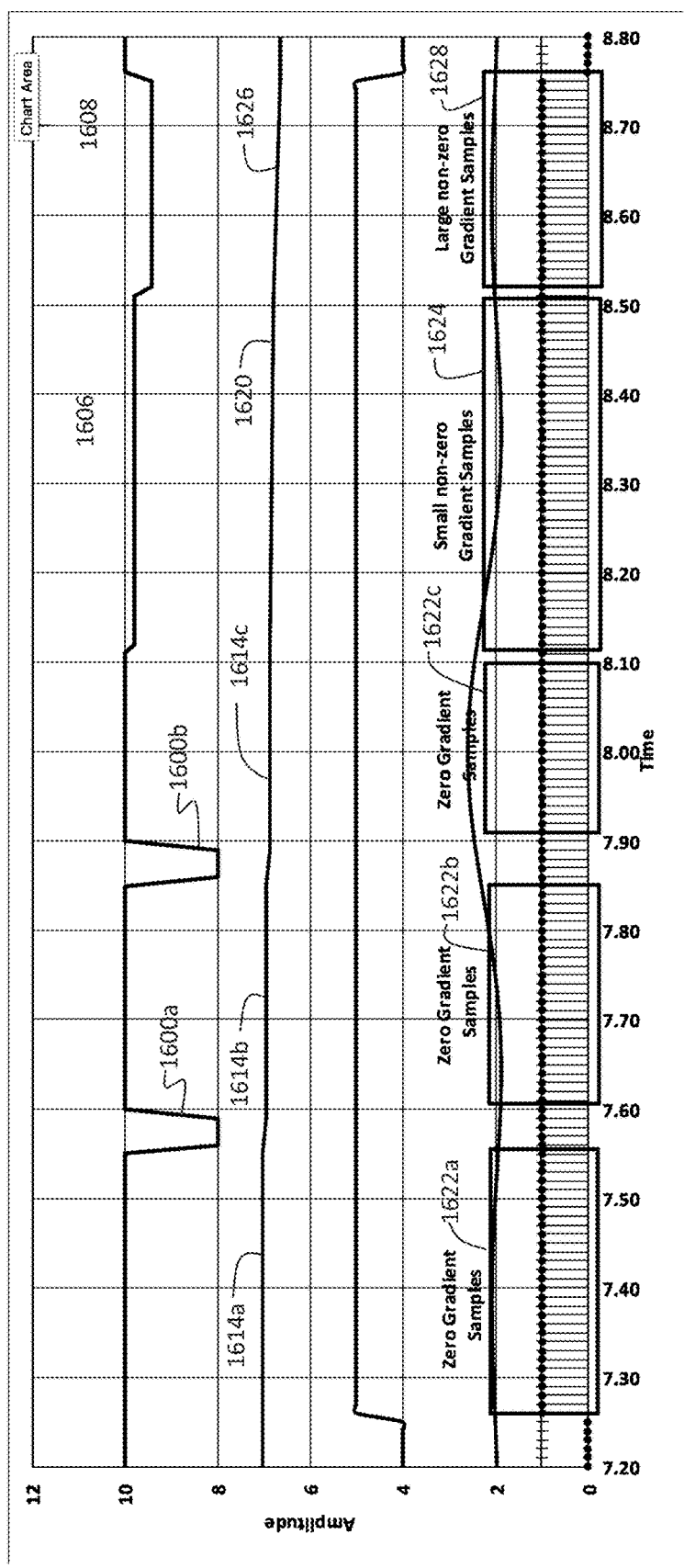
FIG. 17 is a further detailed view of the very-low SNR, low SNR and high SNR acquisition portions of FIG. 16.

As seen in FIG. 16 and at larger scale in FIG. 17, the k-value is constant at an initial value 1614a, a second value 1614b induced by k value selection gradient pulse 1600a and a third value 1614c induced by k value selection gradient pulse 1600b. Note that the k values are decremented as opposed to incremented in the example of FIG. 12. This is again the previously described pulse sequence where multiple repeats of signal at the same K value are rapidly sampled 1622a, 1622b and 1622c, all of which are then combined into one estimate.

In a second portion of the sequence, within the same echo, the k-values do change as shown by trace segment 1620, albeit slowly, due to the non-zero time-dependent phase-encode gradient 1606 present during sampling. However, the range of samples 1624 across k-space is a relatively compact neighborhood where the values are highly correlated.

In a third portion of the sequence, again still within the same echo, high SNR acquisition is conducted. The k-values again change as shown by trace segment 1626, due to the non-zero time-dependent phase-encode gradient 1608 present during the opening of the sample gate. The range of 1628 across k-space is still a relatively compact neighborhood but outside the inter-sample correlation imposed by the window function.

Figure 18:
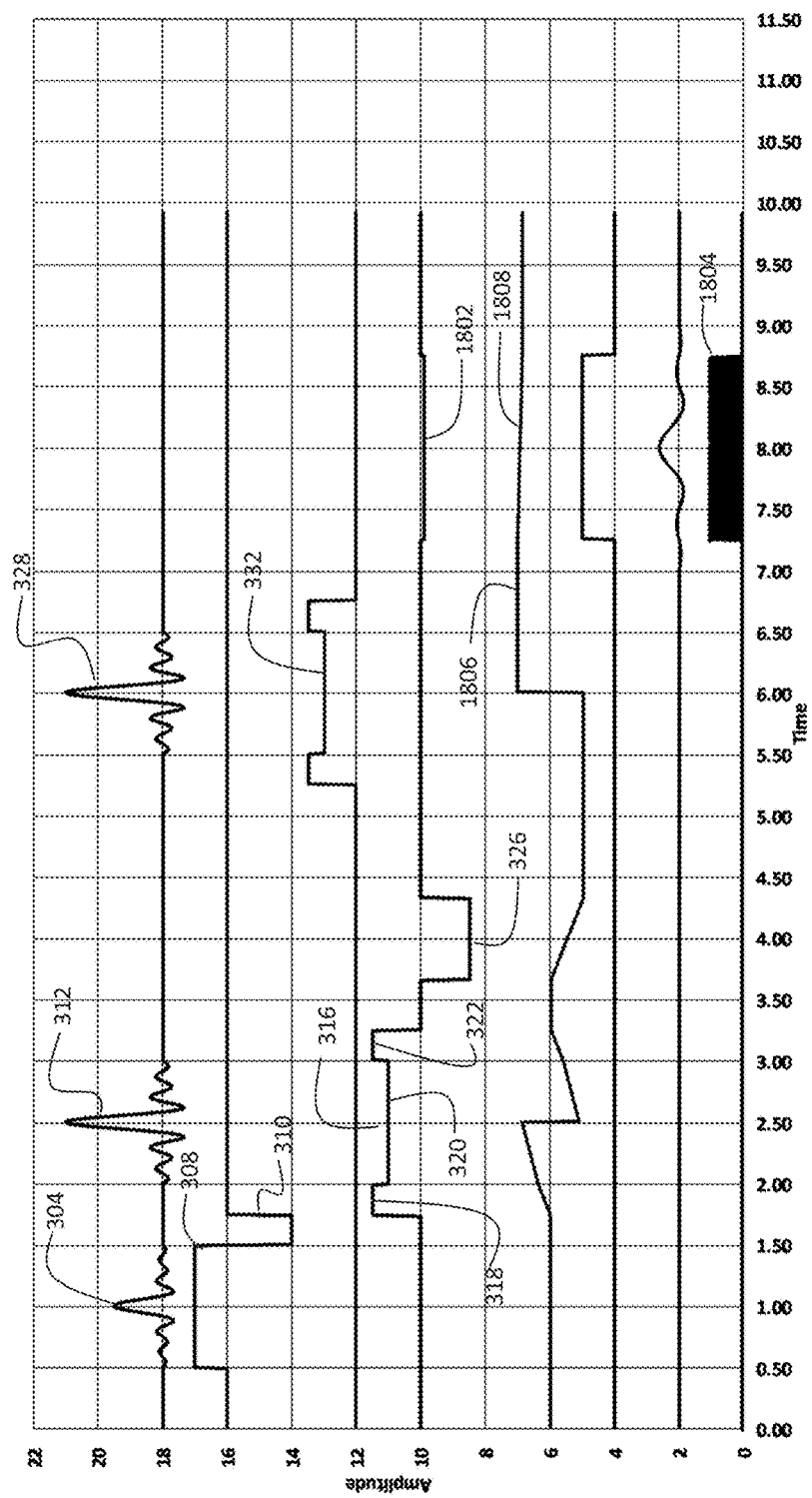
FIG. 18 is an example timing diagram of a pulse sequence for a low SNR acquisition.
Figure 19:
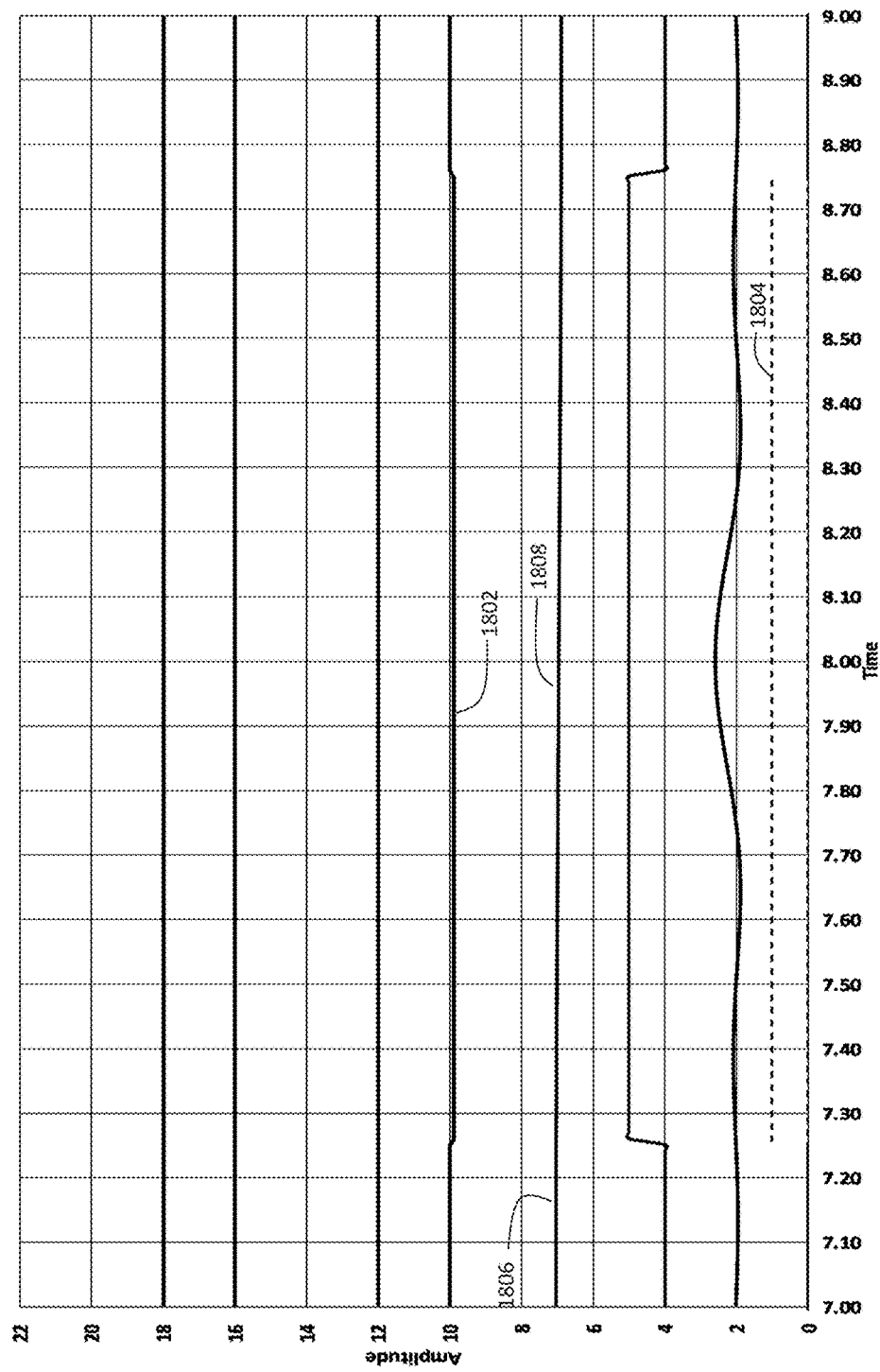
FIG. 19 is a further detailed view of the low SNR acquisition mode of FIG. 18.

As seen in FIG. 18 (and in larger scale in FIG. 19), where the illustrated pulse sequence for selecting the desired VOI and initial phase wrap for k is as described in FIG. 3 and is numbered consistently in FIG. 18, a low non-zero magnitude gradient 1802 acting as a time dependent phase encode is applied and data samples 1804 are taken from an initial k-value 1806 for slowly time varying k-values, seen in trace segment 1808, having high correlation as previously described. The initial phase wrap may be selected to provide an initial k-value with a magnitude corresponding to a low SNR region.

Figure 20:
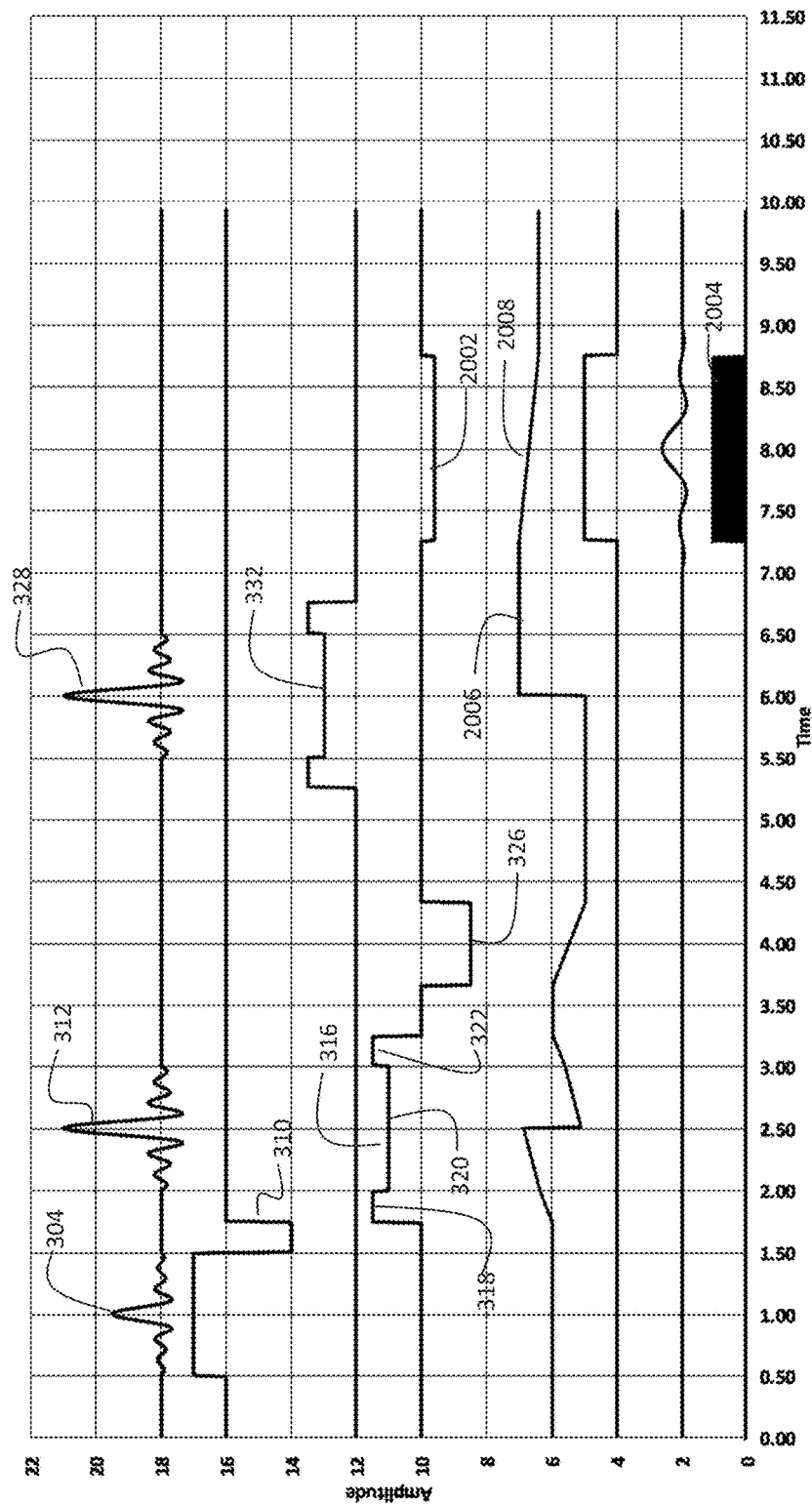
FIG. 20 is an example timing diagram of a pulse sequence for high SNR acquisition.
Figure 21:
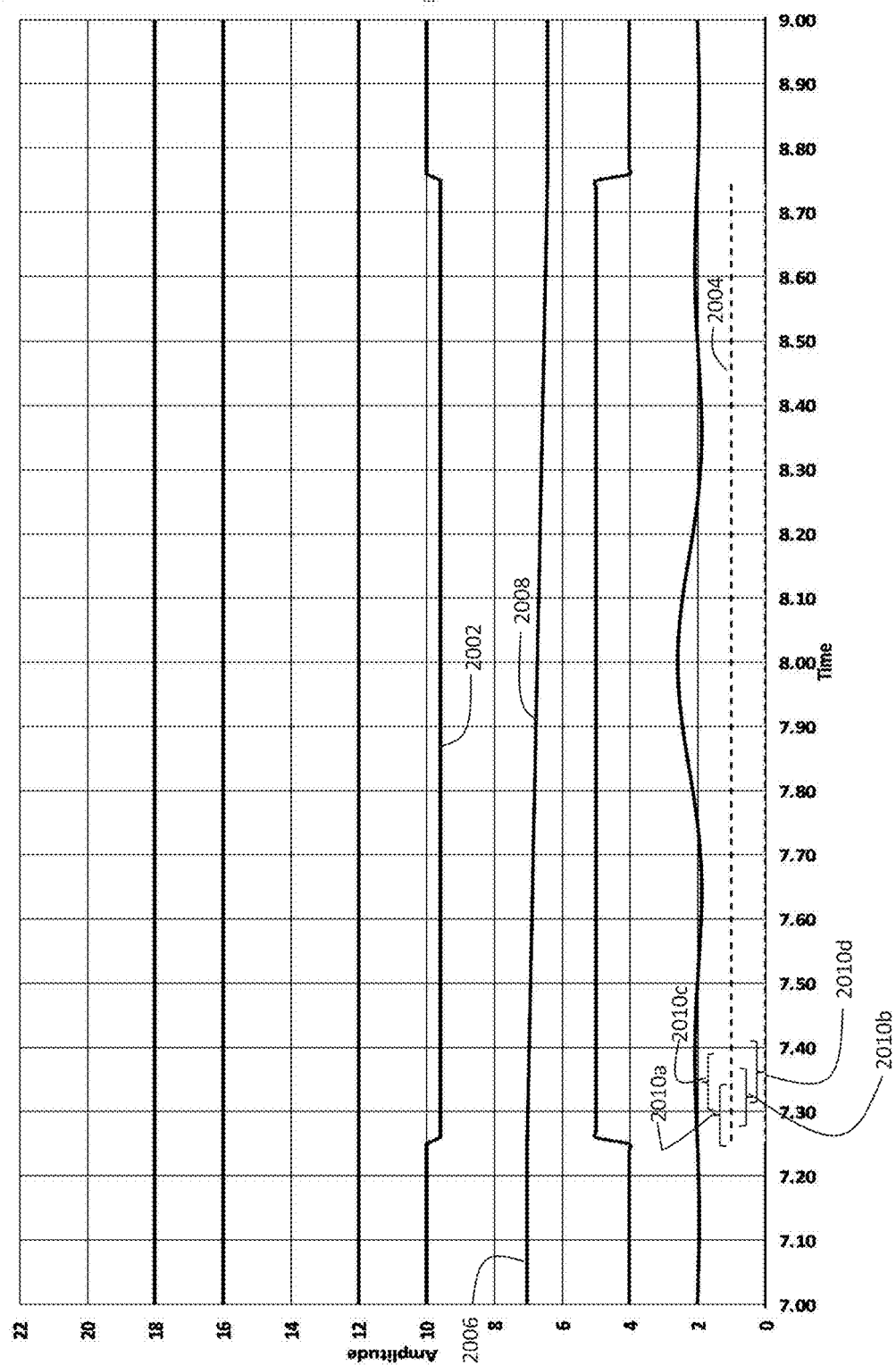
FIG. 21 is a further detailed view of the high SNR acquisition mode of FIG. 20.

Similarly, as seen in FIG. 20 (and in larger scale in FIG. 21), a pulse sequence for selecting the desired VOI and initial phase wrap to set the k-value region is illustrated and is as described in FIG. 3 and is numbered consistently in FIG. 20. A higher non-zero gradient 2002 acting as a time dependent phase encode is applied and data samples 2004 are taken from an initial k-value 2006 for more rapidly time varying k-values, seen in trace segment 2008. The initial phase wrap may be selected to provide an initial k-value with a magnitude corresponding to a higher SNR region. The encoding gradient 326 may be employed to wind up to the lowest or highest k-value in a targeted texture and the non-zero magnitude gradient pulse is imposed in the necessary direction (increasing or decreasing k) to reach the other limit in k-space to define the texture.

The acquired samples may be outside the inter-sample correlation imposed by the window function. However, signal levels for the k-values are relatively large and have high SNR. Additionally as previously described, rapid acquisition of samples in subsets 2010a, 2010b, 2010c and 2010d as exemplary, may be accomplished in a manner that the samples within the subset may remain sufficiently correlated and may provide desired data in structures having predetermined or anticipated texture. One can combine however many sequential values are correlated enough to yield an improvement in SNR via the combination (averaging being one simple form of combining). Then, the set of combined data points is used to characterize the power distribution across the entire acquisition, to get a better measure of the underlying texture within the VOI.

As previously discussed, rephrasing separate low and high k values based on low phase change in a second 90-180-180 excitation (TR). SNR is maximized with gradient ON acquisition by smart combination of successive k-value samples through reregistration of successive acquired signals. Data is acquired across a range of k-space for which the wavelengths are sufficiently long that subject motion can be easily corrected for by reregistration—i.e. the phase shift induced in the measure in this k range is much less than the textural wavelength. The low k-value signal is sampled in alternate refocusing sequences, or sequential excitations (TR), with the acquisition of the signal from the higher k-value range of interest. TE long wavelength measure is used to determine the motion-induced phase shift across the measurements. That phase shift is then applied to the higher k-data prior to reregistration.

A number of correlations are implied by spatial windowing.

If g(x) corresponds to a 1D (real-valued) signal, the corresponding function in K-space is given by the Fourier transform as:

$$G(2\pi k)=\int_{-\infty}^{\infty}(x)e^{-j2\pi\times k}dx \quad (1)$$

Which is frequently expressed as a Fourier pair as $$g(x) \Leftrightarrow G(2\pi k) \quad (2)$$

Windowing is the process of limiting the extent of g(x) to a finite region of compact support, but doing it in such a way to minimize spectral artefacts due to discontinuities (artificially) introduced by the truncation.

Despite the specific shape used of the window function, there is an inverse relationship between the width of the window, and its spectrum. This is due to the Fourier relationship $$h(\alpha x) \Leftrightarrow \frac{1}{|\alpha|}H\left(\frac{2\pi k}{\alpha}\right) \quad (3)$$

Multiplying two functions has the effect of convolving their respective spectra, i.e.

$$f(x):=g(x)h(x) \Leftrightarrow F(2\pi k)=G(2\pi k)*H(2\pi k) \quad (4)$$

The convolution can be thought of as a linear filtering of the spectrum as though the spectrum was the input signal The term $$H\left(\frac{2\pi k}{\alpha}\right)$$

acts like a low-pass filter to the G(2πk) spectrum, which tends to smooth out the signal: the larger the value of α, the narrower the low-pass filter. This creates a significant correlation between adjacent values of F(2πk).

Estimators which observe noisy samples of a filtered input are well studied and can be applied to generate optimal estimates; Weiner filters, Kalman filters, etc.

Dynamic acquisition modes may be employed wherein:
X corresponds to a 3D vector in image space,
g(X) corresponds to the value of the image at a given 3D spatial location,
K corresponds to the 3D vector,
G(K) corresponds to the value in k-space of the image g.

For initial simplicity, the time-dependency of this signal is ignored which in turn depends upon T1, T2, T2*, as well as signal contribution due to differing isochromats (different chemical species within the Volume) etc. In the sequel the effect of these is taken into account Basic Principles relied upon are:
Generally, SNR of G(K) is highest at |k|=0, then decreases with increasing |k|
The rate at which SNR decreases is typically expressed as SNR $\propto |k|^{-\alpha}$ where α is in the range of 1-3.
The sampling rate, combined with the magnitude of the gradient will set the sample spacing (Δk) density in k-space for a given VOI.
As the gradient magnitude is decreased, the sample density increases (i.e. Δk decreases).
Depending upon the size of the windowing in image space, there is a corresponding correlation implied.

For a generalized case the simplified MRI relationship between spatial coordinates and K-space given by $$S(k) = \int\int\int_{i^3} I(r)e^{-j2\pi kg r} dr \tag{6}$$

Where
r represents the real valued 3-Dimensional spatial coordinates with units of meters (m).
I(r) represents the image which is a non-negative Real function of spatial coordinates r.
k represents the real valued 3-Dimensional k-space coordinates with units in cycles/meter (m$^{-1}$)
S(k) represents the Fourier Transform of I(r) and is generally a complex-valued function of k
And the integral is over the entire 3-Dimensional spatial plane.

In words, S(k) represents the corresponding value in 3-dimensional k-space of the image function I(r).

The k-space coordinates, in turn, are a function of time and have the general form $$k(t) = \mathcal{Y} \int_{-\infty}^{t} g(\tau)d\tau \tag{7}$$

Where
$\mathcal{Y}$ is the proton gyromagnetic ratio with value 42.576 MHz/T
g(t) is a real-valued 3-Dimensional function of time representing the gradient strength with units in T/m. This function, is a design input as part of the pulse sequence whose purpose is to manipulate the proton spins in some desired way.

The integral in equation (7) indicates that the value of k(t) for a given value of t, is computed as the integral of all previous history of the gradient function. While technically correct, it is often more convenient to express this as $$k(t) = \mathcal{Y} \int_{t_0}^{t} g(\tau)d\tau + k(t_0) \tag{8}$$

Where now $t_0$ represents a convenient starting time, $k(t_0)$ is the corresponding k-value at $t_0$, and the lower limit of the integral starts at $t_0$.

Making the dependence on time more explicit, equation (6) can be expressed as $$S(t) = \int\int\int_{i^3} I(r)e^{-j2\pi k(t)gr} dr \quad t \geq t_0 \tag{9}$$

S(t) represents the complex-valued baseband signal one might obtain during an MRI echo experiment which is played in conjunction with a gradient sequence encoded in g(t).

Without loss of generality, k, g and r can be decomposed into Cartesian components as $$k=[k_x k_y k_z]^T$$

$$g=[g_x g_y g_z]^T$$

$$r=[r_x r_y r_z]^T \tag{10}$$

And express 9 as $$S(t) = \tag{11}$$
$$\int_{-\infty}^{\infty}\int_{-\infty}^{\infty}\int_{-\infty}^{\infty} I(r_x, r_y, r_z)e^{-j2\pi(k_x(t)r_x+k_y(t)r_y+k_z(t)r_z)} dr_x dr_y dr_z \quad t \geq t_0$$

In general k(t) represents a curvilinear path within K-space as a function of time.

Initially, to facilitate explaining the initial concept, evaluation is confined along a single dimension by assuming $k(t)=[k_x(t)\ 0\ 0]^T$. Equation (11) then simplifies to $$S(t) = \int_{-\infty}^{\infty} \rho(r_x)e^{-j2\pi k_x(t)r_x} dr_x \quad t \geq t_0 \tag{12}$$

Where $$\rho(r_x) = \int_{-\infty}^{\infty}\int_{-\infty}^{\infty} I(r_x, r_y, r_z) dr_y dr_z \tag{13}$$

And equation (8) reduces to $$k_x(t) = \overline{\gamma} \int_{t_0}^{t} g_x(\tau)d\tau + k_x(t_0) \quad (14)$$

Define $$R(k) := \mathscr{F}\{\rho(x)\}(k) = \int_{-\infty}^{\infty} \rho(x)e^{-j2\pi kx}dx \quad (15)$$

Which is occasionally expressed as $$R(k) \Leftrightarrow \rho(x) \quad (16)$$

To concisely indicate that R(k) and ρ(x) are Fourier Transform pairs. By comparing (12) to (15), it can be seen that S(t) is just a time dependent progression across various Fourier coefficients represented by $$S(t) = R(k(t)) \quad (17)$$

Where the mapping between the time-value t and the corresponding K-space coordinate is given by equation (14).

To generally model the receive signal In an actual MRI machine, a combination of the desired signal and noise received by the antenna. That signal is then filtered, amplified, down-converted, sampled, and quantized.

The specific details are machine-dependent, but a simple model can be developed to represent the output of the machine as follows:

Let Y(t) represent a combination of the signal of interest, and a noise signal as $$Y(t) = S(t) + W(t) \quad (18)$$

Where
S(t) is given in equation (17) and
W(t) is a complex-valued zero-mean, Additive White Gaussian Noise Process with variance $\sigma_w^2$, i.e. E{W(t)}=0 and E{W(t)W*(t+τ)}=$\sigma_w^2$δ(τ)

The received signal Y(t) is then uniformly sampled $$Y_n = Y(t)|_{t=n \cdot \Delta t} = R(k(t))|_{t=n \cdot \Delta t} + W(t)|_{t=n \cdot \Delta t} \quad (19)$$

Which can be expressed more simply as $$Y_n = R(k_n) + W_n \quad (20)$$

Where the sequence $k_n$ is given by $$k_0 = k(t)|_{t=0} \quad (21)$$
$$k_{n+1} = k_n + \overline{\gamma} \int_{n\Delta t}^{(n+1)\Delta t} g(\tau)d\tau$$

Define $$\Delta k_{n+1} = \overline{\gamma} \int_{n\Delta t}^{(n+1)\Delta t} g(\tau)d\tau \quad (22)$$

Then Error! Reference source not found. (21) can be simply expressed as $$k_0 = k(t)|_{t=0}$$
$$k_{n+1} = k_n + \Delta k_{n+1} \quad (23)$$

In words, then, the sequence $k_n$ is defined by a sequence of increments which is determined by the integral between samples of the gradient function.

Equations (20), (22) and (23) may be employed to describe the signals under different gradient conditions disclosed herein.

Collecting samples of an echo which has been "pre-phased" through some gradient activity before-hand, but now the gradient is no longer held to zero as described above with respect to FIGS. 12, 14 and 15 can be analyzed as follows.

The signal is then given by equation (20) as $$Y_n = R(k_n) + W_n \quad (24)$$

And $k_n$ is given by equation (21) as $$k_0 = k(t)|_{t=0} \quad (25)$$
$$k_{n+1} = k_n + \overline{\gamma} \int_{n\Delta t}^{(n+1)\Delta t} g(\tau)d\tau$$

Since, measurement is occurring in a non-zero gradient regime, the integral term is no longer zero, which implies that the sequence $k_n$ is no longer constant, and in turn the sequence $R(k_n)$ is no longer constant.

Since no assumptions have been made on the underlying structure of I(r), it cannot be implied that there is any particular structure or relationship amongst the values of $R(k_n)$. This puts us at a distinct disadvantage when wanting to estimate useful signals in a very low SNR environment.

A structure may be imposed on the values of $R(k_n)$ by applying a multiplicative window function in the image domain. This is accomplished by leveraging two Fourier Transform identities:

Multiplication in one domain corresponds to convolution in the reciprocal domain.

Define the following Fourier Pairs:

$$v(x) \Leftrightarrow N(k)$$

$$\rho(x) \Leftrightarrow R(k)$$

$$\zeta(x) \Leftrightarrow Z(k) \quad (26)$$

Then, the product in one domain corresponds to convolution in the reciprocal domain:

$$v(x) = \rho(x)\zeta(x) \Leftrightarrow N(k) = R(k)*Z(k) \quad (27)$$

Scaling in one domain corresponds to an inverse scaling in the reciprocal domain.

If $\zeta(x) \Leftrightarrow Z(k)$ then $$\zeta\left(\frac{x}{a}\right) \Leftrightarrow |a|Z(a \cdot k) \quad (28)$$

Windowing functions are typically used to limit the image space to a finite, compact region of interest, while at the same time, minimizing the adverse consequences on the corresponding image spectrum due to the window itself. Those skilled in the art will appreciate there are a wide variety of window functions which have been developed, each of which have their own particular set of characteristics.

For sake of illustration, consider the most basic window function:

$$rect(t) = \Pi(t) = \begin{cases} 0 & |t| > \frac{1}{2} \\ \frac{1}{2} & |t| = \frac{1}{2} \\ 1 & |t| < \frac{1}{2} \end{cases} \quad (29)$$

The corresponding Fourier transform is given by $$F\{\Pi(t)\} = \int_{-\infty}^{\infty} \Pi(t) e^{-j2\pi ft} dt = \frac{\sin(\pi f)}{\pi f} = sinc(f) \quad (30)$$

which is frequently expressed as the Fourier pair $$\Pi(t) \Leftrightarrow sinc(f) \quad (31)$$

Using equation (28) a slightly generalized version and its Fourier pair is $$\Pi\left(\frac{t}{T}\right) \Leftrightarrow |T| sinc(Tf) \quad (32)$$

Using equation Error! Reference source not found. (27), the windowed profile and Fourier pair is $$v(x) = \Pi\left(\frac{x}{X}\right)\rho(x) \Leftrightarrow N(k) = |X| sinc(Xk) * R(k) \quad (33)$$

Using equation (24) as a reference, the sampled MRI signal can be expressed as $$Y_n = N(k_n) + W_n \quad (3)\ (34)$$

Which, using (33), can be expanded as $$Y_n = \int_{-\infty}^{\infty} |X| sinc(Xq) R(k_n - q) dq + W_n \quad (35)$$

Where the convolution integral has been specifically expanded.

The value of the convolution integral taken at $k_n$ is no longer a function of) just one point of $R(k_n)$. For each point $k_n$ the convolution integral computes a weighted sum of the values of $R(k)$ centered around $k_n$. The extent of the neighborhood in k-space is inversely proportional to the parameter X: Smaller values of X increase the width of the neighborhood in k-space.

For the embodiments herein the extent of the domain of values of interest correspond to the collection of k-space values $k_0$, $k_1$, $k_2$, L $k_{N-1}$. Define $$k_{min} = \min_n k_n \quad (36)$$

$$k_{max} = \max_n k_n$$

Which in turn are functions of the time interval $\Delta t$ and the function $g(\tau)$.

For example, making a simplifying assumption that $g(\tau) = G$ where G is a positive constant, then $k_n$ is just a uniform sampling across a portion of k-space, and is given by $$k_n = k_0 + nG\Delta t \quad (37)$$

Then $k_{min}$ and $k_{max}$ is given by $$k_{min} = k_0$$

$$k_{max} = k_0 + (N-1)G\Delta t \quad (38)$$

While a simple sampling of k-space may be chosen, it is not specifically required. Indeed there could be applications where non-uniform and/or even non-monotonic sampling strategies could be useful.

Ideally, the parameter X (and the window function) are chosen so that the resulting weighted sum across the neighborhood of $k_n$ is "wide enough" so that $N(k_n) \approx C$ where C is a complex-valued constant, but not so wide so as to lose significant spectral resolution For purposes of the disclosed embodiments herein a "small" non-zero gradient may be determined based on selection of desired windowing. From equation Error! Reference source not found. (10)

$$R(k) := \mathscr{F}\{\rho(x)\}(k) = \int_{-\infty}^{\infty} \rho(x) e^{-j2\pi kx} dx \quad (41)$$

Assume that the nominal center point of the profile has shifted to be centered around a point $x_0$. This results in $$R_{x_0}(k) := \int_{-\infty}^{\infty} \rho(x - x_0) e^{-j2\pi kx} dx = e^{-j2\pi kx_0} R(k) \quad (42)$$

Which indicates that each point in k-space is rotated in complex space proportional to the offset $x_0$.

It can be assumed that the gradient is a positive constant, then, by equation (39)

$$k_n = k_0 + nG\Delta t \quad (43)$$

Substituting in Error! Reference source not found. (42) produces $$R_{x_0}(k_n) = e^{-j\theta_0} e^{-jn\Delta\theta} R(k_n) \quad (44)$$

Where the initial phase offset $\theta_0$ and the phase increment $\Delta\theta$ is given by $$\theta_0 := -2\pi k_0 x_0$$

$$\Delta\theta := -2\pi G \Delta t x_0 \quad (45)$$

In the event that, due to the application of a properly specified windowing function, $R(k_n) \approx C$ a complex constant within the neighborhood, the post-acquisition estimator would first multiply an offsetting phase increment $e^{jn\Delta\theta}$ to each acquired sample of $R_{x_0}(k_n)$ before combining and generating the final estimate.

An estimate of $\Delta\theta$ can be obtained from a sequence of k-space samples taken of the windowed profile over lower k-values (where the SNR is higher).

Correlation may be induced by windowing as one parameter as discussed previously. Multiplication of the profile $\rho(x)$ by a real-valued window function $\zeta(x)$ corresponds to convolution in k-space by the Fourier relation $$v(x) = \rho(x)\zeta(x) \Leftrightarrow N(k) = R(k) * Z(k) \quad (46)$$

Z(k) is treated as an impulse response of a linear filter which is applied to the complex-valued signal R(k) in k-space to produce a complex-valued output signal N(k).

The autocorrelation function of the output signal $R_{NN}(\kappa_1, \kappa_2)$ can be expressed as a function the autocorrelation of the input signal $R_{RR}(\kappa_1,\kappa_2)$ and the impulse response Z(k) as $$R_{NN}(\kappa_1, \kappa_2) = \int_{-\infty}^{\infty}\int_{-\infty}^{\infty} R_{RR}(\kappa_1 - \alpha, \kappa_2 - \beta)Z(\alpha)Z(\beta)d\alpha d\beta \quad (47)$$

Equation (47) is inconvenient because the autocorrelation function of the underlying signal $R_{RR}(\kappa_1,\kappa_2)$ is not usually known. A simplifying assumption is made that R(k) is a white-noise, wide-sense stationary process, and express the autocorrelation as $$R_{RR}(\kappa_1,\kappa_2) = \sigma_R^2 \delta(\kappa_1-\kappa_2) \quad (48)$$

With this assumption, (47) reduces to $$R_{NN}(\kappa_1,\kappa_2) = \sigma_R^2 R_{ZZ}(\kappa_1-\kappa_2) \quad (48)$$

Where $R_{ZZ}(\kappa)$ is the autocorrelation function of the impulse response Z(k) and is given by $$R_{ZZ}(\kappa) := \int_{-\infty}^{\infty} Z(k)Z(k+\kappa)dk \quad (50)$$

The mapping of k vs time is mapped as follows.

$$k_n = k_0 + nG\Delta t \quad (51)$$

The normalized correlation $$\eta(NG\Delta t) := \frac{R_{NN}(k_0, k_0 + NG\Delta t)}{R_{NN}(k_0, k_0)} = \frac{R_{ZZ}(NG\Delta t)}{R_{ZZ}(0)} \quad (52)$$

measures the degree to which the underlying sample points are correlated. In low SNR regimes, a high correlation is desired across all of the samples and therefore establish a lower bound:

$$\eta_{min} \le \frac{R_{ZZ}(NG\Delta t)}{R_{ZZ}(0)} \quad (53)$$

Equations Error! Reference source not found. (50) and Error! Reference source not found. (53) provide the defining relationship between the window function impulse response Z(k), the gradient strength G, the sample interval Δt, the number of samples N, and the correlation lower bound $\eta_{min}$.

For example, assume that the window function is defined to be $$\zeta(x) = \Pi\left(\frac{x}{X}\right) \quad (54)$$

Where Π(x) is a standard so-called rectangular function defined below, and X is a constant.

$$\Pi(x) = \begin{cases} 0 & |x| > \frac{1}{2} \\ \frac{1}{2} & |x| = \frac{1}{2} \\ 1 & |x| < \frac{1}{2} \end{cases} \quad (55)$$

The impulse function Z(k) is given by the Fourier transform $$Z(k) = \left|X\right| \left|\frac{\sin(\pi Xk)}{\pi Xk}\right| = |X| \, sinc(Xk) \quad (56)$$

The corresponding normalized correlation function η(κ) is given by $$\eta(\kappa) = sinc(X\kappa) \quad (57)$$

Restricting the correlation to be lower bounded by $\eta_{min}$=0.95 then, by (53) the condition arises that $$\eta_{min} \le sinc(X \cdot N \cdot G \cdot \Delta t) \quad (58)$$

This can be approximated using the first two terms of a Taylor series as $$\frac{\sin(\theta)}{\theta} \approx 1 - \frac{\theta^2}{3!} \quad (59)$$

Which can be inverted and applied to (58) to produce $$N \cdot G \cdot \Delta t \le \frac{\sqrt{3!(1-\eta_{min})}}{\pi X} \quad (60)$$

Which now explicitly expresses an upper bound on the product of the gradient strength G, the sample interval Δt, and the number of samples N.

Typically the sample interval Δt, and the number of samples N are determined by other considerations. Taking these as given, the maximum gradient level is then given by $$G \le \sqrt{\frac{3!(1-\eta_{min})}{\pi X \cdot N \cdot \Delta t}} \quad (61)$$

For a non-zero gradient data acquisition in this case, as long as the gradient G is below the calculated upper bound, the samples acquired will have the defined correlation level. This condition as defined for purposes herein as a "small gradient" level.

Sampling past this limitation will result in lower sample correlation and therefore have less of a potential post acquisition SNR gain. A "higher" gradient may be defined as operating in this condition. Gradient determination is affected by a number of parameters including (1) choice of the window function (e.g. rectangular, Tukey, Hamming, etc.) which influences the shape (and to a certain extent, the width) of the "main lobe" in the impulse response, (2) choice of window extent (the larger the extent in the profile domain, the narrower the "main lobe" in the impulse response), (3) the impulse response which may create an autocorrelation function, (4) the desired level of correlation which determines the effective width in k-space, within which the samples must be contained, and (5) sampling rate*Number of samples*gradient size which determines the actual sampling neighborhood size (note, as long as this number is bounded by the number contained in element (4)) the gradient remains in the "lower gradient level" regime.

An exemplary embodiment maintains a constant ratio of textural wavelength to length of VOI acquisition axis. As the targeted k-value varies, the length of the VOI acquisition axis is varied such that the ratio of the corresponding textural wavelength to the acquisition length remains constant. The aim here is to keep the number of textural "cells" sampled constant. In this way, the differential broadening observed at specific points in k-space, $\Delta k$, is expected to arise from sources other than sampled length in real space, such as the finite width of the RF pulse or the edges of the gradient pulse.

MR-based diagnostic techniques may be combined. Certain MR-based techniques designed to look at very fine tissue structure provide data that may be difficult to interpret in certain pathologies, as they provide only an indirect measure of the underlying structures. Diffusion weighted imaging and Magnetic Resonance Elastography (MRE) are two such techniques. The method of this provisional filing is a direct measure and hence would provide, in many cases, a better measure of fine texture, and in some cases provides complementary data to increase diagnostic capability. Combining acquisition techniques can provide more robust measure of texture, and hence of pathology.

The embodiments disclosed may be used in combination with Magnetic Resonance Elastography (MRE). Currently, the main application of MRE is as a diagnostic for liver disease to determine therapy response, progression, need for biopsy, etc. Though the targeted pathology is fibrotic development, the technique measures this indirectly, through measurement of tissue stiffness. In many cases, it is difficult to distinguish fibrotic development from other stiffness-inducing conditions such as portal hypertension and inflammation. Further, hepatic iron overload, which often results from a compromised liver, will lead to low signal, hence inadequate visualization of the induced mechanical waves.

The embodiments disclosed can provide direct measure of fibrotic development in the liver and, as such, would provide additional data on disease progression or response to therapy in the case of the various triggers of fibrotic liver disease. It provides a local measure within the targeted anatomy for calibration of other, indirect measures, such as MRE, DTI, DWI, etc.

The embodiments disclosed may be used in combination with, or replacement for, diffusion weighted imaging in tumors. The ability to detect the edge of tumors with high accuracy would facilitate accurate surgical removal. Using the embodiments disclosed, data can be acquired in VOIs along a selected direction across a tumor region, looking for the edge of the region of angiogenic vasculature.

The ability to measure inside of tumors to gauge therapy response would help in targeting intervention. As an example of the latter, immunotherapy treatment of melanoma tumors induces swelling of the tumor due to T-cell infiltration which, on a structural MR scan, looks similar to malignant tumor growth. Hence, it is difficult to decide whether to continue the therapy. The ability to look at the state of the vasculature within and surrounding the tumor would enable discernment of whether the growth is cancerous or is due to immune system response. The embodiments disclosed would also provide local calibration of the currently used DTI measures, which are often difficult to interpret.

The embodiments disclosed may be used as a bone degradation measure in oncology. It is well known that radiation and/or chemotherapy often compromise bone health. A measure of changes to bone resulting from cancer therapy would help in tailoring therapy and to determine if there is need for intervention to protect bone health.

Currently, as a follow-on to surgery and treatment for breast cancer, patients are routinely put in the MR scanner to image the breast tissue. The sternum is within the field of view for such exams, enabling easy application of a short add-on sequence of this method to measure changes to trabecular bone and thus obtain a measure of bone health.

As further examples of potential use of the embodiments disclosed in oncology, the embodiments disclosed may be used to measure and quantify hyperplasiac development of mammary duct growth in response to tumor formation and development or to measure and quantify angiogenic growth of vasculature surrounding tumors to stage development, type, and response to therapy. Ongoing treatment after breast surgery often involves reducing estrogen levels, further compromising bone health and, as such, referral for MR scans for bone monitoring is common; use of the method disclosed herein would enable robust and detailed evaluation of bone health by direct measurement of the trabecular bone structure.

The disclosed embodiments are also complementary with Big Data and machine learning schemes. The method disclosed complements the trend towards use of comparison among large aggregates of medical data to learn more about disease, increase predictive power for individual patients and for specific diseases, and note trends across various populations. Benefits of using the method of this filing in conjunction with Big data/machine learning include:

Output measurements from application of the embodiments disclosed can be compared over a population of unknown pathology, for example, the variation in the power spectrum across targeted k-values, could be compared to the occurrence of femur fracture in the same population; the textural power distribution in cortical neuron bundles can be measured and correlated with performance on Alzheimer's mini-mental state exams, MR imaging of brain atrophy, or other assessment of AD or other cognitive pathology; the texture power distribution vs. k-value at various locations in liver can be compared with other inferences of liver disease, such as biopsy, physical exam, blood test, MR imaging, or MRE, over a huge population;

use of machine learning over large populations enables determination of specific biomarkers in pathology;

the ability to make useful correlations using big data and machine learning gets much better with high SNR measure input such as that provided by the method of the embodiments disclosed;

use of machine learning can indicate, for example, if a disease is defined by appearance of a strong signal at a specific k-value appearing in the diseased tissue.

In advance of the macroscopic pathology attendant with disease development, pathological changes occur near the cellular level in affected tissue. For instance, in bone diseases, fracture is often the downstream effect of ongoing progressive thinning of the trabecular elements. In soft tissue diseases, such as liver disease, fibrotic structures develop over a long time in the affected organ, leading eventually to cirrhosis. And in neurology, tissue textures in the brain, in both white and grey matter, change in response to disease onset and progression. The ability to measure the early-stage changes in disease, those affecting fine tissue textures, will enable early stage diagnosis, thus enabling earlier treatment, subject targeting for trial inclusion, and sensitive monitoring of therapy response.

The embodiments herein enable this direct and sensitive measure of disease, through their ability to provide clinically robust measure of the pathologic changes in tissue textures attendant with disease onset and with early-stage progression, providing the needed diagnostic capability.

One of the most valuable features of the disclosed method is that it can be used in conjunction with most contrast methods applied in MRI. As the method results in a texture measurement, as opposed to an image, it needs only to have contrast between the tissue textural elements. This contrast can be generated in many ways, selected to optimize tissue contrast in specific pathologies. The tissue texture measurement yields high spatial resolution due to its high immunity to subject motion. As the acquisition time for the methods previously disclosed herein is short, the textural data can be acquired interspersed with image acquisition in various sequences.

For instance, in bone, for which there is effectively no signal from the trabecular bone elements themselves, a standard T1 pulse sequence, which yields high signal from fat, provides the requisite high contrast between bone and marrow. Thus, the texture measurement employing the methods herein can yield high sensitivity in bone when applied with T1 contrast. T2 contrast can be used to highlight fluid towards determining if a bone lesion is lytic or sclerotic, as there may be little fat remaining around the calcified bone to provide signal. T2 weighted imaging has a host of applications, including abdominal lesion imaging, imaging of iron deposition in the brain, and cardiac imaging, hence use in conjunction with the methods previously disclosed herein enables highlighting of tissue texture in these organs/pathologies.

MRI contrast generation has become increasingly sophisticated over time. In addition to exogenous contrast agents, such as gadolinium, there are the standard T1, T2, T2*, proton density contrast, and Inversion Recovery sequences. Several techniques can be used for fat suppression in imaging. Many new contrast techniques, often dependent on functional contrast, have been developed to highlight different tissues involved in pathology. MR angiography, a method of visualizing vasculature and blood flow, makes use of MR signal saturation, or induced phase contrast in flowing blood, to assess vascular density and permeability. BOLD (Blood Oxygenation Level Dependent) contrast uses metabolic changes in blood to image active brain regions. Diffusion weighting, both DWI (Diffusion Weighted Imaging) and DTI (Diffusion Tensor Imaging), is used to assess pathology in an increasing range of diseases, providing a signal reflective of the microscopic state of the targeted tissue. ASL (Arterial Spin Labelling), traces the diffusion of magnetically-labelled blood (endogenous contrast) through the brain to assess pathology; perfusion imaging is used to assess blood microcirculation in capillaries, another measure of functional response. In both these contrast schemes, the time-course of blood flow, is followed to assess the state of the vasculature near a tumor, as this is a key feature in the diagnosis of gliomas and other tumors. Blood vessels are present in higher numbers within, and surrounding tumors than in normal brain tissue, and they tend to have a larger blood volume. Higher-grade tumors also tend to have higher blood volume, and the degradation and remodeling of extracellular matrix macromolecules results in loss of blood-brain barrier integrity, which is seen as contrast leakage. These measures can capture the degree of tumor angiogenesis, an important biologic marker of tumor grade and prognosis, particularly in gliomas. Application of the methods disclosed herein near the peak of the signal contrast would provide a direct measure of the density and size of blood vessels providing direct measure of the fine-scale vasculature texture as correlational data robustly measuring the degree of angiogenesis within or in the vicinity of the tumor. Combined in this way, a robust measure of pathologic vasculature development for staging neuropathology such as stroke and tumor can be made.

As an example, diffusion weighting in its simplest form, DWI, uses the random Brownian motion of water molecules to generate contrast in an MR image. The correlation between pathology (histology) and diffusion is complex but, generally, densely cellular tissues exhibit lower diffusion coefficients. Obstacles such as macromolecules, fibers, and membranes also affect water diffusion in tissue. Water molecule diffusion patterns can therefore reveal microscopic details about tissue state. By measuring the differential rate of water diffusion across a region of tissue, a map of diffusion rates, reflecting local pathology, can be produced. Diffusion weighting is particularly useful in tumor characterization, vasculature typing, and diagnosing/monitoring cerebral ischemia, among other pathologies. Ischemic infarcts within the brain, abscesses, and certain tumors result in highly restricted diffusion; cysts and edema offer little restriction to diffusion.

Diffusion imaging presents several problems with data interpretation, the most salient of which are: 1) the long diffusion gradients increase the echo time, TE, reducing SNR, 2) the high diffusion gradients required result in eddy currents in metal surfaces in the scanner, which cause signal distortion, 3) the low signal amplitude necessitates use of a relatively large voxel, on the order of 2.5 mm on a side, hence low resolution, 4) the sequence, by design, is highly sensitive to motion, so data recording must be very fast; hence, the ability to increase SNR by averaging signal from multiple acquisitions is limited. Additionally, as at least six different directions are needed to determine fractional anisotropy (FA) the motion sensitivity can lead to difficulty in data interpretation across the course of the acquisition. 5) Interpretation of diffusion weighted signals is not straightforward. The measured diffusion coefficients can arise from many sources, as the exact mechanisms governing water diffusion processes in tissues, especially in the brain, are not clearly understood. What is inferred from the measurement regarding the barriers and restrictions to free diffusion is based on certain assumptions about the underlying tissue pathology. This can take many forms, involving cell membranes, organelles, cell spacing, axon density, glial density, myelin state, etc. 6) Each DWI voxel represents an average, the standard voxel size being on the order of 2 to 2.5 mm on a side. In order to interpret changes in the Average Diffusion Coefficient (ADC) within the voxel, certain assumptions are made, such as tissue homogeneity and type of structure causing the diffusion variation.

The methods disclosed herein entail acquisition within either a single VOI or within multiple, interleaved VOIs, within one TR. Data is acquired without use of a spatial encoding gradient to form an image. This significantly shortens the acquisition time and, combined with the narrowly targeted acquisition in k-space, enables acquisition of the requisite data fast enough to provide immunity to subject motion. Though multiple measures of single volume acquisition can be mapped across the anatomy under study, each measure is acquired rapidly within a single volume. High SNR is assured by this single volume technique as, before motion effects set in, there is time for repeat measure of each targeted k-value; the VOI moves along with subject motion when acquiring data across a single TR. The number of repeats and number of/range of k-values for which data is acquired is limited by the requirement to keep the acquisition fast enough to provide the requisite motion immunity.

The high motion sensitivity of standard DWI, the fact that it is an indirect, or inferred, measure, and its low SNR combine to make it not as robust a measure as would be desired in a clinical setting. Use of the embodiments disclosed herein for data acquisition when using diffusion contrast can mitigate the motion problem as, though the echo time is still long, data acquisition is fast enough that the motion blurring of the signal is minimized. Further, additional data can be acquired by the disclosed methods during the scan, relying on contrast such as T1 or T2 weighting. The standard DWI images, diffusion weighted acquisition by the methods disclosed herein, and data acquired by those methods using contrast, can all be input into a machine learning algorithm, to determine correlation between the measures, and to correlate all three measures against pathology data and outcomes. Though correlation with outcome data takes time, it will provide the best assessment of the capabilities of the embodiments disclosed. Two possible ways to combine the embodiments disclosed with contrast mechanisms, such as diffusion weighting, which, in addition to changing the timing of the elements of a pulse sequence, add extra RF and/or gradient pulses: 1) acquisition of, for example, a diffusion weighted intensity in a single voxel, or in a region mapped by voxels which region is then overlaid by the textural measures obtained using the embodiments disclosed with any other standard contrast weighting, or 2) use the novel contrast mechanism, such as diffusion weighting, to provide contrast for acquisition of the textural measures using the embodiments disclosed. This acquisition can be done in a single VOI or, again, in VOIs across a region of tissue.

Due to the long echo time and sensitivity to patient motion, most diffusion weighting is done using fast Echo-Planar Imaging pulse sequences to provide relatively fast data acquisition. However, chemical shift artifact is highlighted by single shot EPI (around 10 pixels of shift).

Further, as there is not much motion of water through fat, resulting in a bright DWI signal that can obscure lesions, fat suppression is often used as part of the DWI data acquisition.

In one embodiment of the methods disclosed herein described in greater detail subsequently, crusher gradients are used on either side of the 180° gradients to eliminate focusing of noise signal generated during the 180° pulse. Replacing these crusher gradients with diffusion weighting gradients, allows acquisition of both the diffusion weighted signal as well as the subsequent restricted k-value signals. As such, the diffusion weighting would be a measure in the VOI.

DTI (Diffusion Tensor Imaging)—in highly oriented tissues, such as nerves and white matter tracts, diffusion occurs preferentially along one direction, diffusion along the nerve/axon tracts being much preferred to that of the across-track orientation. The degree of directionality, or anisotropy, in tissue is an indicator of pathology, as many neurologic conditions degrade the order of neurologic structures, such as the minicolumns ordering of cortical neurons, or lead to order degradation through demyelination of the axons that form the white matter tracts in the brain. In anisotropic diffusion, the value of the diffusion constant varies with direction. As this anisotropy is a measure of pathology advancement, measurement of the diffusion constant in multiple directions can be used to yield the "fractional anisotropy" arising from the tissue structures and hence provide a measure of pathology advancement. In practice, at least six non-collinear gradients are used to measure fractional anisotropy, leading to a symmetric 9×9 matrix, the "diffusion tensor", the eigenvalues of which yield the major diffusion axes in the 3 orthogonal directions.

Along with using the anisotropy of diffusion to diagnose and monitor pathology in the brain, the diffusion tensor mapped across the brain can be used to delineate the path of white matter tracts. This is called tractography. A possible application of the methods disclosed herein is to measure texture in the white matter tracts affected in multiple sclerosis (MS) using standard T1 or T2 contrast or using the embodiments disclosed in conjunction with diffusion weighting to determine anisotropy of the measure for correlational input for machine learning with standard DTI acquisitions.

The methods disclosed herein provide the ability to obtain tissue texture using contrast that may be applicable to the particular tissue form being examined A contrast is applied using any one of the previously described mechanisms enhancing the contrast between the component tissue types in a multiphase biologic sample being measured. As described subsequently in greater detail, the contrast mechanism and its application may occur at various locations within the NMR inducing pulse sequence. Using pulse sequencing such as that described with respect to FIGS. 3 and 8 a volume of interest (VOI) is selectively excited employing a plurality of time varying radio frequency signals and applied gradients. An encoding gradient pulse, as also previously described with respect to FIGS. 3 and 8, is applied to induce phase wrap to create a spatial encode for a specific k-value and orientation, the specific k-value determined based on anticipated texture of the tissue within the VOL A time varying series of acquisition gradients is initiated to produce a time varying trajectory through 3D k-space of k-value encodes as previously described with respect to, for example, FIG. 8, 11, 16 or 18, with the k-value set being a subset of that required to produce an image of the VOL Multiple sequential samples of the NMR RF signal encoded with the specific k-values are simultaneously recorded. The recorded NMR signal samples are then post-processed to produce a data set of signal vs k-values for the k-values in the set determined by the trajectory.

A first tissue for application of the methods herein is bone. Though the effect on quality of life is huge, no accurate and non-invasive method for sensitive assessment of bone fracture likelihood exists. The current gold standard measure, DEXA, which relies on x-ray absorption, measures areal density of bone. The main determinant of bone strength which predicts fracture, is trabecular microarchitecture, a measure of which is not currently available in vivo. The embodiments disclosed enables this measure.

Bone degradation occurs due to several factors, including disease, cancer therapy, eating disorders, and aging/life style. As trabecular structure erodes in bone, three main morphometric figures vary—the trabecular element thickness, TbTh, the repeat spacing of trabecular cells, TbSp, and TbN, the trabecular number, which is a redundant figure that can be determined from TbSp and TbTh. TbTh decreases continuously with bone degradation. Eventually, as the trabecular elements, or struts, break, there is a discontinuity in the local value of TbSp. Bone degrades anisotropically over time, the anisotropy driven in large part by the effect of load bearing stresses. With progression of bone disease, the TbSp increases faster along the primary load bearing direction than it does normal to this direction, the variation between the two measures being a marker for bone degradation. In addition to the developing anisotropy of bone morphometry, variability in the measure of the trabecular spacing, TbSp, increases, due to the thinning of the trabecular struts to the point where they break, causing discontinuities in the measure of TbSp.

The most definitive measure of bone health is the thickness of the trabecular elements, which is currently impossible to measure directly in vivo, due to the spatial resolution required of the measure.

The embodiments disclosed enable this measure, as it provides the needed resolution for measuring TbTh in thinning trabeculae, down to tens of microns, near the range where the sudden discontinuities in TbSp can then be measured to assess further degradation. As the trabeculae thin to the point of breaking, a sudden shift to increasing TbSp should be visible in the signal distribution vs. k-value, due to the breaking trabecular elements. Additionally, the degree of anisotropy of TbSp can be used as a correlative measure for fracture likelihood Data can be acquired using the embodiments disclosed by positioning the VOI within the targeted bone region, acquiring data within a single TR or across multiple TRs to enable acquisition across the pertinent range of k-values spanned by TbTh and TbSp. Data acquired quickly within one TR can be averaged to improve SNR, the only requirement being that the data is acquired from similar bone tissue.

The requisite contrast is between bone and marrow. T1 weighting provides high signal in marrow, bone offering negligible MR signal. Alternatively, an IR sequence, which results in heightened T1 contrast, can be used. Some work has been done using diffusion weighting to image bone—this is a possible contrast mechanism when using the embodiments disclosed.

Figures 22A, 22B:
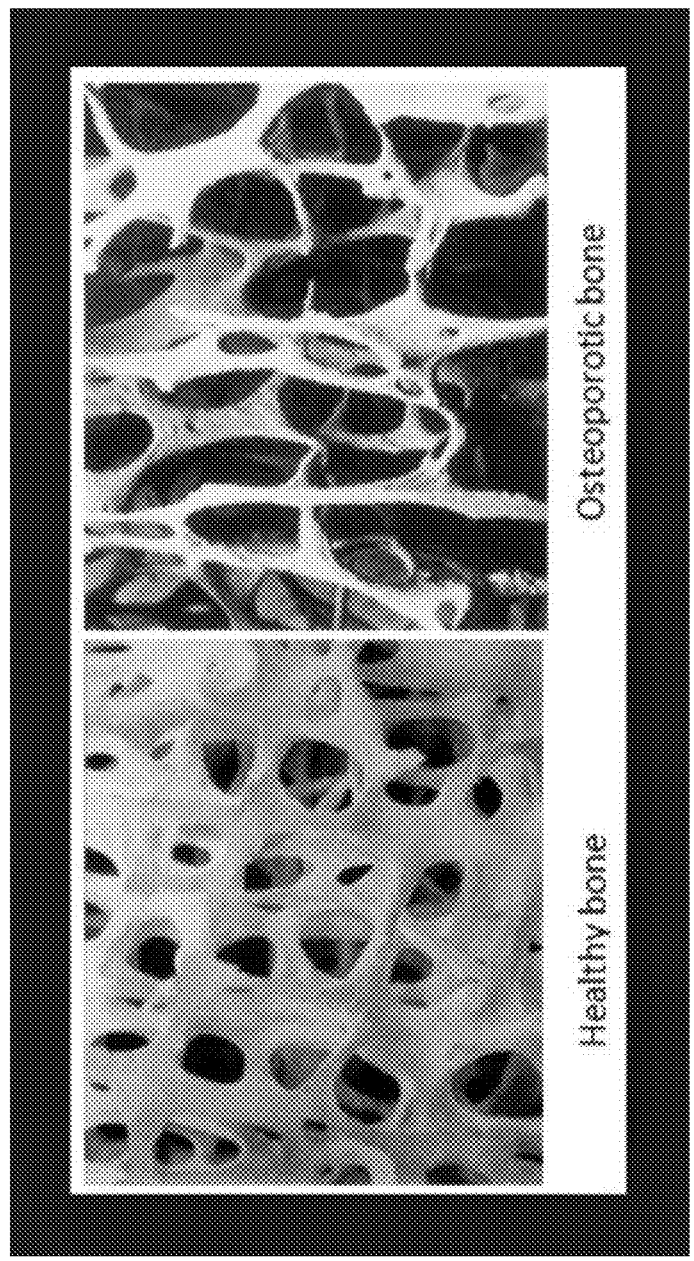
FIGS. 22A and 22B are pictorial representations of healthy and osteoporotic bone structure.

In healthy bone, TbSp and TbTh are closer in magnitude than they are in diseased bone. This can be seen in FIGS. 22A and 22B, by comparing the image of healthy bone, FIG. 22A, with the image of highly osteoporotic bone, FIG. 22B. The exact form of this relationship varies somewhat, the difference in these two morphometric parameters being higher in spine, for instance, than in the hip across pathology. The increasing difference in measure of these two morphometric parameters provides a marker of disease development.

Because of this increasing separation of the two measures, to measure both TbSp and TbTh in osteoporotic bone involves acquiring signal data in two spatially separate regions of k-space. In healthy bone, if gradients are used to select a region in k-space, it may be possible to define a region that encompasses both TbTh and TbSp in the distribution of signal vs. k-value in some skeletal regions. With progressing bone disease the variation in the measured values of TbSp becomes wider, as does the percentage variation of TbTh; additionally, TbSp becomes larger (wider spacing) with disease progression, and TbTh comes narrower. Hence, the center of each of these distributions separates progressively with increasing pathology. Using either gradient on or gradient off acquisition, broadened by gradient height or VOI windowing, or a combination of the two, the general shape of these distributions can be determined. These broadened distributions can be used in real time to determine the regions of k-space to sample more finely in successive TRs.

As desired, data can be acquired using multiple interleaved VOIs within each TR. This method allows determination of the variability in signal at specific k-values within a region of bone. The data acquired from the different VOIs can be mapped, a value/color/icon assigned to signal or peak k-value in the distribution, or to the difference between the k-values associated with, respectively, the peak position of TbTh and that of TbSp. The specific k-value and k-value set established by the time varying gradients may encompass a range of TbSp and TbTh from 0.01 mm to 5 mm in exemplary applications.

The methods disclosed herein can be applied within and around the location of a bone lesion identified with, for example, conventional T1, T2 or proton density contrast, or flow or diffusion contrast MR imaging, to assess the state of the trabecular bone in the region. What is of interest here is a determination of the lesion type; is the lesion indicative of an erosive tumor, or is the lesion in a region of inflammation/degraded bone surrounding a fracture. Some lesions are dangerous and erosive tumors, some lesions are benign. Acquiring data by the embodiments disclosed in multiple VOIs in the area of the lesion would enable a determination of whether the trabecular structure is degraded in the vicinity, and how progressed the degradation is, both spatially and temporally. Further biomarkers can be derived by inputting the MR images of lesions to machine learning algorithms and correlating them with the trabecular data of TbTh, TbSp, TbN, anisotropy and measure variability. By this novel method, the diagnostic content of MR images can be improved, as the appearance of the lesion on the image can be tied to a specific degree of bone pathology.

T2 contrast can be used in conjunction with the embodiments disclosed to highlight fluid in an oncological bone lesion to type it as either lytic or sclerotic. In such pathology there may be little fat/marrow remaining around the calcified bone to provide signal. In an oncologic bone lesion there is usually a mix of fluid, and of marrow in various states of inflammation. To yield a signal from outside the hard bone, proton density can be used. Alternatively, diffusion weighting would return signal based on diffusion of water molecules in the fluid imbued marrow phase.

Use of the embodiments disclosed to acquire signal vs. k-value data in bone, applying the various methods disclosed above, yields several biomarkers for assessing bone health. Measurement of TbSp, TbTh, and TbN in multiple VOIs at different locations in the bone, and with different orientations of the textural encode gradient, yields information on the magnitude and variation of the morphometric parameters, their variation with direction relative to the load bearing axis of the bone, and the variability in the measures locally and across larger bone regions. While, for instance, a measure of TbTh in one orientation locally in advanced disease will clearly reflect pathology, a more sensitive marker for bone health can be derived by combining the sum of the data acquired.

However, correlational data is required for feature/biomarker development or extraction. The highest content predictor of fracture likelihood is fracture history. Bone biopsy is also very sensitive but, as it is a highly invasive biomarker, this procedure is rare. Though DEXA is the current gold standard for bone health, it measures areal bone density, and is not sensitive to trabecular architecture; hence, it is at best a mediocre predictor of fracture likelihood. However, with a large enough sample, this metric can provide increased correlation for diagnostic definition. Taken together, DEXA data and patient fracture history provide a high-level learning framework for correlation with the entirety of the output data derived by the embodiments disclosed, enabling definition of a sensitive diagnostic tool from the embodiments disclosed.

Rather than try to derive biomarkers from the acquired data by individual comparison to look for feature extraction, machine learning algorithms will provide the best correlational data between multiple measurements and, when used in an unsupervised mode, can be compared to extract features from the data for biomarker development.

Further, besides correlation between TbTh, anisotropy data, and measure of TbSp and its variance, fracture data from subjects will be correlated with these measures, also using machine learning algorithms, to develop markers for fracture likelihood. Biomarkers can be derived directly from the signal vs. k-value data by inputting it into machine learning algorithms and correlating it with, for instance, fracture occurrence data from the same patient, DEXA measurements, or bone biopsy report data.

Liver tissue or other tissues subject to fibrotic invasion provide a second example of the use the disclosed embodiments. Although the underlying causes of liver disease are complex and varied, the salient feature of the disease is the development of fibrotic depositions within the liver. Disease onset and progression are marked by increasing accumulation of proteinaceous deposits, mainly collagen fibers, on the hepatic structures. Though fibrotic development can, in the short term, promote healing, if the disease is left untreated, the healing response itself becomes a problem, the excess of proteinaceous substance impeding the normal functioning of the organ. In the case of liver disease, this process, left unchecked, advances to cirrhosis—with attendant carcinoma and/or liver failure. For this reason, diagnosing liver disease early on, when a range of management options are available, is optimal. Use of the embodiments disclosed to assess disease-induced pathologic changes to liver tissue would provide a low-cost, non-invasive, fast add-on to a routine MR exam that would be ordered to check liver health. While the focus here is on liver fibrosis, the pathology, and the application of the embodiments disclosed, is similar to that of a range of diseases characterized by fibrotic invasion. A partial list of these diseases—cardiac fibrosis, cystic fibrosis, idiopathic pulmonary fibrosis, pancreatitis, kidney disease. Additionally, pathologies such as prostate disease, lose proteinaceous deposits in response to disease progression. Though the mechanism is reversed, the tissue texture assessment needed for diagnosis and monitoring is the same.

Though biopsy is the current gold standard for liver disease diagnosis, sampling errors within an organ, significant read errors, and non-negligible morbidity, and even mortality, make this other than an optimal diagnostic. For sufficient statistics, many samples would be required, given the high spatial variability of fibrotic development within the liver; however, only a small number of samples can be taken due to the highly invasive nature of the biopsy technique.

Though what is needed is an accurate assessment of the advancement of fibrosis, currently nothing exists that can measure this directly, aside from pathology. By the time liver disease is diagnosable with liver function tests, ultrasound, or MR imaging, it is well advanced. What is needed is a diagnostic that can track the development of the disease in the early stages, when it is still reversible. Application of the embodiments disclosed to measurement of fibrotic structure offers a direct and non-invasive measure, enabling multisample, longitudinal monitoring of disease onset, progression, and response to therapy.

In liver, as in other fibrotic diseases, collagen accumulates in specific patterns within the organ, "decorating" the underlying structural elements. Liver tissue is composed of a multiplicity of adjoining units, or "lobules", the structure of which is delineated by a central vein, and portal veins that form in a hexagonal pattern around it (see diagram below). As such, in the healthy liver (absence of fibrotic development=F0 stage) the salient dimensions that would appear in a signal distribution of tissue texture feature sizes arise from the spacing between these elements—a range of approximately 0.5 mm to 0.7 mm With disease onset, fibrotic development starts on the portal triads, then progresses, eventually forming bridges linking the portal triads to the central veins (Stages F1 through F3). These bridges enlarge and coalesce, forming islands of regenerative tissue surrounded by fibrotic deposition. In this process, vessel to vessel structural spacing in tissue texture becomes gradually replaced by lobule to lobule spacing (Stages F3 to F4). Thus, a clear marker of disease progression is the shift in distribution of textural wavelengths from shorter to longer wavelength (decreasing k-value), this shift being from about 0.5 mm to about 2 mm, and often longer. As collagen accumulates on the surfaces of the lobules in response to ongoing disease, and even the intra-lobule hepatocytes become decorated, the lobule itself becomes the main textural feature, and the inter-lobule repeat spacing the salient repeat width in a power distribution in k-space. This change happens gradually over the course of disease progression, shifting the power density in textural wavelengths (inverse k-values) from the healthy range out to approximately 2-3 mm feature sizes. The salient textural features involved in this textural wavelength shift are well known from histology studies.

In order to diagnose liver disease in its early stages, the shift of the signal as a function of k-value from that expected for healthy liver to longer wavelengths (lower k-values) indicative of disease onset and progression, can be tracked using the embodiments disclosed. This measurement at a particular point in time along the arc of disease progression and response to therapy, can be made either by acquiring successive samples at individual k-values over the desired range of textural wavelength or, alternatively, a gradient can be applied during data acquisition to span the desired range in k-space. A hybrid combination of these two acquisition methods can also be used.

Contrast between the collagen decorating the various hepatic structures and the underlying tissue can be achieved using either endogenous or exogenous contrast: signal from fibrosis is dark in standard T1 imaging, and can be bright in T2 imaging, due to the large water content in the fibrotic structure. Use of Gd contrast agent shortens T1 such that on T1 weighting the fibrosis shows up bright against the background tissue. Higher contrast makes for a more robust measure. However, although these contrast mechanisms provide contrast between fibrosis and underlying tissue, standard MR imaging is not capable of sufficient resolution to discern the pattern of fibrotic development on the various hepatic structures, which characterizes early stage disease. Patient motion blurs the image, even when using breath-hold imaging or respiratory triggering. Using standard MR imaging, liver disease can only be assessed at the more advanced stages, when the liver may be irreversibly damaged. Though advanced disease is diagnosable, what is needed for therapy justification and response monitoring is early stage diagnosis.

Diverse MR imaging based techniques have been used in assessment of liver fibrosis, besides conventional T1 and T2 contrast with or without contrast agents. MRE (Magnetic Resonance Elastography), diffusion-weighted imaging (DWI), and MR perfusion imaging, can yield some information on liver disease, though none are capable of robust diagnosis in the earlier stages of the disease. A major difficulty with them is that they rely on surrogate markers for fibrotic development. MRE relies on stiffness measurement, perfusion imaging measures blood perfusion parameters, DWI (Diffusion Weighted Imaging) measures the ADC (Apparent Diffusion Coefficient) of water in the liver tissue. These parameters all vary in response to many factors besides fibrotic development, such as inflammation, portal hypertension, steatosis, edema, iron overload, and hepatic perfusion changes. Currently, there is no direct way to measure fibrotic development in early stage disease. By providing the ability to achieve robust resolution at the k-values pertinent for measuring fibrotic development, using standard MR contrast methods, the embodiments disclosed enables assessment of disease state in early stage liver disease.

Figure 23:
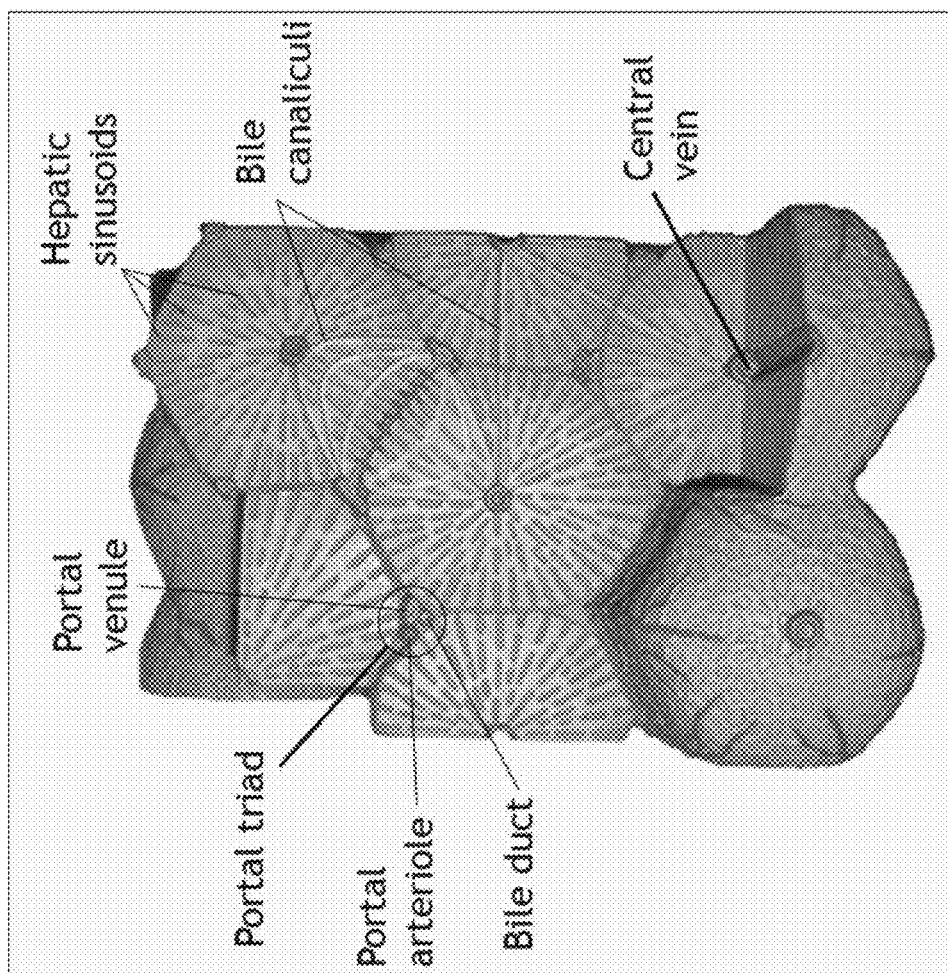
FIG. 23 is a pictorial representation of fibrotic tissue in a liver.
Figure 24:
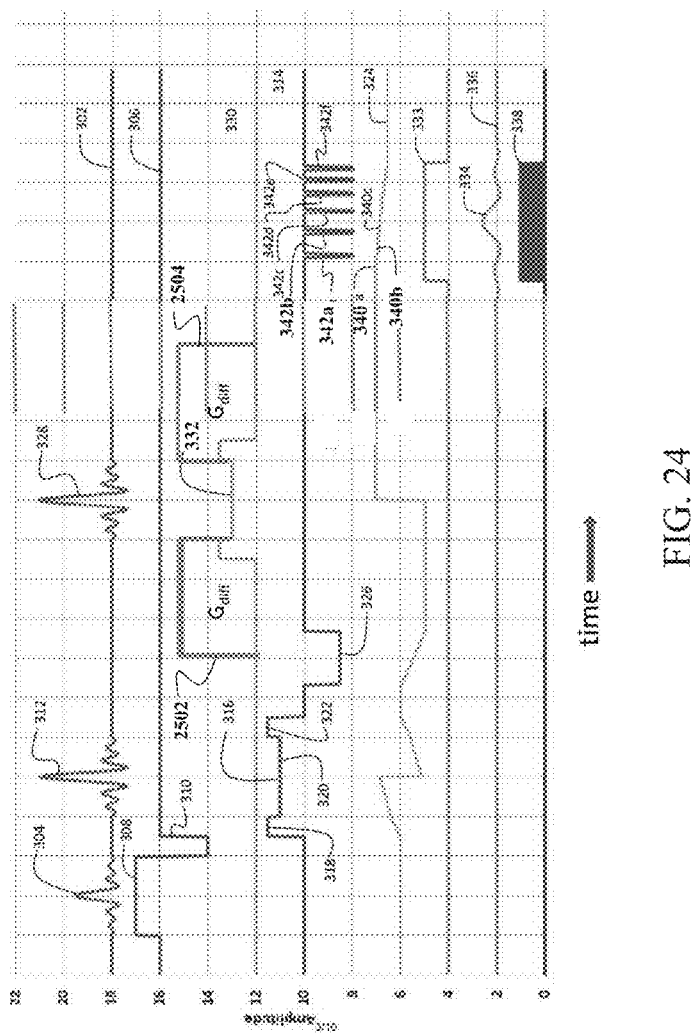
FIG. 24 is an example timing diagram of a pulse sequence implementing a first diffusion contrast.
Figure 25:
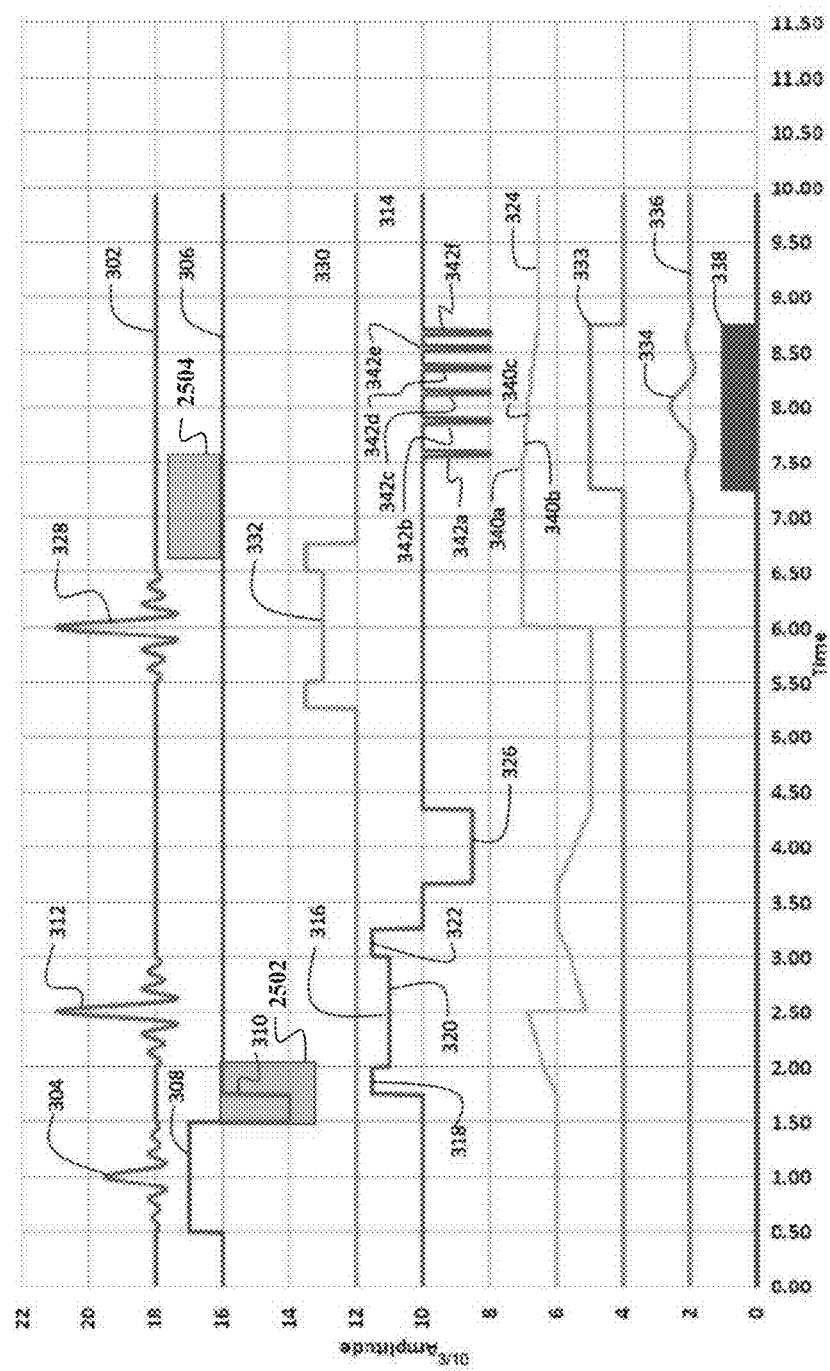
FIG. 25 timing diagram of a pulse sequence implementing a second diffusion contrast.

One of the features of the embodiments disclosed that makes it novel, is that it can be used in conjunction with most contrast mechanisms. One application of this method is its use in conjunction with diffusion weighting, using diffusion-weighted contrast (see FIG. 23 below), but acquiring signal only in the k-value ranges of the fibrotic deposits in early stage disease rather than the entire image acquired in standard DWI. By using the embodiments disclosed for signal acquisition, the data is acquired with a much finer spatial resolution than is possible with diffusion-weighted MR imaging. The texture being measured is on the scale of the fiber-decorated structures, between actual fiber clumps, rather than an averaged measure affected by partial volume imaging. Fibrotic deposition lowers the diffusion coefficient for water, the lower ADC (apparent diffusion coefficient) in areas of fibrosis making for a brighter signal than the surrounding tissue. By using diffusion weighting in conjunction with the embodiments disclosed the structural signal obtained will measure highly localized water diffusion. Hence, as the lobular unit transforms from one with no delineated boundaries to collagen decoration of the hexagonal boundary and then to filling in the entire lobule, water diffusion at the boundaries will be impeded, increasing diffusion weighted signal intensity. As pathology increases, then a textural signature can be obtained by using diffusion contrast. Two approaches to positioning of the diffusion weighting gradients are as shown in FIGS. 24 and 25. The shown pulse sequence for selecting the desired VOI and initial phase wrap for k is as described in FIG. 3 and is numbered consistently in FIGS. 24 and 25. FIG. 24 shows positioning of the diffusion weighting gradients 2402, 2404 on either side of the second 180° slice selection pulse, while in FIG. 25, the diffusion weighting gradients 2502, 2504 are positioned before the first, and after the second, 180° slice select pulses to provide more diffusion time for the same TE than would be available when placing the pair either side of the last 180° slice-selection pulse.

The integrated pulse sequence described with respect to FIGS. 24 and 25 may be repeated with the diffusion gradient applied along multiple axes, similarly to DTI (Diffusion Tensor Imaging). The output dataset would then allow development of a diffusion tensor, enabling determination of the FA (Fractional Anisotropy), a reflection of water flow pathways in the tissue which reflect cellular-level changes.

Figure 26:
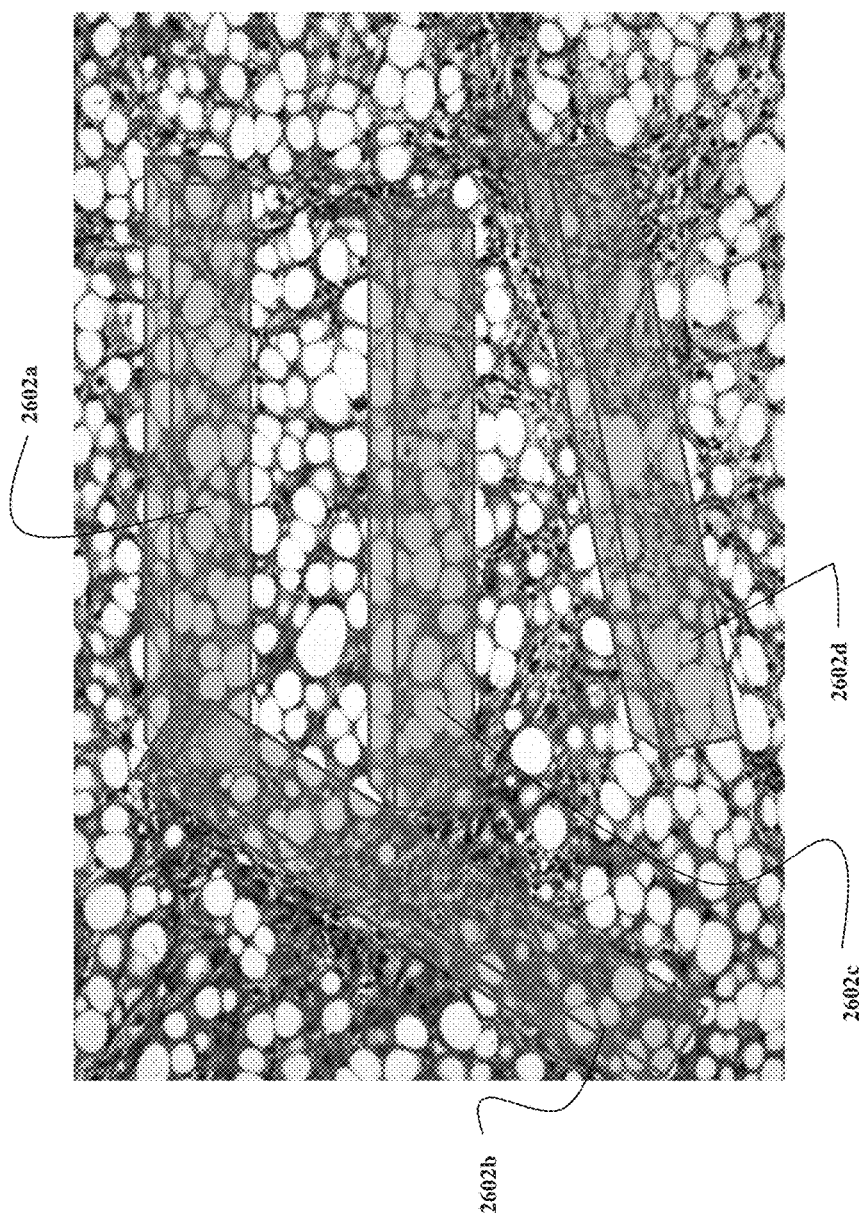
FIG. 26 is a pictorial representation of VOIs dispersed in fibrotic tissue.

Fibrotic texture development can also be assessed using the methods disclosed herein in conjunction with contrast, such as T1 or T2 weighting, with or without exogenous agents such as Gd. By use of localized sampling in both real and k-space, the methods disclosed herein enables fast acquisition of signal at the requisite k-values, enabling robust assessment of pathologic tissue texture at a specific location in the liver—providing a measure of the textural frequencies present at that location, immune from the subject motion-induced blurring that limits current MR imaging methods. Using the methods disclosed herein, the problem of respiratory motion is circumvented by the speed of acquisition of the requisite data. To sample pathology variability within the liver, VOIs $2602a$-$2602d$ can be positioned at various locations in the liver as represented in FIG. 26, using either interleaved acquisition within one TR, or measurements in separate multiple TRs. By use of the methods disclosed herein, texture coherence is maintained within each defined VOI throughout the data acquisition at specific k-values or k-value ranges, so as to enable SNR maximization through signal averaging. If desired, repeat sampling can be made in subsequent TRs at the same location, to obtain an average measure of the degree of fibrotic invasion at that location, for assessment of stage of disease progression. All of the various MR-based measures of fibrotic development in liver disease can be combined with blood-based, biopsy, MRE, physical exam data across a population, using machine learning to both correlate data towards biomarker development for the embodiments herein for textural measure, as well as using machine learning in an unsupervised mode applied to the textural data for feature extraction towards biomarker development.

While the application to liver disease has been called out in some detail here, assessment of other fibrotic diseases is enabled by the embodiments disclosed. Fibrotic development is the hallmark of lung disease (e.g. cystic fibrosis, idiopathic pulmonary fibrosis), myocardial fibrosis, muscle fibrosis, pancreatic fibrosis and kidney disease. Additionally, as mentioned previously, some diseases, such as prostate disease, induce reduction in proteinaceous deposits.

Lung disease diagnosis is stymied by the large range of forms the disease can take, each with a different underlying etiology, prognosis, and required therapy. Idiopathic Pulmonary Fibrosis (IPF) is a chronic, ultimately fatal disease of the lung characterized by progressive decline in lung function. Scarring of the lung and formation of fibrotic tissue in the interstitial lung spaces between the air sacs are the primary injury associated with disease development. The peripheral airways and vessels may also be affected. Diagnosis currently is by ruling out other pathologies, pulmonary function testing, stress tests, blood gas analysis, patient history, in conjunction with imaging using High-Resolution Computed Tomography (HRCT). IPF diagnosis can be confirmed with lung biopsy, but the histology shows striking variation from one region to the next leading to high sampling errors. Further, biopsy is a highly invasive procedure, the tissue insult compounded if there is need for multiple samples.

IPF is believed to be the result of an aberrant wound healing process resulting from repetitive injury of the alveolar epithelial cells. This triggers action of fibroblasts that results in abnormal and excessive deposition of collagen in the pulmonary interstices, forming pockets of "ground glass," fibrotic tissue formation, associated with alveolar degradation. Minimal inflammation is a defining characteristic of the pathology, distinguishing it from COPD.

Histologically, IPF is characterized by the presence of differing proportions of interstitial inflammation, fibroblastic foci, and established fibrosis and honeycombing, all coexisting with areas of normal lung parenchyma. This heterogeneity makes diagnosis by biopsy problematic. Characteristic high-resolution CT (HRCT) findings of IPF include textural changes, including honeycombing, and architectural distortion, involving mainly the lung periphery and the lower lobes. In approximately 50% of cases, HRCT scans are sufficient to allow a confident diagnosis of IPF, obviating lung biopsy. In the remaining 50% of patients, the HRCT findings are relatively nonspecific and may mimic those of other interstitial lung diseases. Souza et al., "Idiopathic Pulmonary Fibrosis: Spectrum of High-Resolution CT Findings", American Journal of Radiology, December 2005

An earlier diagnosis of IPF is a prerequisite for improvement of the long-term clinical outcome of this progressive disease. When treated early, IPF has better outcomes than other forms of interstitial pneumonias. Idiopathic Interstitial Pneumonia can either take the form of IPF, or can be classed under several other forms of pneumonia, with various presentations and prognoses. A major diagnostic need is to differentiate lung disease between IPF and these other forms of lung disease. The ability to more sensitively image lung pathology would enable earlier diagnosis, as well as subsequent therapy monitoring. But the resolution available from Computed Tomography is limited. Even acquisition during a single breath hold is severely compromised by cardiac pulsatile motion and noncompliance to breath hold.

MRI has recently emerged as a clinical tool to image the lungs. Along with enabling tunable tissue contrast and the ability to obtain functional information, it is a non-invasive measure, allowing multiple and repeat measurements. In cases of pediatric imaging, pregnant patients, or for research purposes, the lack of need for ionizing radiation makes MRI the preferred modality.

However, the physical properties of lung parenchyma are very different from those of tissue such as liver or brain. The low density of the tissue, and the susceptibility differences between tissue and air, lead, respectively, to very low signal and to rapid dephasing. This dephasing, resulting from the highly inhomogeneous local magnetic fields at the edges of parenchyma, results in T2* values as short as 2 msec or less, at 1.5T. Thus, the pulse sequences in use rely on GE (gradient echo) refocussing to enable short TE values. However, the short T2* also allows a brief signal acquisition. While this is good from the standpoint of resolution, the recorded signal is low, making MRI of lung parenchyma highly challenging.

CT cannot resolve the underlying structure of the ground glass regions that appear on imaging of diseased lung tissue.

A clear indication of pathology is the appearance of regions within the lung that have a hazy, mottled, appearance, often termed "ground glass" pathology. In some types of lung disease, under the general term COPD, the appearance of this patterning in the lung tissue is associated with inflammation. In IPF, it is associated with development of fibrosis in the alveoli. Though the fine tissue textures underlying the macroscopic appearance in imaging of ground glass regions can help distinguish the various forms of pathology and help set therapy, neither MRI nor CT offer the requisite resolution. This distinction can, however, be made using the embodiments disclosed.

At the microscopic scale, tissue changes associated with inflammation in lung disease are relatively homogeneous within the cloudy patches, showing no spatial texture on the sub mm scale. IPF, however, a disease presentation that usually occurs with minimal associated inflammation, displays at the microscopic scale a mottled textural signature, with a repeat on the order of 0.5-1 mm Though the signal from the fibrotic collagen development that causes this texture is low, contrast between the collagen, which contains fluid, and the underlying lung tissue, which is very low density being mainly air sacs, enables imaging. Hence, as part of an exam workup, the embodiments disclosed can be used as a microscope to reveal the fine textural signature underlying the macroscopically revealed pathologic regions within the lung.

As a non-invasive measure towards determination of lung disease type, the embodiments disclosed would provide data on a scale unachievable through imaging. Combination via AI/machine learning algorithms with current diagnostic measures—pulmonary function testing, stress tests, blood gas analysis, patient history, imaging, and, if applied, biopsy—would enable biomarker extraction from the embodiments disclosed, and calibration of the varying textural signatures embedded in the data set.

Measure of the healthy alveoli using the embodiments disclosed would be difficult, due to the fact that the alveolar walls are on the order of 10 μm, the center of the air sacs generate no signal, and the susceptibility difference at the air wall interface would lead to very rapid dephasing. However, when AI/machine learning algorithms are used to optimize data interpretation, as above, there is a clear chance that the embodiments disclosed could be used for direct measure of the alveoli, and the textural variation inherent in disease progression.

Further, towards diagnosis of lung cancer, the embodiments disclosed can evaluate the state of vasculature in the vicinity of lung nodules, suspected of malignancy. Current use of CT to evaluate lung nodules in high-risk populations has been found in recent analysis to have a false positive rate of over 97%, leading to unnecessary follow-up procedures and concern. Castellino, "Lung Cancer Screening—Benefits Few, May Harm Many", Medscape Jan. 30, 2017.

While the lung moves significantly during free-breathing, and even breath-hold motion is large compared to the very fine textural features that can discriminate disease forms, the embodiments disclosed are immune to this motion, once the VOI is defined. The speed of data acquisition with the embodiments disclosed (<1 minute), combined with the ability to run the method in a free-breathing mode, makes the procedure easy to incorporate in a standard MR lung scan. Wild et al., "MRI of the lung" (⅓), Insights in Imaging 2012.

Given the myriad forms of lung disease manifestation, and the need to distinguish them in order to determine appropriate therapy and monitor response, more information on pathology is needed. While there are several symptomatic level tests, medicine weights highly the variability across CT and MR images. However, the ability to look at tissue changes at the microscopic level, the earliest harbinger of disease onset, has until now not been available. Use of the embodiments disclosed provides such capability.

To obtain the most information from this measurement, diagnostic information obtained by current methods can be used as training sets by incorporating this data in a machine learning algorithm together with the data obtained by the embodiments disclosed. Measures of pulmonary function, stress tests, images, blood gas analysis, patient history, and biopsy, are all suitable candidates, though the main driving element of the learning set is disease outcome when correlated with the new data.

One of the most common histologic features of the failing heart is myocardial fibrosis, diffuse replacement or invasion of the myocardium by fibrous connective tissue. This fibrotic development, which results in wall stiffening, reduced contractility, and impaired overall heart performance, is a significant global health problem associated with nearly all forms of heart disease. Cardiac fibroblasts, an essential cell type in the heart, is responsible for the healthy extracellular matrix. However, upon injury, these cells transform to a myofibroblast phenotype and contribute to cardiac fibrosis, generating excessive deposition of connective tissue in the interstitial space in the cardiac muscle. Fibrosis has been shown to be a major independent predictive factor of adverse cardiac outcome. However, there is a lack of accurate clinical tools to precisely phenotype patients with heart disease.

Assessment of cardiac fibrosis can be made by biopsy and staining techniques. However, biopsy is highly invasive, sampling errors limit its sensitivity, and the entire left ventricle cannot be sampled, hence limiting accurate clinical pathology assessment.

Use of cardiovascular magnetic resonance (CMR) for the non-invasive imaging for patients with compromised heart function has increased over the last decade. The two main methods currently in use are Late Gadolinium Enhancement (LGE) MR and T1 mapping, also based on Gd contrast.

LGE of myocardial fibrosis is based upon the prolonged washout of Gd that results from the decreased capillary density within the myocardial fibrotic tissue. The increase in gadolinium concentration within fibrotic tissue causes T1 shortening which appears as bright signal intensity in the CMR image based on conventional inversion-recovery gradient echo sequences. This provides discrimination between fibrotic myocardium and normal myocardium.

In multi-site clinical use, LGE has absolute signal level problems. Its accuracy for absolute quantitation is limited also due to an over-sensitivity to image settings such as intensity threshold. While currently LGE CMR is the most accurate method to measure myocardial replacement fibrosis, its sensitivity is limited for the assessment of diffuse interstitial fibrosis.

The second MRI measure of fibrotic development is based on the variation in post Gd contrast T1 relaxation times that result from variations in the molecular environment of the water molecules in tissue. Post-contrast T1 values of scarred myocardium are significantly shorter than those of normal myocardium due to the retention of gadolinium contrast in fibrotic tissue. As such, T1 mapping can accurately differentiate pathologic fibrosis from normal myocardium, and can quantify fibrotic development. T1 relaxation times vary significantly from one type of tissue to another, but also within the same tissue depending on its physiopathological status, i.e. whether inflammation, edema, or fibrosis is present in the tissue under study. Hence, mapping of T1 across a region provides information on the spatial distribution of pathology. Specific properties of the target tissue determine the level of T1 shortening induced by the gadolinium contrast agent, generating specific differences in signal intensity.

However, while post-contrast T1 value of myocardial fibrosis is significantly different from that of normal myocardium, T1 distribution can be significantly scattered and this limits its sensitivity for disease states with less severe fibrosis.

Though clinical data to date is scarce, the combined application of T1 mapping with CMR-LGE may help to provide more precise assessment of the heath of myocardial tissue, and to stratify cardiovascular risk in patient populations, detecting subclinical myocardial changes before the onset of serious heart dysfunction. But the shortcomings of these techniques, combined with the recent reticence to inject Gd due to its retention in the brain, make the potential role of the patented method in assessment of myocardial fibrosis timely. The embodiments disclosed can provide the fine tissue characterization that will help improve therapeutic strategies and enable a more direct monitoring of their effect, thus improving clinical outcomes. Such enhanced measure would assist in the search for much needed therapies.

Further, spatial resolution of the amount of cardiac fibrosis in early stage heart disease using MRI is seriously hampered by cardiac pulsation over the time of the measurement. As motion is, unlike Gaussian noise, a non-linear effect, it can't be averaged out—there must be sufficient signal level to allow reregistration before averaging for electronic noise-reduction. A more sensitive (higher SNR), non-invasive technique, capable of assessing textural changes throughout the range of development of cardiac fibrosis, from onset to advanced pathology, is needed to enable diagnosis and monitoring of therapy response. The embodiments disclosed provide this capability Travers et al., "Cardiac fibrosis—the fibroblast awakens", Circulation Research, March 2016; Brønnum and Kalluri, "Cardiac fibrosis: cellular and molecular determinants", Chapter 29 of Muscle, Vol. 1; Konduracka et al., "Diabetes-specific cardiomyopathy in type 1 diabetes mellitus: no evidence for its occurrence in the era of intensive insulin therapy". European Heart J. 2007; Mewton et al., Assessment of myocardial fibrosis with cardiac magnetic resonance, Journal of the American College of Radiology, February 2011

MRI of the heart enables multiple and repeat measurements to track therapy response. Pertinent morphological information, such as wall thickness, edema, scarring of the myocardium, and perfusion (e.g. at rest and during stress) are all macroscopic measures of health. The basic imaging protocols to obtain these measures, such as LGE and T1 mapping, have helped to establish CMR. However, a figure that is missing from current diagnostics is the ability to track the onset and progression of pathologic changes at the microscopic level, specifically the development of fibrosis within the heart.

To provide a much stronger diagnostic for heart disease, the data sets from both techniques can be combined. Use of the embodiments disclosed would allow direct measure of the fine texture signature. While it could be used in conjunction with T1 decay/Gd injection measures, the recent push to eliminate use of Gd may make use of endogenous contrast, such as T1, IR, and diffusion weighting, necessary. T1 mapping data, again using either Gd or endogenous contrast can be compared to the textural measures acquired in multiple VOI positioned to cover the same area as that mapped. Application of the two techniques as interleaved sequences would ensure that the two measures are acquired at the same tissue location. In this way, the textural signal acquired by the embodiments disclosed can be compared with the T1 mapping, enabling determination of both the direct textural measure and the molecular environment, both measures providing assessment of the level of pathologic fibrotic development. The data from the two techniques, along with other measures of cardiac function from physical exams, serum concentrations of collagen-derived serum peptides, as well as quantitative analysis of echocardiograms can together be fed into machine learning algorithm, providing a much clearer assessment of disease progression and therapy results.

Gd-based LGE could provide a third layer of assessment of the developing pathology. For combination with the other diagnostics for optimization of information extraction by machine learning. This combination of techniques, given the high-resolution direct measure provided by the patented method, can provide an enhanced assessment of disease development, enabling therapy response determination and disease prognosis.

Prostate cancer is the second most common cause of cancer death in American men. In current practice, prostate biopsy exams are recommended for men for whom blood tests show high prostate specific antigen (PSA) serum levels, or who demonstrate other symptoms related to prostate dysfunction on exam. Biopsy is painful, risks serious complications such as infection and bleeding, and is diagnostically fraught due to read and sampling errors. The procedure involves twelve needle samples, taken at random from the prostate using trans-rectal ultrasound (TRUS) guidance. Often several tumors of various sizes are present in the organ. Due to the random nature of the sampling, a tumor may not be intersected by any of the needles, making it problematic to quantify aggressiveness of suspected cancer. TRUS-guided needle biopsy misses 25% to 30% of clinically significant tumors because anterior prostate cancer lesions are occluded, making detection difficult until the tumors are quite sizeable. 3 MRI can help avoid unnecessary prostate cancer biopsies, AuntMinnie com Jan. 25, 2017 http://www.auntminnieeurope.com/index.aspx?sec=sup&sub=mri&pag=dis&ItemID=6139 26; 4 El Sevier, Ltd. open access articles, H. U. Ahmed et al., Jan. 19, 2017, http://dx.doi.org/10.1016/S0140-6736(16)32401-1.

Further, the highly invasive biopsy procedure is often prescribed when there is no cancer present—recent research indicates that over a quarter of the men sent for prostate biopsy did not need the procedure. Also, men with no cancer, or with benign cancers, are sometimes given the wrong diagnosis and are then treated even though this offers no survival benefit and has serious side effects. Overdiagnosis and overtreatment have increased in diagnostic practice. A Quarter of Prostate Cancer Biopsies May Not Be Necessary, Xuan Pham, Lab Roots, January 2017, https://www.labroots.com/trending/cancer/5107/quarter-prostate-cancer-biopsies; 2 Imaging Guided Prostate Biopsies Miss Apical Cancer Lesions, Medscape 1/25/17 http://www.medscape.com/viewarticle/874873?src=wnl_edit_tpal&uac=156182MR. As a result, the US Task Force on Preventive Health Care has taken the position that the risk from PSA testing outweighs the benefits. Clearly, additional information is needed here to make the correct diagnoses and avoid unwarranted and invasive procedures and treatment.

Recent studies have focused on the benefit of multiparametric MR imaging (mp-MRI)—scans that use multiple types of tissue contrast—before biopsy. mp-MRI has been found to rule out the need for needle biopsy in as many as a quarter of cases referred for MRI. When it is used in conjunction with medically necessitated biopsy, it can correctly diagnose a high percentage of aggressive prostate cancers, with higher sensitivity than provided by standard transrectal ultrasound-guided (TRUS) biopsy. An inverse correlation exists between Gleason score, a marker of tumor aggressiveness, and ADC (Apparent Diffusion Coefficient, as measured with DWI (Diffusion Weighted Imaging) in MR. In addition, the mp-MRI scans also demonstrate ability to more precisely locate and gauge the size of tumors, improving detection of aggressive cancers. However, it is often hard to distinguish some benign abnormalities, such as fibrosis, prostatitis, and scar tissue from lesions.

While combining mp-MRI with biopsy yields better results than does ultrasound-guided biopsy alone, this is still not 100% accurate. It is required that men still be monitored after their mp-MRI scan and biopsy. Biopsies will still be needed if a later mp-MRI scan shows suspected cancer, but the scan could help to either rule out the need for biopsy, or guide the biopsy so that fewer and better biopsies are taken.

Because of the highly invasive nature of biopsy, as well as its diagnostic shortcomings, prostate care would be progressed if a less-invasive, high information content diagnostic procedure was available. As the additional information provided pre-biopsy by mp-MRI appears to be of clear value, adding high density information to this procedure would be of huge benefit, as the patient is already in the scanner.

Accurate tumor localization and typing within the prostate would enable focal therapies such as cryosurgery, intensity modulated radiation therapy, brachytherapy, or high intensity focused ultrasound to ablate just the tumor rather than having to use a more global therapy. Xu, et al., Magnetic Resonance Diffusion Characteristics of Histologically Defined Prostate Cancer in Humans, Magnetic Resonance in Medicine 61:842-850 (2009).

For a patient referred for mp-MRI, in addition to the basic 3 studies—T2-weighted, diffusion-weighted, and DCE (dynamic contrast enhanced) scan, the embodiments disclosed would be used as described above, to measure the state of the microvessels across the prostate, and to measure the tissue texture through the organ, as this reflects the health of the organ.

Properly implemented, the embodiments disclosed can be used to provide high value diagnostic information towards localizing and typing prostate tumors for size and aggressiveness, while distinguishing them from BPH (Benign Prostatic Hyperplasia), a common pathology associated with aging. This procedure would involve both measuring and mapping the density and form of the microvasculature across the prostate, as an indication of tumor localization and aggressiveness, as well as an assessment of pathologic changes in the prostate tissue across the organ.

Mp-MRI uses typically three different contrast mechanisms—T2 contrast, diffusion-weighted contrast (DWI) and DCE, which follows the time course of the tissue image following injection of an exogenous contrast agent such as gadolinium. Higher resolution measurement of the microvasculature can be provided by using the embodiments disclosed in conjunction with the mp-MRI DCE measure. As data acquisition using the embodiments disclosed is extremely fast, data to map the high-resolution micro vessels across the organ could be acquired as part of the DCE sequence. Additionally/alternatively endogenous flow contrast, such as arterial spin labelling, could be used to provide contrast to the vessels for measure of their volume, density and sizes across the organ.

As discussed previously, one of the features of the method is its ability to be used in conjunction with most any contrast mechanism, thus enabling high resolution measure of the tissue textures brought into relief by the contrast. The speed of the measure, along with the fact that the targeted volume of interest (VOI) can be sized and moved as desired, enables coverage of the entire prostate in a <1-minute exam, allowing assessment of changes in the micro-vasculature and matrix tissue with disease progression. T1, T2, and DWI contrast can be used in conjunction with the embodiments disclosed to provide assessment of changes in the tissue texture across the prostate from the epithelial region and through the stromal areas. This could replace the need for a physical biopsy, providing a non-invasive tissue pathology assessment.

Further capability is provided by use of DTI (Diffusion Tensor Imaging) contrast for which varying the direction of the DWI diffusion gradient allows tracking of directional change in tissue resulting from microscopic changes affecting water diffusion through the tissue. Use of DTI for application of the embodiments disclosed, allows assessment of the anisotropy of tissue changes.

At the microscopic level, normal prostate has a branching duct-acinar glandular architecture embedded in a dense fibro-muscular stroma. In prostate carcinoma, tightly packed tumor cells disrupt the duct-acinar structure leading to the decreased ADC in tumor due to the cellularity induced diffusion restriction. The tissue texture in healthy fibrous tissue has a repeat distance (wavelength) on the order of a few hundred microns, while that in tumors is on the order of tens of microns. Fine tissue texture is also visible in regions of BPH on histology, but the overall patterning is less isotropic and varied in size than that from tumor regions, an anisotropy that can be measured by varying the direction of applied gradients used in the measure. Hence, a clear variation in textural signal is available to differentiate the fibrous tissue to allow diagnosis of cancerous vs. BPH vs. healthy prostate. The embodiments disclosed is the only non-invasive diagnostic capable of directly measuring these tissue variations.

Benign Prostatic Hyperplasia (BPH) has fibrous, muscular and glandular components—the fibrous tissue is laid in irregular patterns, as with the muscular element, giving the appearance of nodularity. The increased cellularity in the region of tumors leads to a lowered apparent diffusion coefficient (ADC), a measure obtained from DWI in the region indicative of development of prostate cancer. If a form of diffusion contrast which highlights anisotropy in microscopic components of tissue texture is used to provide contrast for the acquisition of data by the embodiments disclosed, FA differentiates stromal from epithelial BPH.

Standard diagnosis of disease state is often made by comparison between various diagnostic measures, such as symptoms, serum markers, pathology measures, and patient outcomes. This last figure, patient outcome, is, of course, retrospective. The huge increase in processing capability in today's computers has changed the way this comparison is made, as current electronic storage and processing capability enable more detailed comparison among multiple diagnostics. But, more than just using the various diagnostic measures towards a more robust diagnosis, the ability of computers can enable maximum extraction of data from new diagnostics through use of machine learning techniques. In applying the embodiments disclosed to prostate disease, rather than trying to extract biomarkers as specific features from the power spectrum obtained as characteristic of the vessels and surrounding tissue in the organ, the highest information content can be obtained from the data by using the entire data set. Anecdotal notes on disease progression and outcomes, along with diagnostic data obtained from the mp-MRI scans, can serve as a training set to "teach" a machine learning computer algorithm to assign a diagnostic meaning to the data obtained by the embodiments disclosed, stage disease and diagnose disease progression and aggressiveness. Computers are more capable of making the comparisons, depending on the huge amount of information contained in the various data sets to draw conclusions and stage disease. By this method, the maximum amount of information can be extracted from the data.

Given the tissue variability across the prostate from the epithelial to the stromal region, and locally due to developing pathology/tumors, use of the disclosed embodiments as a diagnostic such that it covers most of the prostate is best poised to assess the health of the organ. Hence, the workflow to provide this disease diagnosis and to track progression would look something like:

Patients that are in for mp-MRI because of symptoms or PSA testing indicating suspicion of prostate disease would also be scanned using the embodiments disclosed in conjunction with various contrast techniques.

Scout images as described herein may be employed for preliminary assessment and calibration.

The embodiments disclosed would be used to measure microvasculature—density, volume, and vessel size, in stepped VOIs across the prostate, using the exogenous contrast used for mp-MRI, interspersing this measure with the time course imaging acquisition done as part of the mp-MRI, or using endogenous contrast such as ASL, to provide contrast for measure of vasculature.

If the exogenous contrast used in mp-MRI were to be used to generate vessel contrast for measure by the embodiments disclosed, mp-MRI and the embodiments disclosed could be interspersed in time as the contrast reached a maximum and then decreased as the labelled bolus of blood moved out of the prostate. Otherwise, endogenous contrast such as ASL could be used for this purpose. As endogenous contrast does not involve injection of Gd, it is in line with the non-invasiveness of the embodiments disclosed.

In addition to the other mp-MRI imaging, the embodiments disclosed would be used to acquire textural signature using T1, T2, diffusion-weighted contrast, though, as desired, additional contrast methods could be applied. Gradients for these techniques would be applied in varying directions, to learn something about the directionality of the underlying tissue structure as this is a component in associating structure with pathology.

For each patient, comparison of the data obtained from the various applications of the embodiments disclosed would be compared with all other diagnostics to "train" the method to yield the highest disease-specific information. The various input information sources include all other diagnostics, such as the mp-MRI data, serum measures, biopsy, physical exam, ultrasound, CT (Computed Tomography, and PET (Positron Emission Tomography). In addition, pertinent patient/disease history would be included in the training set. By this method, textural signatures specific to an individual pathology course can be identified.

Many neurologic diseases and conditions have a vascular component that may serve as a marker for disease onset and progression, allowing diagnosis and therapy tracking which provides another exemplary implementation of the methods disclosed herein. The ability to sensitively assess changes in micro-vessels would enable monitoring of pathology progression in a number of diseases which are often not diagnosed until pathology is well advanced.

Angiogenesis, formation of new blood vessels from pre-existing micro vessels, is necessary for tumor growth and metastasis. Rather than the ordered formation of vessels that exist in healthy tissue, pathogenic angiogenesis tends to form chaotic, tortuous vessels, replete with blocked, dead end structures—see FIG. 23. Vessel diameter and wall thickness are highly variable in angiogenic micro-vessels, with marked vessel permeability in places.

For example, tumor aggressiveness is closely correlated with neovascular density, as angiogenesis is needed to supply the tumor with oxygen and nutrients. The ability to assess the amount of angiogenic development at a tumor site, and to characterize the vascular morphology, would enable assessment of tumor aggressiveness. By determining the extent of the angiogenic vasculature within and surrounding the tumor, it is possible to determine the necessary boundaries for surgical removal. Likewise, therapy response may be trackable in part by measurement of vasculature as it reverts to a more normative state. Degree of angiogenic vasculature development can be assessed to some extent using serum markers, or by biopsy. But biopsy is highly invasive, and prone to sampling errors and read variability.

As another example, several forms of dementia, most notably Alzheimer's disease (AD), are now recognized as having a large vascular component with pathogenic vessel development. Additional forms of dementia, such as Huntington's disease (HD), Parkinson's disease (PD), and Frontotemporal dementia are also found to have compromised vasculature. In some cases, the salient cause of the dementia appears to be pathogenic vasculature in the brain, such as CVD.

Chronic inflammation is another important factor that can lead to abnormal neurovascular structure, exhibiting permeability and hemorrhage. Some microvasculature pathogenesis is linked to permeability of the blood brain barrier. Multiple Sclerosis, a brain disorder with pathology associated with inflammation and axonal demyelination, exhibits microvessel disruption. Stroke and the resultant ischemia result in development of angiogenesis modifying the capillary network, as the body attempts to heal the damage. As angiogenesis features increased vascularity, involving both structural and functional alterations within the neurovascular system, this increased density, and the high variability in vessel spacing, is a promising biomarker that can be used for the characterization of ischemic conditions in the brain following stroke. For all of these conditions—tumor development, ischemic stroke, and brain pathology in dementia, a means of assessing the micro-vasculature in brain tissue, is needed—both for determination of pathology advancement, and for assessment of therapy response.

Currently, MRI assessment of the health of microvasculature is most commonly made by perfusion imaging. Perfusion is the irrigation of tissues via blood delivery through the microvessels. Because the state of the vessels changes the dynamics of blood flow, such measure can be used to assess vascular health. For perfusion MR imaging, either endogenous or exogenous contrast is used. Exogenous contrast is most commonly provided by use of Gd-based contrast agent. Endogenous contrast is obtained through a technique known as ASL (Arterial Spin Labelling) in which the blood flowing into a region of the brain is magnetically labelled. In both cases, sequential images are made via fast imaging techniques, as the contrast moves into, and exits, the imaging plane. One of the key features of dynamic imaging, such as perfusion imaging, is that differential contrast can be obtained via subtraction of the image obtained with no contrast agent/blood tagging in the imaging plane from that obtained when contrast is at a maximum in the imaging plane.

When using a contrast agent for this measure, a bolus of the agent is injected intravenously and successive images are acquired as the contrast agent passes through the microcirculation. (Opposite to what is observed when no contrast agent is used, use of T2 weighting results in dark blood when a contrast agent is used, and T1 weighting results in bright blood.) In order to enable fast data acquisition to allow multi-image tracking of the flow before the contrast agent leaves the imaged tissue region, images are usually acquired using a variant of the fast MRI acquisition sequence known as EPI (Echo Planar Imaging). To characterize the state of the vessels, various flow related quantities are measured: (MTT) mean transit time through the voxels, time to peak signal, CBF (Cerebral Blood Flow), and CBV (Cerebral Blood Volume). These quantities, which vary with vascular condition, are all measurable via perfusion imaging. In addition to the sequential acquisition of images obtained while the bolus of contrast agent is present in the blood, or the magnetically labelled blood is flowing in the imaging plane when using ASL, at least one image is taken following passage of the bolus, or of the labelled spins, through the microvasculature, when contrast between the blood and surrounding tissue is minimal. This image is then subtracted from the early images to allow calibration of the absolute signal level from the microvasculature. Temporal tracking by acquisition of multiple images enables flow characterization and determination of regions of compromised vessels.

Angiogenic vasculature is denser, and more varied in vessel diameter and spacing, than are healthy vessels. The high spatial variation in vessel thickness and spacing is one of the hallmarks of angiogenic vasculature and hence, along with increased vessel density, serves as a marker for angiogenesis-related pathology. However, image resolution in perfusion imaging is not high enough to determine detailed vascular morphology. Flow contrast highlights locally averaged signal variation due to the pathogenic flow parameters, offering indirect assessment of vessel morphometry. However, the methods disclosed herein can be used to directly measure vessel density, and vessel spacing variability, to provide direct, robust assessment of angiogenic vessel development. Using the methods disclosed herein to acquire signal vs. k-value data disclosing tissue texture enables robust resolution of the morphometric features of the vessels. This acquisition can be done in one TR, fast enough that the sequence can be injected into the multi-image-acquisition perfusion series. To provide best resolution, this morphometry acquisition would be done near peak contrast, either acquiring data for one TR or for multiple TRs acquired either sequentially or interspersed at various time points with the perfusion image acquisitions.

Obtaining a differential measure of the vasculature by the methods disclosed herein, obtaining signal vs. k-value data both with and without contrast, provides validation of the origin of the textural signal as arising from the vasculature. Making these two measures as close in time as possible allows best spatial and phase correlative value between the two data acquisitions, to accurately highlight the signal arising from the vessels.

The best way to keep the time between the two acquisitions short when using ASL contrast is by 1) acquiring data, by the methods disclosed herein, in a specified imaging plane with proton density contrast; 2) immediately following the first acquisition, spin labelling in a second plane, upstream in the blood flow, in close proximity to the imaging plane; 3) acquiring spin-labelled data in the imaging plane, by the methods disclosed herein, the labelling and $2^{nd}$ acquisition as close in time as possible following the first acquisition. Signal vs. k-value data can be acquired using either gradient on or gradient off acquisition, or a combination of the two, to provide measure of signal across the desired span in k-space Because the morphometric parameters being measured are expected to vary significantly, acquisition of signal across a range of k-values is required, to determine the underlying structural signature of the vessels. The broadness of the distribution of signal vs. k-value, and where its peak lies in k-space are the critical features of interest. The peak assesses the average vessel density and the broadness assesses the variability of vessel spacing; both markers for angiogenesis characterization. The acquisition can be done either with a gradient on or with the gradient off during acquisition. Appropriate windowing in the direction of the acquisition axis of the VOI will allow sampling at a targeted spread of k-values, the exact window function determining the degree of correlation across the k-value range. Additionally, hybrid acquisition is possible wherein a gradient is on for some part of the data acquisition within one TR and off for part of the acquisition. The aim here is to, while acquiring a range of k-values, ensure sufficient repeats of, say, a set of highly correlated k-values, to allow SNR maximization by averaging, while ensuring fast enough acquisition to provide immunity to subject motion.

Alternatively, rather than temporally intersperse data acquisition by the methods disclosed herein into standard perfusion imaging, the methods disclosed herein can be used in conjunction with any blood contrast method to measure vessel morphology directly, in regions exhibiting pathogenic flow parameters. Both vessel spacing and the variability in this measure are known markers of angiogenesis, the vasculature spacing becoming more random with degree of pathology. For contrast, either structural contrast such as T2 or T1 weighting, which yield, respectively, bright or dark blood, can be used. Additionally, both black blood and bright blood flow contrast can be achieved by various standard methods, including arterial spin labelling. This structural measure of the vessels can be carried out in as many tissue regions, using as many acquisition directions, as desired. Angiogenic vasculature would be expected to exhibit a high degree of anisotropy, so varying the orientation of the acquisition axis between acquisitions provides another marker of pathology. Correlation of the flow data from the perfusion imaging with the structural vessel data from application of the methods disclosed herein, can be made through machine learning.

For tracking angiogenesis relating to ischemic stroke, or in the vicinity of a tumor, acquisition by the methods disclosed herein to assess the vessel structure, can be carried out in the vicinity of lesions. To achieve this, a real time response to an imaging scan that defines the location of these lesions would be used to target the location for the subsequent vessel structure measurements by the methods disclosed herein. Acquisition using multiple VOIs/locations and multiple acquisition orientations can be done for correlation with the various lesions appearing on the imaging sequence.

To study vascular pathology associated with brain disease such as dementia, the VOI can be positioned in the vasculature near the cortical region(s) implicated in the dementia. Data can be acquired in one or more VOIs in one TR. Additionally, in scanners capable of parallel imaging, multiple VOIs can be defined with simultaneous record of data to sample extended areas of the brain vasculature. For example, in dementia in which multiple cortical regions seem to be damaged, VOIs can be placed in the vasculature feeding these different regions and data recorded simultaneously.

The usual path for diagnostic development is feature extraction from the output data towards biomarker identification. Though feature extraction may define a specific biomarker, often in diagnostic development extended clinical work (years, dollars) is needed to strongly correlate biomarkers with pathology. This reliance on statistical correlation of individual inspection-derived biomarkers with outcomes is further stymied by the small size of initial test populations.

Medical data analysis is changing rapidly. Recently developed analysis techniques enable efficient determination of the total information content of data acquired using new diagnostic methods. In contrast to the previous "hunt and peck" method, current pattern recognition and machine learning techniques enable rapid correlation with other diagnostic content. In this way, feature extraction and biomarker development can be done by machine learning rather than by human observation of data. In effect, rather than isolating one characteristic (biomarker) from the entire signal vs. k-value dataset is correlated with other patient data to yield strong pathology correlations. As such, focusing on the acquisition end of the embodiments disclosed enables highest possible SNR as input to the machine learning algorithms used in this effort.

Computer programs are now adept at determining patterns within single images as well as performing highly efficient correlation of data with other medical history/diagnostic information. Data output from application of the embodiments disclosed, when taken in its entirety, provides the highest information content. Rather than reducing the information content through front-end feature extraction, the entire distribution of signal vs. k-value acquired from each VOI will be fed into a machine learning algorithm with pertinent diagnostic data taken by the current standard measures. For example, correlational data could be liver disease staging (F0-F5) derived from a doctor's report derived from histology images, the current gold standard measure for liver disease, liver function tests (liver serum), and physical exam.

Alternatively, the correlational data could be the output from any of those tests individually. With sufficient number of cases, this would enable finer gradations to be defined in disease staging, for instance, steps in between each stage—F0 and F1, between F0 and F2, and between F0 and F3, would be possible to define using this method. Additionally, outcomes—progression to more advanced pathology, or therapy-induced healing—can provide correlational data for machine learning algorithms for correlation with textural assessment from application of the methods disclosed herein.

The assessment stage obtained by the methods disclosed herein can be mapped on top of a standard MRI morphology image of the diseased liver. (For easier viewing, an icon can replace the staging number.) This will facilitate visualization of the disease variability through the organ. Additionally, these staging values can be correlated by machine learning with the imaging output obtained on the same patient by MRE, standard DWI, or perfusion, for instance to track possible correlations.

A final example of pathology assessment employing the methods herein is brain tissue. Brain pathology is often problematic to diagnose and treat because of the sensitivity of the organ to intervention. Further, changes in cognition and behavior can occur over a long time span such that the underlying pathology can go unchecked for years. In AD there is a long pre-symptomatic period, with underlying, ongoing development of pathology at the molecular and tissue level, leading eventually to neuronal damage. Though several have been tested in large clinical trials, there has been a stunning lack of approval for new therapies for AD or other forms of dementia. As the population ages, swelling the ranks of those afflicted with the disease, the situation is dire. The negative results of several of these clinical drug trials highlight the need for targeting subjects earlier in pathology development. However, this requires a diagnostic capable of targeting subjects in the pre-symptomatic phase. A test to identify such subjects has remained elusive.

Studies indicate that gray matter is affected earlier than white matter with dementia onset and progression. The cortical structures found to be earliest to suffer degradation are the hippocampus and entorhinal cortex, pathology which leads to memory loss and disorientation. Recent research applying image processing to 3 T1-weighted MR images of the brain has indicated a statistically significant correspondence between textural features on images of the hippocampus and MMSE (Mini Mental State Exam) scores. The texture is not directly measurable with MR imaging, due to insufficient resolution, but image analysis metrics correlate specific textural gradations with glucose uptake reduction in the hippocampus and subsequent hippocampal shrinkage, a marker for AD, in addition to the correlations with reduced MMSE scores. These texture features are not discernible except as a result of image processing, and their source is not known. Research indicates that these textural changes precede cognitive decline, and track with symptom onset. Thus, the hippocampus is a good target for application of the embodiments disclosed of texture measurement for pathology assessment.

As the exact etiology of dementia within the hippocampus and entorhinal cortex is unknown, the embodiments disclosed will be used to gather a sufficiently complete data set to provide detailed assessment of tissue texture within the organ—either the hippocampus or the entorhinal cortex. Both textural wavelength content and variability, as well as orientation and location dependence will be measured. Signal acquisition across a range of k-values, in at least 3 (orthogonal) directions, using a plurality of contrast methods (as the origin of the texture is unknown), is requisite to well-characterize the texture. Acquisition of data across the organ, by defining VOI dimensions to enable fitting the VOI fit into the organ entirely at different locations will enable determination of the spatial variability of the texture. By acquiring signal data across a range in k-space corresponding to wavelengths of tens of microns out to about 1-2 mm ensures that a large variety of textural signals contribute to the information content of the measurement. The embodiments disclosed can be used in conjunction with any contrast mechanism, such as inversion recovery, a heightened form of T1 weighting, or diffusion weighting.

The predictive value of the novel biomarker provided by the textural data acquired by the embodiments disclosed, towards assessment of the degree of AD pathology, can be defined by correlation with a range of diagnostic information from the same patient. The main correlation marker will be drawn from patient outcomes—i.e. definitive diagnosis of AD or other dementia—as this has the highest diagnostic information content, though definitive diagnosis is well-downstream from the pathology we are assessing. Additional correlation will be drawn from patient MRI imaging data on hippocampal shrinkage, a proven, and continuous, marker of advancing AD (as well as other forms of dementia). This correlation will be made longitudinally with disease progression, if possible. Again, changes in tissue texture in the hippocampus are expected to predate noticeable cognitive decline, and measurable change in volume via MRI. A third correlative marker is FDG-PET, as decline in glucose metabolism is expected to occur early relatively in disease progression. As a fourth correlative biomarker, the MMSE (Mini Mental State Exam) provides longitudinal data on cognitive functioning and decline. Genetic predilection for AD provides an additional marker for correlation with the textural measure acquired by the embodiments disclosed. While the previous markers provide downstream correlative value (on the outcome side), genetic markers exist in advance of any pathology development. Correlation of this varied set of biomarkers with the data acquired by the embodiments disclosed in the hippocampus and entorhinal cortex, across a broad range of patients, will enable a clear definition of diagnostic content of the use of the embodiments disclosed for early stage prediction of AD pathology.

Current machine learning algorithms are capable of pathology level classification of non-specific features, as will be obtained from MR data acquisition by the embodiments disclosed. As such, the disclosed sources of correlational data above will be input into machine learning algorithms to highlight the correlation with textural features and disease.

Though research has indicated that the hippocampus may be the earliest affected cortical structure with AD progression, its depth within the brain results in lower SNR due to distance from the MR sensing coil. Texture within the neocortex provides a target for assessment of dementia and other brain pathology that, due to its proximity to the skull, offers higher SNR. In the healthy brain, very ordered neuronal architecture is found in the neocortex. The neurons form in bundles of approximately 50 microns in width and 80 micron spacing, with about 80 to 100 myelinated neurons grouped together in each bundle. This is the minicolumn organization visible in histology of neocortical tissue. In specific regions of the brain that are seen by histology studies to be affected early in AD progression, this columnar order loses coherence over the prodromal stages. These changes happen in advance of general brain atrophy, an often-used marker for AD progression, making them a better target for early stage diagnosis. Further, the temporal progression of minicolumn thinning and loss of coherence across specific brain regions reflects the regionally selective progression of tangle pathology in Alzheimer's Disease (AD). Hence, tracking the changes in cortical minicolumns spatially in the brain using the embodiments disclosed enables typing of dementia, as each form of dementia follows a specific spatial progression through the brain.

Figure 27:
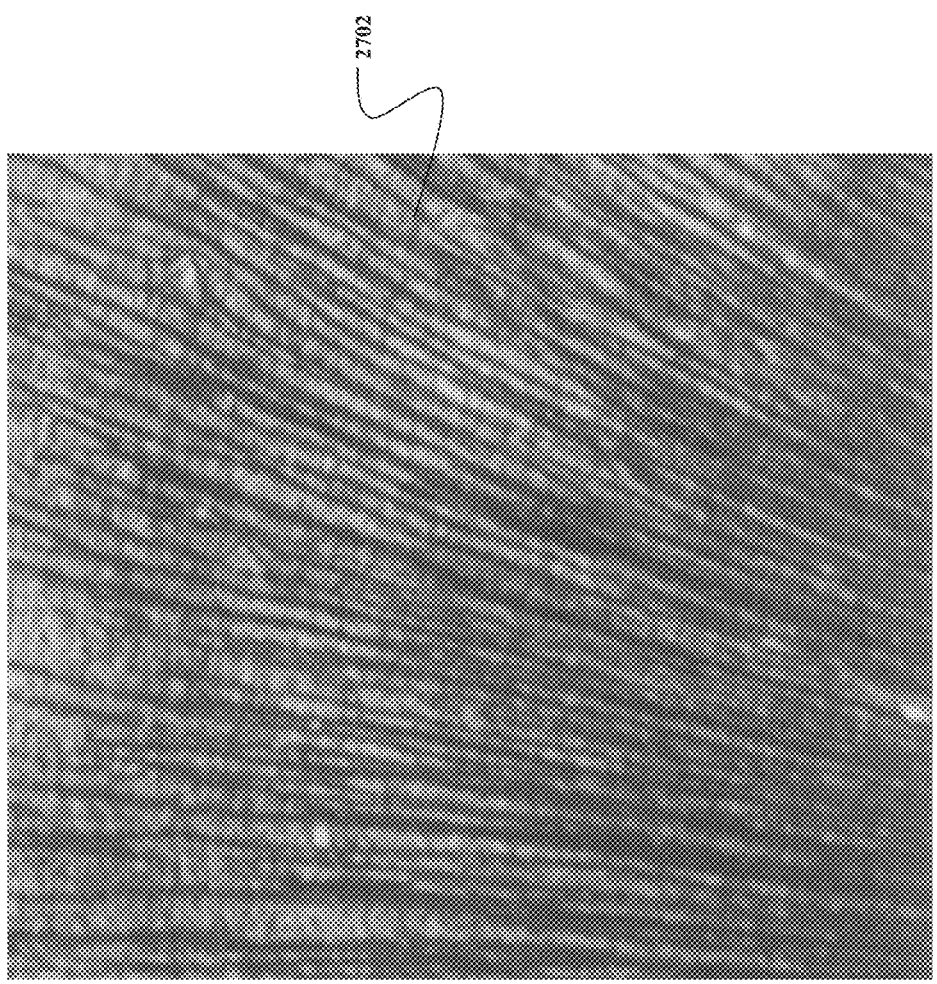
FIG. 27 is a pictorial representation of cortical minicolumns in the brain.
Figure 29A:
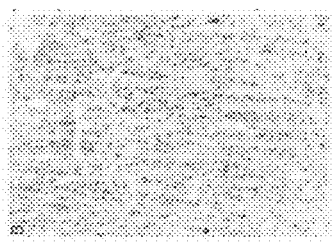
FIGS. 29A-29C are representations of three histology images showing progressive pathology with AD advancement.
Figure 29B:
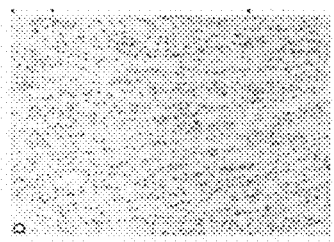
Figure 29C:
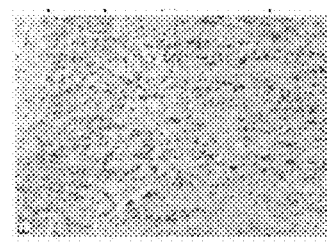

The structure of these minicolumns in healthy brain can be seen in FIG. 27, a histology image stained to reveal myelin 2702—the coating sheathing the neurons. FIGS. 29A-29C are a series of three histology images stained to reveal the pyramidal neuron cells in the bundles. FIG. 29A is of neuronal order in healthy brain and FIGS. 29B and 29C show progressive pathology with AD advancement—the columnar spacing shrinks and the ordered structure becomes increasingly random.

Changes in the spacing and order of the minicolumns in these cortical regions are early harbingers of disease. Though research in this area is in early stages, as with other pathology, the underlying tissue changes must predate symptoms. The problem is that currently there is no technique able to reach the resolution needed to assess these early-stage changes in the columnar texture. The embodiments disclosed enables this measurement.

There are several methods by which the embodiments disclosed can be implemented to measure the change in spacing and order of neocortical minicolumns. For this measurement to reflect early stage changes, it would be applied to the regions of the neocortex that appear to affect behavior earliest in the onset of AD, such as the temporal cortex. As these regions are in the neocortex on the outside of the brain, they will yield a strong SNR in a brain coil.

Figure 28:
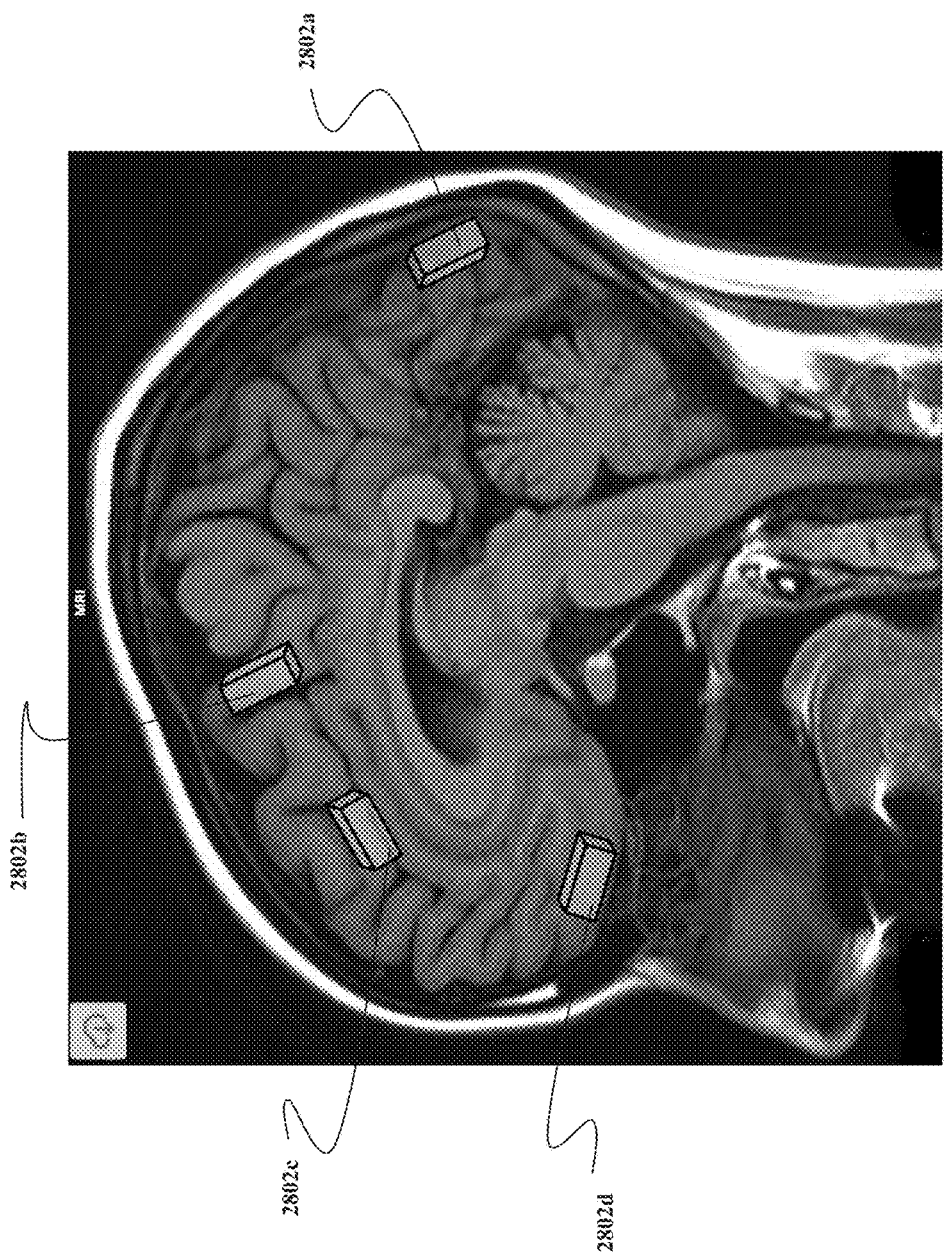
FIG. 28 is a pictorial representation of VOI placement in the brain.

FIG. 28 is a representation showing possible positioning of the VOI 2802*a*, 2802*b*, 2802*c* and 2802*d* in the neocortex 2804.

As the axonal component of the neurons forming the minicolumn bundles are sheathed in myelin, a fatty substance, T1 contrast can be used to highlight the axon bundles against the background tissue and hence is a good choice for contrast when assessing these structures.

A difficulty in measuring the columnar spacing results from the semi-crystallinity of these structures. In healthy neocortex, they are highly ordered in the vertical (parallel to columns) direction. As a result, because the acquisition axis of the VOI must intercept several of these columns to make a measurement, the differential signal that contrasts the neuronal bundle from the background tissue is extremely sensitive to orientation of the acquisition axis. To measure the columnar spacing, the acquisition axis of the VOI is aligned normal to the length of the columns. Slight misalignment diminishes contrast—precise orientation is required for the measurement. To achieve proper alignment, rocking the acquisition gradient angle over incremental angles of approximately a degree or two will show a signal resonance at the proper alignment i.e. consecutively repeating the time varying series of gradients to produce trajectories through 3D k-space with resulting k-value sets oriented around the specific k-value to locate resonance. (The slight curvature of the cortex would be expected to provide a finite width to this resonance of signal amplitude vs. angle.) A trajectory through 3D k-space and a resulting k-value set oriented within 10 degrees of the initially encoded specific k-value is employed in exemplary embodiments. As the columnar structure loses coherence with pathology advancement, the width of this resonance would be expected to broaden, and eventually disappear when the structure becomes highly random, as shown in the histology image in FIG. 29C.

Using the embodiments disclosed, acquisition of signal can be at a (nominally) single k-value, or over a band of k-values defining in advance of t the measure a finite extent in k-space over which to acquire the signal.

As the spacing of minicolumns in healthy human brain is approximately 80 microns, sampling from about 70 microns to 110 microns would encompass the resonance. In exemplary embodiments this is accomplished by placing the VOI within the cortex and providing the spatial encode in the range of k-values corresponding to spatial wavelengths of 40 micrometers to 200 micrometers.

Making measurements in the cortex with the embodiments disclosed involves these basic steps: 1) A contrast mechanism is selected to highlight the structure. 2) individual k-values or the span of k-values for which signal is to be acquired is determined. 3) the timing of the k-value acquisitions—how many repeats at each k-value or spread of k-values is determined. 4) the size of the VOI and orientation(s) of the acquisition axis in the neocortical tissue are selected.

5) A VOI is positioned in the center of the cortex height, aligning the acquisition axis parallel to the top and bottom surfaces at the VOI midpoint, as closely as possible. 6) Signal vs. k-value data is then acquired with the gradient on or off to measure the minicolumn spacing; measurement across a broad range of k-values encompassing on the average spacing of the minicolumns as indicated in the literature (approximately 80 μm) will ensure coverage of the width distribution. Signal intensity maximum should occur when the acquisition gradient is oriented normal to the columns. 6) The acquisition gradient is then rocked in small angular increments to look for the signal resonance—the sharpness of the signal resonance vs. angular deviation reflects the order of the minicolumns. A sharp resonance indicates ordered structure. A broad resonance as a function of angular deviation indicates columnar degradation has introduced randomness into the minicolumn order. 7) Aligning the gradient to maximum signal return to sweep through the range of k-values look for textural wavelength resonances—i.e. the peak of the signal vs. k-value distribution from the texture distribution. This resonance also can be used to determine minicolumn order. A sharp peak (high q-value) in the signal vs. k-value curve indicates ordered structure, the broadness of the curve is indicative of the degree of loss of order. Locating the resonance in the signal vs. acquisition angle and in the signal vs. k-value distribution can be accomplished as an interactive process.

Data can be acquired at other positions in the cortex or nearby the original VOI, either within one TR or multiple TRs. Optimal VOI dimensions for characterization of the cortical minicolumns are determined by 1) the need to fit the VOI entirely within the cortex, which is 2-3 mm in height, 2) the requirement to sample sufficient textural repeats along the encode axis for accurate assessment of the textural wavelength, and 3) by signal requirements. Additionally, the smaller the height of the VOI along the direction of the columns determines the sensitivity to alignment.

The fewer repeats sampled along the encode axis, the greater the broadening in k-space of the signal acquired by the embodiments disclosed. Data can be acquired with the gradient off, relying on selection of the window width to determine the range of k-values contributing to the signal. Keeping the spread in k-space small enough ensures correlation in the signal output.

A change in spacing of neuronal columns indicates pathology advancement/aging; this can be determined by longitudinal monitoring of the peak of the signal-magnitude vs. K-value distribution.

As the structure degrades, the orientation resonance becomes broader and more diffuse, spread over a larger span of acquisition angles. Also as the structure degrades, the peak in the signal vs. k-value distribution becomes broader and more diffuse, spread over a larger span of k-values (wavelengths). Eventually, no peak will be visible in either case with progressing degradation of the minicolumn order, a marker of increasing degree of dementia. Further, changes in the minicolumns widths with advancing disease will be reflected in the column spacing, another marker of pathology.

A variation on this disease marker is the degree of anisotropy of the columnar order. As the columnar order degrades with progressing pathology, the degree of anisotropy of the columnar texture also lessens and the overall cortical tissue texture becomes more isotropic. The degree of anisotropy can be measured by use of T1, or other, contrast using the embodiments disclosed, with the VOI 3002 positioned as above, midway between the two cortical surfaces 3004 as seen in FIG. 30 and comparing the signal vs k-value distribution with the acquisition axis normal to the cortical surfaces (parallel to the minicolumns), with the signal vs. k-value distribution obtained with the acquisition axis aligned tangential to the cortical surfaces 3004 therefore (normal to the minicolumns) as shown in FIG. 30.

The use of diffusion weighting in brain pathology, including stroke and brain tumors, is increasing. Diffusion weighted imaging (DWI) provides an indirect measure of structure at the cellular level, by applying gradients that first dephase and then rephase signal in a targeted location.

Stationary water molecules are rephased by the second gradient, but those that have moved between the two gradients are not, hence yielding no signal. The difficulty with the technique is that, by design, it is extremely sensitive to motion. It is also low SNR, due to the late echo time resulting from the need for the long diffusion gradients. Use of the embodiments disclosed for data acquisition when using diffusion contrast can remedy the motion problem as, though the echo time is still long, data acquisition is fast enough that the signal loss and blurring due to motion is minimized. The embodiments disclosed can be used with diffusion weighting contrast to assess the spacing and order/randomness of the minicolumns. This measure can be made with the diffusion gradients applied parallel to the surfaces of the cortex (normal to the minicolumns), and then normal to the cortical surfaces (parallel to the minicolumn direction). These two measures enable assessment of the anisotropy, which will be highest in healthy brain, pathology then inducing increasing isotropy as the columns degrade.

Figure 30:
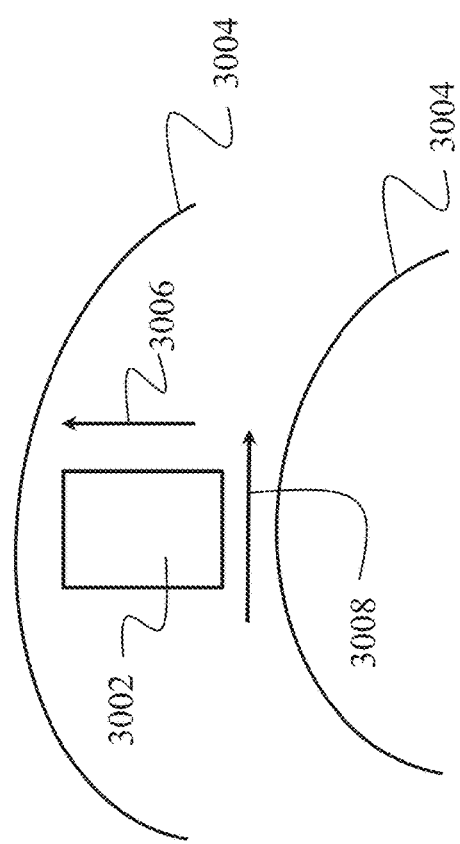
FIG. 30 is exemplary representation of placement of a VOI in the brain cortex and application of gradients for k-value.

Using diffusion weighting, with reference to FIG. 30: applying the gradient as indicated by Gradient 1 3006 will yield low signal if minicolumns still intact. Similarly applying gradient as indicated by Gradient 2 3008 will yield high diffusion signal if minicolumns still intact.

As minicolumns degrade, signal with the two different gradients approach each other expect diffusion weighted signal to increase overall as minicolumns become highly degraded.

A refinement on this measure is through application of the diffusion gradient in multiple directions for data acquisition and development of the diffusion tensor similarly to diffusion tensor imaging (DTI), but with data acquisition being by the embodiments disclosed. Development of a diffusion tensor requires using at least 6 non-collinear directions of diffusion gradient orientation to yield sufficient data to generate the tensor, the eigenvalues of which determine the level of Fractional Anisotropy (FA) in the cortex, reflective of the order of the minicolumns. The FA should change, moving toward more isotropic organization as columnar organization degrades—an FA value of 1 indicates highest anisotropy, and a value of 0 indicates maximum isotropy of the underlying diffusion, hence revealing the order of the columnar texture.

As with the other types of contrast mechanisms used in conjunction with the embodiments disclosed, the targeted k-values are selected by a combination of knowledge of the approximate location in k-space of the minicolumns from the literature and from measure when they are still sufficiently ordered to define a clear textural wavelength signature, and pre-measure to determine the distribution of signal vs. k-value. One method to achieve this is with a gradient on to provide sufficient spread in k-space during data acquisition to enable finer sampling on the subsequent acquisition(s), though this measure can also be made using gradient off acquisition.

In the cortex, the mean diffusivity (MD) of water is found to decrease with increasing dementia. Using the embodiments disclosed it can be determine if this is due to minicolumn disorder by measuring the spacing, order, and anisotropy of the minicolumns as described above. The signal vs. k-value data obtained using the embodiments disclosed, can be input into a machine learning algorithm, with correlational data from cognitive evaluation tests such as the MMSE exam, downstream neuropathology outcomes, and serum and imaging data.

In addition to Alzheimer's dementia, changes in, or abnormal morphology in, minicolumn structures occur with Parkinson's disease, Dementia with Lewy bodies, Amyotrophic Lateral Sclerosis, autism (autism spectrum disorder is reflected in wider, hence more tightly packed, minicolumns), and schizophrenia (for which the normal thinning of the columns with age does not appear to take place, leading to more widely spaced minicolumns), dyslexia and ADHD. Hence, the embodiments disclosed can be used to assess degree of pathology in any of these conditions. Correlation for machine learning to determine the association between measured data and pathology can be obtained from cortical atrophy segmentation, MMSE, doctor's evaluation of degree of pathology from observational data, etc.

Additionally, the embodiments disclosed can be used with stationary contrast mechanism to highlight tissue texture changes and flow contrast to highlight vasculature changes in the vicinity of a lesion showing up on an MR image, that may indicate stroke or tumor related pathology.

Studies indicate that gray matter is affected earlier than white matter with dementia onset and progression. The cortical structures found to be earliest to suffer degradation are the hippocampus and entorhinal cortex, pathology which leads to memory loss and disorientation. Recent research applying image processing to T1-weighted MR images of the brain has indicated a statistically significant correspondence between textural features on images of the hippocampus and MMSE (Mini Mental State Exam) scores. The texture is not directly measurable with MR imaging, due to insufficient resolution, but image analysis metrics correlate specific textural gradations with glucose uptake reduction in the hippocampus and subsequent hippocampal shrinkage, a marker for AD, in addition to the correlations with reduced MMSE scores. These texture features are not discernible except as a result of image processing, and their source is not known. Research indicates that these textural changes precede cognitive decline, and track with symptom onset. Thus, the hippocampus is a good target for application of the embodiments disclosed of texture measurement for pathology assessment.

As the exact etiology of dementia within the hippocampus and entorhinal cortex is unknown, the embodiments disclosed will be used to gather a sufficiently complete data set to provide detailed assessment of tissue texture within the organ—either the hippocampus or the entorhinal cortex. Both textural wavelength content and variability, as well as orientation and location dependence will be measured. Signal acquisition across a range of k-values, in at least 3 (orthogonal) directions, using a plurality of contrast methods (as the origin of the texture is unknown), is requisite to well-characterize the texture. Acquisition of data across the organ, by defining VOI dimensions to enable fitting the VOI fit into the organ entirely at different locations will enable determination of the spatial variability of the texture. By acquiring signal data across a range in k-space corresponding to wavelengths of ten microns out to about 1-2 mm ensures that a large variety of textural signals contribute to the information content of the measurement. The embodiments disclosed can be used in conjunction with any contrast mechanism, such as inversion recovery, a heightened form of T1 weighting, or diffusion weighting.

The predictive value of the novel biomarker provided by the textural data acquired by the embodiments disclosed, towards assessment of the degree of AD pathology, can be defined by correlation with a range of diagnostic information from the same patient. The main correlation marker will be drawn from patient outcomes—i.e. definitive diagnosis of AD or other dementia—as this has the highest diagnostic information content, though definitive diagnosis is well-downstream from the pathology we are assessing. Additional correlation will be drawn from patient MRI imaging data on hippocampal shrinkage, a proven, and continuous, marker of advancing AD (as well as other forms of dementia). This correlation will be made longitudinally with disease progression, if possible. Again, changes in tissue texture in the hippocampus are expected to predate noticeable cognitive decline, and measurable change in volume via MRI. A third correlative marker is FDG-PET, as decline in glucose metabolism is expected to occur early relatively in disease progression. As a fourth correlative biomarker, the MMSE (Mini Mental State Exam) provides longitudinal data on cognitive functioning and decline. Genetic predilection for AD provides an additional marker for correlation with the textural measure acquired by the embodiments disclosed. While the previous markers provide downstream correlative value (on the outcome side), genetic markers exist in advance of any pathology development. Correlation of this varied set of biomarkers with the data acquired by the embodiments disclosed in the hippocampus and entorhinal cortex, across a broad range of patients, will enable a clear definition of diagnostic content of the use of the embodiments disclosed for early stage prediction of AD pathology.

Current machine learning algorithms are capable of pathology level classification of non-specific features, as will be obtained from MR data acquisition by the embodiments disclosed. As such, the disclosed sources of correlational data above will be input into machine learning algorithms to highlight the correlation with textural features and disease.

Autism Spectrum Disorders (ASD) as a disease class are diagnosed solely on the basis of behavior. However, much research has reported anatomical difference in the brains of people with ASD. The ability to measure these anatomical variations in vivo would enable adding pathology-based diagnosis to that based solely on behavior, and would inform an understanding of the underlying etiology of this condition.

Along with an enlargement of the frontal cortex, alterations in the columnar organization of neurons in various regions of the cerebral cortex are found to be attendant with autism. The neuronal tracts that span the middle of the cortex form into bundles of approximately 80 neurons, spaced on the order of 50 microns apart, forming a columnar organization, the columns running perpendicular to the cortical surfaces. This organization has been shown in numerous histology studies to vary in ASD relative to that seen with normal development. As previously discussed the thinning and degradation of order in these minicolumns occurs with advancing AD. In ASD, minicolumn width has been found to be greater than in normal brains, reducing columnar spacing, and increasing the neuronal cell density. This change in columnar width varies spatially throughout the cortex—these variations have been found in some research to be limited to higher order association areas, and to spare primary sensory areas, these local differences mirroring cognitive symptoms. More work is needed to determine the etiology and correlate pathology with symptoms, as ASD appears to be highly heterogeneous.

In ASD minicolumns have been found to be on the order of 5% to 10% wider than in the normal brain. While not a huge difference, across the hundreds of thousands of minicolumns in the brain, this variation contributes to a significant difference in brain organization. Most significantly, this variation in density should be resolvable by the embodiments disclosed.

Structural change can be measured with the embodiments disclosed through use of contrast that will highlight the columnar organization against the background of cortical soft tissue. The most pertinent contrast here would be a fat-highlighting contrast such as T1 or IR, to reveal the lipids that sheath the axonal tracts issuing from the neurons. This contrast may diminish with advancing pathology as the degradation in minicolumn order could be attendant with degradation of the myelin axonal sheaths. Casanova and Trippe, "Radial cytoarchitecture and patterns of cortical connectivity in autism, Philosophical Transactions Royal Society B", 2009; Chance and Casanova, Minicolumns, "autism and age: What it means for people with autism", Autism Science Foundation, August 2015; Donovan and Basson, "The neuroanatomy of autism—a developmental perspective", Journal of Anatomy, 2017; McKavanagh, et al., "Wider minicolumns in autism: a neural basis for altered processing", Brain, July 2015; Opris and Casanova, "Prefrontal cortical minicolumn—from executive control to disrupted cognitive processing", Brain, 2014.

Another contrast mechanism that is applicable to tracking the variation in columnar order is diffusion weighting. This contrast mechanism has been discussed in some detail above, towards its application in AD diagnosis. Diffusion weighting measures local variations in the diffusion coefficient of water, these variations reflecting tissue changes at the microscopic level. In its use in imaging, high gradients must be applied for many milliseconds, to allow enough time to create a sufficient dynamic range in the measure of diffusion coefficients. This makes for a long echo time and hence a low SNR due to T2 dephasing. As such, in imaging the minimal voxel sizes are on the order of 2-2.5 mm on a side to enable sufficient SNR for the measurement.

Though the underlying phenomena leading to the change in diffusion coefficients are on the microscopic scale their resolution is limited in imaging, the size of the voxel required to generate sufficient SNR resulting in partial volume effects. Further, the technique is indirect in that the underlying mechanism responsible for the change in diffusion coefficient, which is averaged over the voxel, is unknown.

Use of diffusion weighting as contrast, in conjunction with the embodiments disclosed, would enable direct connection between changes in very fine tissue textures and the variation in diffusion coefficient with pathology. By limiting the textural wavelength(s) (k-values) acquired at each TR, the acquisition would provide sufficient time to acquire many repeats at the reduced set of k-values to enhance SNR. If it is desired to probe the power at multiple wavelengths/k-values, the measure of a reduced set can be repeated in successive TRs. Again, phase coherence between these separate measures of k-value is not required. The only requirement here is that the VOI remain in a tissue region with similar textural signature. In regions where the tissue texture changes rapidly spatially, and/or in measurements for which non-negligible motion is expected, motion correction schemes can be used to relocate successive VOIs within the tissue region of interest for each successive measurement.

A further use of diffusion weighting for contrast, to reveal changes at the level of fine tissue textures, is to use the DTI (Diffusion Tensor Imaging) scheme. In this method, the diffusion gradients are applied in at least six non-collinear directions, enabling determination of the directional diffusion field, to determine the measure of anisotropy in water diffusion indicative of a preferential direction/tissue change.

In schizophrenia, reduced neuronal density is seen in the cortex, in the left hemisphere in females and in the right hemisphere in males. This reduced density manifests as enlarged minicolumn spacing, and is attendant with absence of normal aging effects in the columnar organization in the cortex. It is reasonable to assume that many neuropathologies dealing with altered cognition, consciousness, and functioning would exhibit similarly attendant alterations in the cortical columnar order, the brain region suffering the attack varying with, and mirroring, the specific disease presentation. Chance et al., "Auditory cortex asymmetry, altered minicolumn spacing and absence of ageing effects in schizophrenia", Brain 2008.

For measure of cortical minicolumnar order and spacing to track pathology, positioning of the VOI is important so as to generate highest contrast between the columns and the background tissue. The VOI is first positioned in the cortical region of interest in the brain, based on where pathology is expected to strike during disease progression. Next, based on what is known of healthy columnar spacing and order, a VOI length, the acquisition axis, would be selected long enough that it would allow sampling of several columnar repeats. To ensure high contrast from column to background, the acquisition axis of the VOI should be positioned as close to parallel to the cortical surfaces as possible, resulting in the acquisition axis intersecting the column as close as possible to normal. This is difficult to do just by use of the reference image. The optimal method would be to first select the region of k-space of interest, a band of values peaked near the healthy minicolumnar spacing. Next, position the VOI parallel to the cortical surfaces. Then, best alignment can be accomplished by varying the angle of the tilt of the acquisition axis by a few degrees on either side of the selected orientation, in steps of about a degree, looking for the signal maximum within the selected band in k-space.

The cross section of the VOI can be chosen to be on the order of a few repeats of the healthy columnar spacing—smaller cross section favors higher contrast, but also reduces signal. The spread in k-space can be set either by acquisition with a gradient on to broaden the acquisition in k-space over the time of the measurement, or with stepped k-values, by windowing in sample space. The former procedure is preferred as it allows sampling of a larger number of textural repeats to better determine where the power of interest lies. This measure can be repeated across different ranges in k-space to determine the k-space region on which to focus for the diagnostic measure.

To optimize the capability of the embodiments disclosed for diagnosis of autism and assessment of the level of differentiation of the cortical tissue morphology from normal cortical tissue, machine learning would be applied. Inputs to such algorithms would be drawn from a multiplicity of diagnostic measures. Data acquired using the embodiments disclosed, with selected contrast and acquisition parameters, would be combined with patient histories, cognitive testing, exam results, imaging data, and outcomes to be analyzed via AI/machine learning algorithms MS is a chronic, inflammatory disease of the central nervous system characterized by immune-mediated demyelination of nerves. It is a leading cause of neurologic disability worldwide. Typically, a disease of young adults, the number of cases peaks in the fourth decade of life. Compounding the difficulty of understanding the disease triggers is the fact that disease course varies considerably from patient to patient. There is "relapsing-remitting" course with "clinically isolated syndrome" presentation—an incidence of cognitive symptoms lasting at least 24 hours, "secondary progressive", and "primary progressive" courses of the disease. A rare variant is the "progressive relapsing" course which presents with progressive course with acute relapses. T2 hyperintense lesions, a hallmark of MS, are incidental findings on an MRI exam in an asymptomatic individual. A. Katdare and M. Ursekar, "Systematic Imaging Review: Multiple Sclerosis", Annals of the Indian Academy of Neurology, July 2015. What is needed in MS is a diagnostic capability that will enable prognosis of developing pathology towards therapy selection, as well as a sensitive measure of therapy efficacy. Such measure, though, is complicated by the various presentations, and a lack of clear understanding of the various pathology courses underlying disability.

A growing body of evidence indicates that early intervention is required in MS to minimize the risk of permanent neurologic damage, which is often greatest early in the disease course. More sensitive measures of disease progression are needed to help predict the course of the disease and assess therapy efficacy. A more sensitive measure of very early stage disease is clinically necessitated. F. Piehl, "Multiple Sclerosis—A tuning fork still required", JAMA Neurology, March 2017.

Magnetic resonance imaging has become a major diagnostic and research tool in the study of MS. Advanced imaging techniques help provide a more accurate characterization of tissue injury, including demyelination, axonal injury, and its functional and metabolic consequences. The common basis for MS diagnosis is the dissemination of lesions in "time and space" in the brain, brain stem, and spinal cord. Gd (Gadolinium) has been used to enhance lesions in past, but recent findings of long term retention of Gd in the brain of patients has questioned the safety of its use. Alternatives to this contrast agent are being sought, as are alternative methods of highlighting lesions. Additionally, though tied to a specific temporal variability, white matter lesion load has only a poor correlation with symptoms of disability. This is thought to result from the presence of both focal and diffuse damage appears in the brains of people diagnosed with MS. A method of assessing the diffuse tissue damage, as well as assessing the tissue changes within lesions, is required to better understand the underlying pathology, towards prognosis of cognitive change, and to sensitively monitor therapy response. However, the imaging resolution needed to measure the underlying tissue damage within and surrounding lesions is not directly available with standard MR imaging, due to patient motion over the course of data acquisition. Though cerebral MRI has progressed the aim of quantifying MS-induced tissue changes, from WM lesion assessment to whole brain microstructural changes, the currently available MRI metrics still provide no clear explanation for, or diagnosis of pathology, either on a population-as-a-whole, or on an individual basis. Clearly more diagnostic information is needed.

A good portion of the MRI market results from the need for diagnostics for nerve and brain disorders. "MRI Market Primed for Growth", Aunt Minnie Europe, Feb. 27, 2017. More than that, the multitude of contrast mechanisms available for MR scanning enable acquisition of complementary data from within one modality, to provide a more nuanced read of underlying pathology. What has been missing in this, however, is direct structural measure at the level of the tissue texture, the biologic fabric that, in most pathologies, responds immediately to the chemical changes that drive disease. In some diseases, the chemical changes that drive pathology are known and measurable but, in others, the earliest measurable change is in the structural fabric of the tissue. However, this change is not measurable by imaging due to the resolution limits set by patient motion. Therefore, though MRI offers exquisite tissue contrast, it cannot resolve the sub-mm diffuse tissue changes that are the early harbingers of disease.

In past, MS was characterized as a disease of WM (White Matter) tracts and the CNS (Central Nervous System) with the focus on demyelination of the axonal tracts that carry signals from cortical grey matter to other parts of the brain. However, many recent imaging and pathology studies point to clear involvement of the grey matter. Cortical demyelination, which is seen to be present in early stage MS, may be a pathologic correlate of irreversible disability. Gray matter demyelination is extensive in most MS patients, and clear association between the lesion load in grey matter and cognitive impairment has been made. However, detection of GM lesions is difficult with standard MR contrast techniques, hence correlation with clinical symptoms remains problematic. Wegner and Stadelmann, "Grey Matter Pathology and Multiple Sclerosis", Current Neurological and Neuroscience Reports, 2009; Popescu and Lucchinetti, "Meningeal and Cortical Grey Matter Pathology in Multiple Sclerosis", BMC Neurology 2012; A. Katdare and M. Ursekar, "Systematic Imaging Review: Multiple Sclerosis", Annals of the Indian Academy of Neurology, July 2015. Further, though conventional MR sequences, specifically T1, T2, and T1 with Gd contrast, are sensitive for detecting WM lesions throughout the CNS, patient motion limits their ability to assess the underlying tissue damage within and outside the lesions. The diagnostic information that is missing here is the underlying changes in the tissue texture within the brain—both in regions of WM tracts and in the cortical regions (GM) occurring as a result of disease. Due to its immunity to patient motion, the embodiments disclosed can provide this measure.

MR techniques that generate contrast originating at a molecular and cellular level have been applied to the problem of developing a more complete understanding of the tissue changes underlying both lesions and the diffuse tissue damage inherent with MS. These non-conventional techniques, such as Magnetization Transfer Imaging (MTI), Diffusion-Weighted Imaging (DWI), and Diffusion Tensor Imaging (DTI) provide an indirect measure of the effects of disease-induced degradation of WM and GM. The difficulty with these measures is that, as they are indirect, changes in the signal intensities that they measure can arise from various pathology-related tissue changes—assigning a specific underlying cause is problematic. DTI does a good job of neuronal fiber tracking through the brain, showing the macroscopic holes that appear in the tracts due to pathology advancement. But it cannot determine the exact source of these changes on the level of fine tissue texture—i.e. the earlier and more sensitive measure of disease progression. Lesions are non-specific and may indicate areas of inflammation, demyelination, ischemia, edema, cell loss, gliosis. A better understanding of the fine-scale pathologic changes resulting in the observed cognitive impact of MS is needed.

Though lesion size, number, and spatial and temporal distribution are clear contributors to disease progress evaluation, T2 weighted MRI lacks pathologic specificity and specific predictive capability.

WM pathology in MS is dominated by an inflammatory response leading to degradation of the myelin sheath surrounding the axons comprising the neuronal tracts that run through the brain. Direct measure of myelin loss at an early stage, before the appearance of well-defined lesions in the WM, would be a most useful diagnostic measure towards early treatment. Single axons are on the order of 1 µm, hence combined degeneration is required to produce a measurable signal. The marker sought is the decrease in myelin along the tracts as axonal degeneration progresses. The localized degradation appears as a WM lesion in T1 and T2 weighted images.

Due to the complexity of MS pathology, a single diagnostic measure would not be expected to completely unravel the underlying causes of pathology onset and progression. The ability of computers to store and process ever larger data sets has enabled complex image processing and interpretation, using multiple measures of image data obtained under conditions of different contrast, from a single patient. Further, computation capability has made it possible to more accurately derive biomarkers from new MR diagnostic measures, through use of machine learning algorithms that correlate data obtained by differing MR contrast, differing modalities, combined with patient metadata and outcomes, across an entire population.

Along with the needed development of more sensitive/specific MRI diagnostic approaches that can provide earlier diagnosis, improved post-processing is needed to maximize information extraction. Bakshi et al., "MRI in multiple sclerosis: current status and future prospects", Lancet Neurology, July 2008.

Combination of diagnostic information has the best chance of revealing underlying pathology in MS, especially given the ability to combine these measurements using AI/machine learning/deep learning algorithms. However, though the correlation of data is more powerful than single measures, high information content inputs to the algorithm drive its sensitivity and efficacy. In its ability to directly measure the very fine textural changes in affected brain tissue, the embodiments disclosed provides a key piece of data towards enabling sensitive measure of MS progression. Further, it provides a high-information-content measure of textural morphology, which can be applied: 1) as a correlational measure towards calibration of other indirect MRI pulse sequences/contrast methods, such as DWI and MTI, or 2) it can be run in an integrated mode with any specific contrast mechanism selected to provide highest tissue contrast, the MR data being acquired using the embodiments disclosed with the tissue contrast being provided by whatever contrast mechanism provides optimal contrast. This may be standard contrast such as such as T1 and T2-weighting, or more advanced measures such as DWI or MTI. (FIGS. 24 and 25 as discussed above, demonstrate an integrated DWI/texture pulse sequence).

Inflammation in MS causes both demyelination of neuronal tracts and axonal injury. Brain atrophy follows and is reflected in cortical thinning, which can be measured in MRI using post acquisition segmentation. However, by the time cortical atrophy is measurable, significant neuronal damage has already occurred in the cortex, atrophy being the macroscopic mirror of integrated tissue damage. Direct measure of tissue change/myelin loss at an early stage, before the appearance of measurable atrophy or well-defined lesions, is needed as a diagnostic measure enabling early treatment. Fox et al., "Advanced MRI in Multiple Sclerosis: Current status and future challenges", Neurologic Clinics, May 2011.

Single axons are on the order of 1 µm, hence combined degeneration is required to produce a measurable signal. However, in the cortex, neurons bundle together in groups of about 80, enabling a sufficiently sensitive measure of tissue change to track the degeneration underlying cortical thinning. This is largely equivalent to the cortical damage inherent in progressing Alzheimer's disease. Degeneration in these columns, as indicated by lack of order, and degrading myelin, is one of the early markers of MS.

Another contrast method that has been applied in an attempt to quantify myelin degradation is Magnetization Transfer Imaging (MTI). Water bound in macromolecules such as myelin decay too quickly to allow recording of their MR signal, hence measure of signal strength directly is not possible. However, due to dipole interactions between free water in the brain and bound hydrogen protons, changes in the ratio of the free and bound pool of protons can be measured. Though this is a sensitive measure of change of water content, as with difffusion imaging, the underlying mechanism causing the change can be ascribed to multiple pathologic phenomena. MTR associated with myelin content but, as it is also affected by water content, from say edema and inflammation, you can't tell exactly what is causing the change in MTR. MTR changes by both changes in the free hydrogen pool (water content) and the bound hydrogen pool (e.g. those bound to proteins and lipids in cellular membranes such as in myelin). Comparison with histopathology has shown reasonably good correlations with both demyelination and remyelination, and with overall neuronal density. Therefore, association of changes in MTR as reflecting myelin content is not at all straightforward. This is the power of direct structural measures—the interpretation relies only on the contrast mechanism Vavasour et al., "Is the Magnetization Transfer Ratio a marker for myelin in Multiple Sclerosis", Journal of Magnetic Resonance Imaging, 2011.

As with the incorporation of the embodiments disclosed and diffusion weighting within one pulse sequence, the embodiments disclosed can be combined directly with MTI contrast, to highlight structures whose contrast arises from variations in water content.

DWI and DTI yield different insights, though both measure the microscopic Brownian motion, or diffusion, of water molecules, which is hindered by cellular structures and changes with pathology. In healthy axonal tracts water diffuses preferentially along the tract, but as inflammation induces axonal degeneration, water diffusion becomes more isotropic. The degeneration of these tracts is reflected in the change in the preferred direction for water diffusion at the cellular level, or Fractional Anisotropy (FA) as measured by DTI. DWI measures the Mean Diffusivity (MD), regardless of direction. In general, low-fractional anisotropy (FA) and high-mean diffusivity (MD) are found in MS lesions, but values are highly heterogeneous. However, these measures are inferred—i.e. it is necessary to posit a cellular level mechanism for the observed decrease in diffusion magnitude and directionality. For example. changes in diffusion can be due to inflammation or edema, or byproducts of myelin degradation.

Another method to assess demyelination is by multi-echo recording, which allows measure of T2 relaxation, a figure which reflects water/fat content. This is known as T2 relaxometry, and when used in integrated form with the embodiments disclosed enables measure of tissue structure differentiated by water content.

An exemplary MS assessment would include visualization of lesions in T2 and T1 weighting—dissemination in space and time. This would be a longitudinal record. Combining different MR-based measures, sensitive to different aspects of MS pathology to increase understanding of the mechanism underlying accumulation of irreversible disability. Employ perfusion MRI to quantify cerebral blood flow and volume; multi-channel receiver coils to examine the interior of lesions. Brain atrophy measures are employed for measuring cerebral volume changes and look at correlation with WM tract damage.

Machine learning algorithms may then be applied to evaluate combined data from current diagnostics and data obtained by applying the embodiments disclosed with various contrasts and acquisition parameters—structured or unstructured.

To accommodate pathology analysis for the examples provided, a salient feature of the embodiments disclosed is that they can be run in an integrated pulse sequence mode with other MRI sequences. The basic structure of the embodiments disclosed—data acquisition across a sparsely-sampled k-space trajectory, at one tissue location at a time—is operable in conjunction with most contrast-generating mechanisms.

Use of the embodiments disclosed with diffusion-weighting contrast was disclosed in FIGS. 24 and 25 which depict an integrated pulse sequence using the embodiments disclosed in conjunction with diffusion weighting, with two different positionings of the diffusion gradients within the sequence.

Such an integrated sequence could be repeated with the diffusion gradient applied along multiple axes, similarly to DTI (Diffusion Tensor Imaging). The output dataset would then allow development of a diffusion tensor, enabling determination of the FA (Fractional Anisotropy), a reflection of water flow pathways in the tissue which reflect cellular-level changes.

Along with application of both DWI and DTI contrast towards typing MS lesions and determining underlying pathological tissue changes, a sequence that enables assessment of changes in fraction of bound and free water, MTI (Magnetization Transfer Imaging), can be used to help assess myelin destruction and regeneration in progressive pathology. The aim of the MTI technique is to track changes in bound water vs. free water in tissue. The T2 decay time of bound hydrogen protons is too fast to enable direct signal recording. Instead, selective RF excitation of the bound pool of protons is done, resulting in subsequent excitation transfer to the free pool via dipole-dipole interactions. This results in saturation of the free pool and, hence, signal is reduced following subsequent application of a standard RF MRI pulse.

As with diffusion weighting, this is an indirect technique and hence different interpretations may fit the measured data—water changes can be due to edema or inflammation as well as demyelination.

One possible technique for pathology assessment is to apply the MTI technique and then compare the image recorded to textural measure acquired in the same tissue region using the embodiments disclosed and a standard tissue contrast, such as T1 or T2 weighting. In this case, the embodiments disclosed could provide an assessment of tissue degradation, which could be used as a pathology-specific calibration of the MTI technique. However, a more powerful alternative would be an integrated pulse sequence, in which the embodiments disclosed would be used in conjunction with magnetization transfer contrast—i.e. would acquire high-resolution measure of texture with texture contrast between structures of differing bound and free water concentrations provided by the MT contrast. This integrated sequence technique could be applied in pathologies for which there is a clear differentiation between the type of water (free, or bound to macromolecules) associated with the measured textural elements. Pathology in many neurologic diseases, such as MS and AD, involves changes in the myelin coating neuronal structures. Myelin contains bound hydrogen protons; free water moves in as the myelin degrades. Hence this integrated sequence could provide a much-needed measure of such pathology. And, unlike direct application of the MT imaging sequence, the integrated pulse sequence measure applied to tissue informs a clearer understanding of the pathology-linked changes in tissue texture.

Another target for integrated pulse sequence acquisition would be relaxometry. Information about pathology-linked changes in tissue can be obtained through measure of the decay time of the RF excitation—either T1, T2, or T2*—which provides information about the specific tissue environment. Hydrogen protons in different chemical environments exhibit different relaxation times. The most commonly used figure, T2 decay time, is dependent on spin-spin interactions. Variations in T2 relaxation can thus be used to discriminate among chemical environments in tissue, and can heighten tissue contrast. For instance, as myelin decomposes in diseases such as AD and MS, free water moves in. This change is reflected as a change in the local T2 time constant. The T2 decay constant is obtained by acquiring data at various times following the spin echo (or even in advance of it) as the signal decays. In relaxometry, measurements obtained in different voxels are often mapped to form an image revealing spatial variations, often pathology-induced, in T2 decay time. This mapping is subject to the resolution limits set by patient motion and SNR considerations, and is not capable of resolving fine tissue textures. However, by using a pulse sequence to acquire data by the embodiments disclosed, repeating measures at specific k-values to track signal decay, an integrated measure of very fine tissue texture can be achieved, with T2 relaxation rate providing the tissue contrast. The basic sequence would then entail defining and exciting tissue in the VOI, applying a gradient pulse to wind up to a specific k-value (point in k-space), and measuring the signal at successive times as the signal decays. By this method, information is obtained on the chemical environment of the tissue textures contributing to that point in k-space—i.e. the tissue environment of textural structures that repeat with the frequency associated with that k-value. For instance, as water has a specific T2, measure of T2 decay rate can be used to gauge changes in the free water content of the specific textural structures that contribute to signal power at that k-value.

Alternatively, a range of points in k-space can be sampled in a single TR, the various k-values being measured in succession, and then the measure being repeated multiple times while the signal decays, to track the signal decay at each k-value and enable determination of k-value vs. T2.

T2 relaxometry in human brain has been successfully used to differentiate normal from abnormal tissues. Research studies have also demonstrated the potential of relaxometry for early breast cancer detection and monitoring of therapy response. The technique has also been used to identify abnormal breast tissue, distinguishing adipose from glandular tissue types by their distinctly different T2 values. Carneiro et al., "MRI Relaxometry: Methods and Applications", Brazilian Journal of Physics, March 2006.

This measure could be done similarly looking at T2* decay, by using a gradient echo sequence to form the echo.

T1 relaxometry can be done in integrated sequence combination with the embodiments disclosed, though multiple TRs are required to track the T1 decay constant. This means that motion between acquisitions can lead to dephasing of the measure. However, as long as the VOI remains in a similar tissue environment, the measure needed is simple k-value vs. T1. Further, if the tissue region under study changes rapidly spatially, real time motion correction can be used to ensure that the VOI is repositioned at each TR to stay in the same region of tissue. Again, the requirement here is only to remain in the same tissue region, not to maintain textural phase coherence.

In certain diseases, the embodiments disclosed can provide complementary data to improve pathology assessment when used in conjunction with MRS (Magnetic Resonance Spectroscopy). MRS is a noninvasive technique that enables detection of metabolites, naturally occurring biochemicals that are used in specific metabolic activities. Commonly measured metabolites are creatine, inositol, glucose, N-acetylaspartate, and alanine and lactate, the latter two being elevated in some tumors. MRS has been used to study relative changes in metabolites in brain tumors, as a result of strokes, seizures, AD progression, and depression, as well as being applied to study muscle changes as a result of pathology. Although an abundance of studies show metabolic changes in the brain (and muscles) in subjects with various diseases, at present MRS is little used in the clinical evaluation of subjects. This is partly due to a lack of standardized methodology between clinical sites and overlap of spectral patterns between different pathologies (i.e., relative lack of specificity). Water suppression techniques are required, usually accomplished through saturating the water protons, as the ratio of water to metabolites is on the order of 10,000:1. Combining data obtained by the embodiments disclosed with MRS data could help in the calibration of the spectroscopic data and lead to a more powerful diagnostic by combination. This endeavor may bring high sensitivity and specificity metabolic information without biopsy. While MRI can locate a tumor, information from the embodiments disclosed combined with MRS can reveal tumor aggressiveness and type, allowing therapy targeting and monitoring.

As one example, clinical studies have found increased myo-inositol and decreased N-acetylaspartate in the brain of patients with suspected Alzheimer's disease, this trend continuing with disease progression through MCI (Mild Cognitive Impairment) into full-blown AD. As such, correlation of MRS data obtained in the cortical structures affected in early disease with the change in tissue texture in the cortex as measured using the embodiments disclosed, would strengthen the role of metabolite levels as a marker for pathology advancement, while developing a correlation between specific tissue damage and AD stage. Gao and Barker, "Various MRS application tools for Alzheimer's Disease and Mild Cognitive Impairment", American Journal of Neuroradiology, June 2014.

Research to date has shown that local metabolite levels can indicate changes from normal tissue, often correlating with pathology development. For instance, measure of metabolite signature spatially across a tumor can be analyzed to measure tissue heterogeneity, an indicator of tumor aggressiveness. The embodiments disclosed can provide measure of the spatial variation of angiogenic vasculature across that same tumor to correlate the degree of vascular density and disorder with the MRS metabolite read.

The disclosed embodiments can be employed to look for heterogeneity across a region and at changes in k-space power spectrum with reference to normal spectrum.

Another target for combining the embodiments disclosed with MRS is for clinical evaluation of tumor development. Tumor assessment is required for typing and for determining target volume for radiation therapy. Brain tumors exhibit markedly different MRS spectra from normal brain tissue. Further, tumor regions exhibit clear metabolite inhomogeneity, the spectrum from the necrotic core of a high-grade brain tumor being quite different from that from the actively growing rim. Peritumoral edema exhibits a much different metabolite complement than is found in a region of tumor invasion into surrounding brain tissue. MRSI (MRS Imaging) can be used to map out the metabolite variability in the region of a tissue. However, the limited spatial resolution (about 1 cm3) makes imaging of small tumor regions problematic due to the relatively large voxel size and to partial volume effects. While the clear variation in metabolites in tumor regions point to the potential for application of MRS, it has not been accepted as a routine clinical tool.

While MRI is without doubt the most sensitive modality available for the detection of brain tumors, its specificity is low—different tumor/lesion types, can share a similar MRI appearance. Determination of tumor grade, or differentiating between neoplastic and non-neoplastic lesions, is important, as high-grade brain tumors need to be treated more aggressively than low-grade tumors. If a lesion can be confidently diagnosed as non-neoplastic, an invasive brain biopsy procedure may be avoided and a different treatment course, depending on the lesion etiology, may be considered. Differentiation between tumors and non-neoplastic lesions using conventional MRI may be challenging. While MRI is a sensitive technique for detection of brain lesions, the specificity and capability of conventional MRI for distinguishing between benign and malignant lesions is limited. Horská and Barker, "Imaging of Brain Tumors: MR Spectroscopy and Metabolic Imaging", Neuroimaging Clinics of North America, August 2010.

Data obtained with the embodiments disclosed can be combined with that obtained by MRI and MRS, to provide better specificity for pathology assessment. The embodiments disclosed, in their ability to measure fine structure, can provide pertinent information to assist in tumor typing, by assessing the vasculature within and surrounding the tumor to determine the degree of angiogenesis across the tumor from the center out past the periphery of the lesion as seen with MRI, part of the measure being evaluation of extent of the angiogenic vasculature into the surrounding tissue. In this way, differentiation between aggressive/non-aggressive tumors can be made with much better certainty than can be achieved using only MRS and MRI. The metabolite variation that arises from, say, edema, will be associated with a very different tissue texture, than would that associated with angiogenic vasculature. Embodiments disclosed measures angiogenic changes across tumor.

Figure 31:
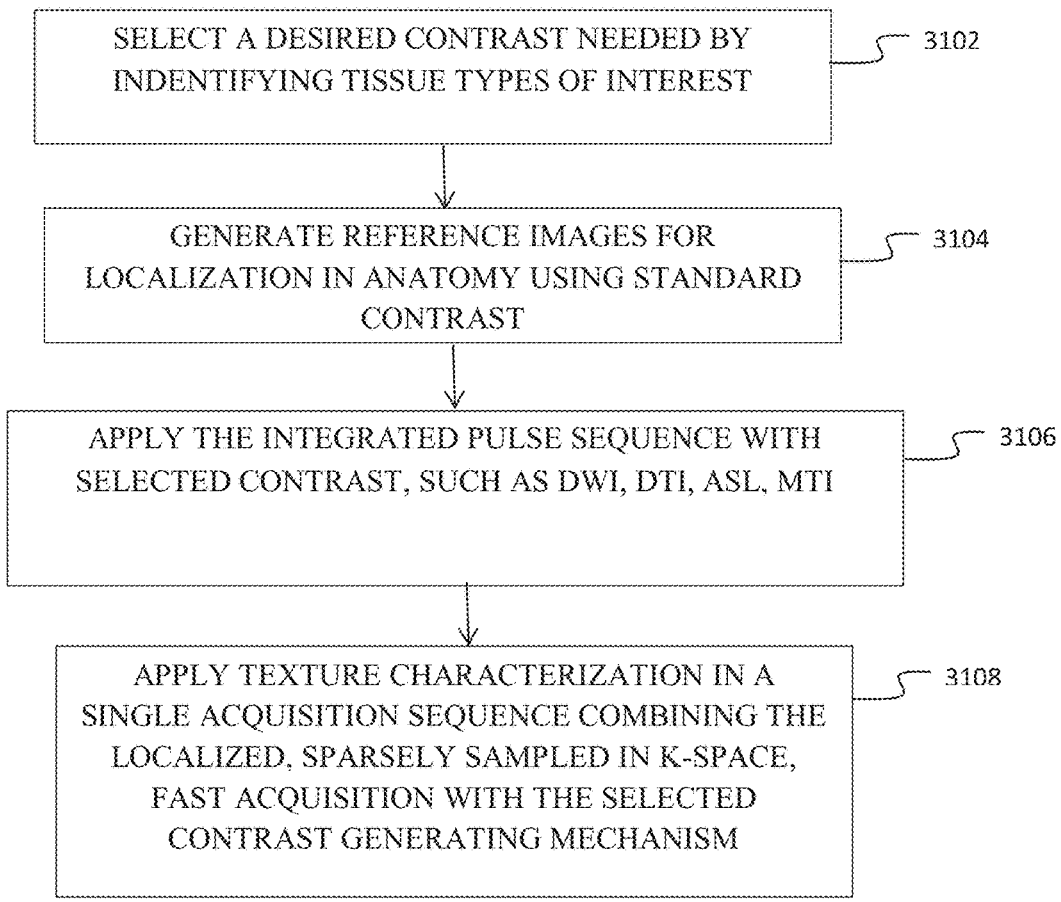
FIG. 31 is a flow chart demonstrating

A typical workflow for application of an integrated pulse sequence, combining the embodiments disclosed with additional novel contrast methods, might be accomplished as shown in FIG. 31.

Select a desired contrast needed by identifying tissue types of interest, step 3102.

Reference images are then generated for localization in anatomy using standard contrast such as T1, T2, T2*, IR, step 3104.

Apply the integrated pulse sequence with selected contrast, such as DWI, DTI, ASL, MTI, step 3106, and apply the embodiments disclosed for texture characterization in a single acquisition sequence combining the localized, sparsely sampled in k-space, fast acquisition of the embodiments disclosed with the selected contrast generating mechanism, step 3108.

The novel features of the embodiments disclosed that enable much higher resolution measurement than is achievable with MR imaging are 1) sampling at targeted spatial locations, the size of the sampled volume being determined by the targeted disease/pathology, and 2) selective sampling in k-space. In MR imaging, acquisition is across a large, spatially-encoded 3D volume, and encompasses continuous k-space measure from k=0 up through to the highest k-value of interest. Such a measure requires acquisition of a very large data set over a temporal course long enough that patient motion limits feature resolution. By localizing the measure to one location in sample space, and sampling only highly selective regions in k-space, the embodiments disclosed provides immunity to patient motion, thus enabling a high resolution textural measure to be acquired within one TR. The measured textural data is similar to that acquired by biopsy, with none of the procedural risks. Further, the sampling errors inherent in biopsy/pathology are obviated because, using the embodiments disclosed, an entire organ can be covered with individual, motion-immune, localized measurements.

The k-space sampling required to adequately characterize tissue texture varies both with disease, and with the stage of pathology development. Though, as with many measurements, a basic knowledge of the disease can be used to select acquisition parameters, enhanced parameter optimization can be achieved through use of "scout" acquisitions, that provide general information on the distribution of power through k-space at a certain location. For instance, as the optimal length of the sampled volume, the VOI (Volume of Interest), varies with the textural wavelength(s) of interest in the tissue under study, an idea of the approximate range/values of interest in k-space would help in selecting VOI dimensions.

In bone, say, as the trabecular number decreases with degradation, it would be advantageous to vary the VOI length to keep the ratio of feature size (textural number) to sampling length relatively constant. In this case, TbN is the feature length of interest, not TbSp or TbTh, as TbN determines the repeat number relative to the VOI acquisition length. Use of scout images to determine the relative position(s) in k-space of the peak signal power, would enable optimal setting of the VOI length.

To affect the Scout measure, one method would be to select optimal tissue contrast based on what is known of the pathology, and acquire data for sufficient time and TRs to gauge generally where the power lies in k-space for a single orientation acquisition. These scout measures can be made using gradient ON acquisition to sweep through a range of values, keeping the sweep slow enough to obtain sufficient SNR to gauge where the textural power lies in k-space. Thus, scout measure would be accomplished by first acquiring signal data across a large enough region in k-space to encompass the textural k-values associated with the tissue under study across the range of health into disease. Real-time decision on what range(s) demonstrate importance in the initial scan can then be selected for more detailed tracking by slower gradient ON acquisition, or targeting specific k-values to measure. Data acquisition will then be successively focused on narrower and narrower ranges to zero in on k-space regions that hold the highest information content. In this undertaking, it must be kept in mind that, regions of little textural features can, in their very lack of texture, be of import in disease progression In some cases, where pathology is mirrored in changes across large regions of k-space, acquisition could be with gradient on and slow sampling across the entire region.

As another example, scout acquisitions could be used to determine the k-value of interest for a relaxometry measure. Since most biologic tissue textures are non-crystalline, a finite band in k-space, representative of the textural k-value span, could be identified using gradient ON acquisition. This could be achieved by successively sampling sub regions across k-space to find the region of interest where the textural power lies. Once the k-band of interest is determined, the decay of RF excitation across that band can be measured as the signal decays, the sampled region being selected using gradient ON acquisition.

Scout images can be used to investigate sensitivity to exact positioning.

Figure 32:
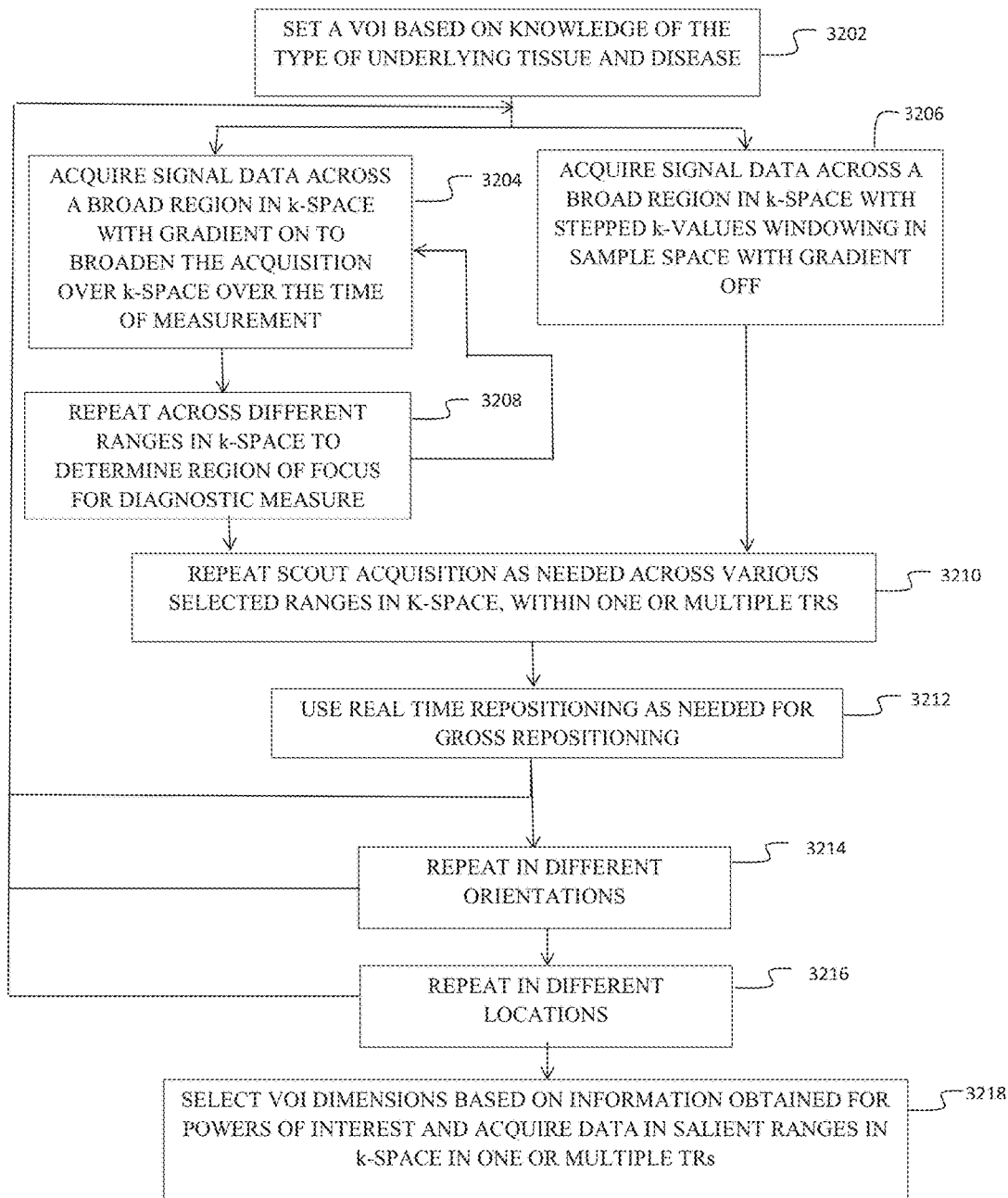
FIG. 32 is a flow chart demonstrating procedural flow using scout acquisitions; and, FIGS. 33A and 33B are a flow chart demonstrating work flow for calibration of texture characterization for application in diagnosis of targeted diseases.

Thus, as shown in FIG. 32 a procedural flow using scout acquisitions might entail:

Setting a VOI based on knowledge of the type of underlying tissue and disease, step 3202, and acquiring signal data across some broad regions in k-space. The regions can be set either by acquisition with a gradient on to broaden the acquisition in k-space over the time of the measurement, step 3204, or with stepped k-values, by windowing in sample space, step 3206. The former procedure is preferred as it allows sampling of a larger number of textural repeats to better determine where the power of interest lies. This measure can be repeated across different ranges in k-space, step 3208, to determine the k-space region on which to focus for the diagnostic measure.

The scout acquisition can be repeated as needed across various selected ranges in k-space, within one or multiple TRs, step 3210. The loss of coherence between TRs does not matter as long as the measure remains within a similar region of tissue texture. Real time repositioning could be used here as needed for gross repositioning, step 3212.

This scout method can be repeated in as many different orientations, step 3214, and as many different locations as desired, step 3216.

Using the information obtained for the power(s) of interest, VOI dimensions can be selected to allow sampling of a minimum of 4 textural repeats (more would be better, though the shorter the VOI the easier it is to maintain textural homogeneity across its dimensions), step 3218, and data will be acquired across the salient ranges in k-space, in one or multiple TRs.

It is to be noted that features of interest are not just in the ranges where there is much spectral power, but also includes ranges that are of interest due to a specific lack of signal intensity there.

As briefly described above with respect to various applications of the embodiments disclosed, machine learning in development and application of medical diagnostics can be applied to facilitate 1) calibration of the diagnostic and determination of optimal data acquisition parameters, 2) identification of the biomarkers of a disease, and 3) ongoing use of the diagnostic method in both individual and population health spheres to ensure optimal extraction of diagnostic information. Machine learning can be applied in either a supervised learning method, when it is known what output quantity/biomarker (such as trabecular bone thickness) is to be measured, or it can be run in an unsupervised mode, in which the algorithm searches the data sets it is given looking for common features. In the former case, supervised learning, the accuracy with which a new diagnostic measures the known quantity is determined by comparison to some sort of ground truth measure, and the machine learning can be used to optimize the data acquisition parameters for the diagnostic. In the case of unsupervised learning, once the features common among the various data sets are extracted—in the case of the embodiments disclosed, the power distribution in certain regions of the textural wavelength spectrum—they can then, if desired, be correlated with other known information about the targeted tissue such as state of health/disease.

Machine learning can be an instrumental part of calibrating the embodiments disclosed as a diagnostic tool in each disease in the large range of diseases for which variation in tissue texture is a marker of disease onset and progression. The application of machine learning towards this goal is facilitated by use of a source of ground truth measure of pertinent tissue texture, to provide input for determination of the salient textural features that track pathology, features which are currently not measurable in vivo, and for validation of the diagnostic data obtained by the embodiments disclosed. This ground truth can be provided through use of tissue samples from various organs, reflecting various states of health and pathology in disease. Because there is no motion blurring, use of ex vivo tissue enables generation of high quality ground truth data sets for calibration of the embodiments disclosed by use of techniques such as microCT, pathology staining, and MRI microscopy. (Szeverenyi et al., MR imaging of liver microstructure in hepatic fibrosis and cirrhosis at 11.7T, ISMRM 2016).

Figure 33A:
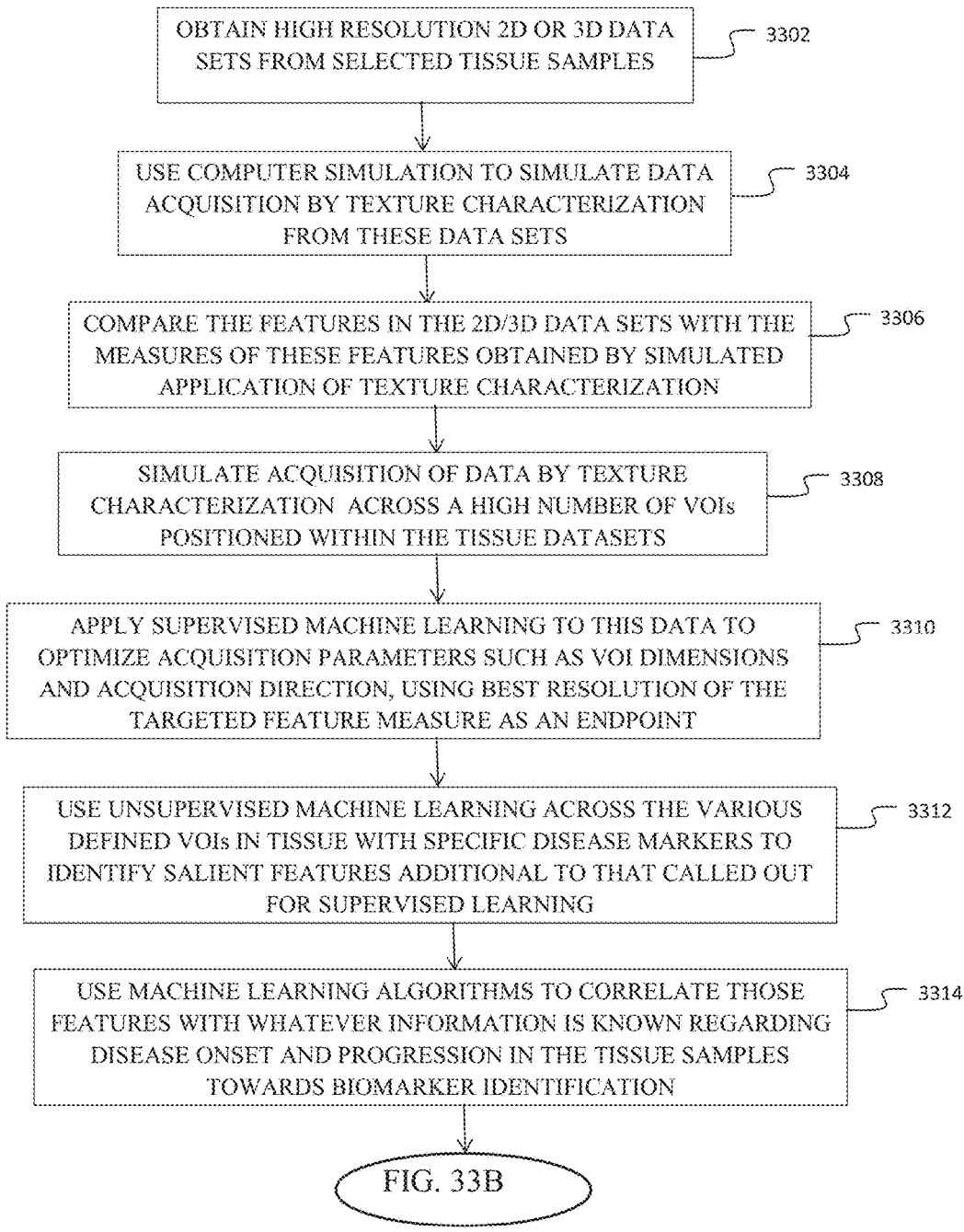

The work flow for calibration of the embodiments disclosed for application in diagnosis of targeted diseases is described in FIG. 33 as the following: Obtain high resolution 2D or 3D data sets from selected tissue samples by use of microCT, MRI microscopy, or pathology, step 3302. Use computer simulation to simulate data acquisition by the embodiments disclosed for texture characterization from these data sets by using the data sets as input for simulating application of a selected contrast mechanism, selectively exciting a simulated volume of interest (VOI) employing a plurality of simulated time varying radio frequency signals and applied gradients, applying a simulated encoding gradient pulse to induce phase wrap to create a spatial encode for a specific k-value and orientation, the specific k-value determined based on the texture within the VOI, initiating a series of simulated gradients to produce k-value encodes, a resulting k-value set being a subset of that required to produce an image of the VOI, recording multiple sequential samples of simulated NMR RF signal encoded with the k-value set and post processing the recorded NMR signal samples to produce a data set of signal vs k-values for k-values in the k-value set, to characterize a simulation of the textural features of tissue in the VOI, step 3304. Compare the features in the 2D/3D data sets with the measures of these features obtained by simulated application of texture characterization, step 3306. Simulate acquisition of data by the embodiments disclosed for texture characterization across a high number of VOIs positioned within the tissue datasets, step 3308, and apply supervised machine learning to this data to optimize acquisition parameters such as VOI dimensions and acquisition direction, using best resolution of the targeted feature measure as an endpoint, step 3310. Use unsupervised machine learning across the various defined VOIs in tissue with specific disease markers to identify salient features additional to that called out for supervised learning, step 3312. Use machine learning algorithms to correlate those features with whatever information is known regarding disease onset and progression in the tissue samples towards biomarker identification, step 3314. Determine the sparsely sampled data set is that is needed for measuring the tissue biomarkers towards disease diagnosis, step 3316. Use machine learning to determine the strength of the diagnostic assessment provided by the embodiments disclosed, step 3318. Acquire data by the embodiments disclosed in the actual SNR environment of the MR scanner, on the same tissue samples, for comparison to the ground truth datasets, step 3320. Repeat the above steps towards optimization of acquisition parameters and calibration of the embodiments disclosed towards high resolution, robust textural measure, step 3322.

As previously described, machine learning may be employed using the tissue texture measurement methods of the various embodiments to enhance determining pathology of a tissue type. A contrast mechanism is selected enhancing the contrast between component tissue types in a multiphase biologic sample which may also be employed for measurement with a MR imaging process. The selected contrast mechanism is applied and a volume of interest (VOI) is selectively excited employing a plurality of time varying radio frequency signals and applied gradients. An encoding gradient pulse is applied to induce phase wrap to create a spatial encode for a specific k-value and orientation, the specific k-value determined based on texture within the VOI. A series of gradients is then initiated to produce k-value encodes, a resulting k-value set being a subset of that required to produce an image of the VOL Multiple sequential samples of the NMR RF signal encoded with the k-value set are recorded and post processed to produce a data set of signal vs k-values for k-values in the k-value set, to characterize textural features of tissue in the VOL Machine learning is then applied to a power density distribution of a textural wavelength of the k-value set to identify biomarkers for diagnosis of pathology of the tissue.

The method may be further enhanced by applying machine learning to identify a correlation between textural features and features in a power density spectrum of the textural wavelengths. Machine learning may also be applied to the textural features using additional sources of diagnostic information such as patient histories, exam records, imaging, serum markers, physical performance, and cognitive tests for extraction of diagnostic data to determine a disease assessment. Machine learning may also be applied to determine weighting of the various diagnostic information sources in the ultimate diagnosis.

Input for machine learning may also be created by selecting a plurality of biologic phantoms having tissue pathology from healthy through diseased. A contrast mechanism enhancing the contrast between component tissue types in each biologic phantom is selected for measurement with a MR imaging process and the selected contrast mechanism is applied in an MR pulse sequence. A volume of interest (VOI) in each biologic phantom is excited employing a plurality of time varying radio frequency signals and applied gradients. An encoding gradient pulse is applied to induce phase wrap to create a spatial encode for a specific k-value and orientation, the specific k-value determined based on anticipated texture within the VOL A series of gradients to produce k-value encodes, a resulting k-value set being a subset of that required to produce an image of the VOI are then applied and multiple sequential samples of the NMR RF signal encoded with the k-value set are recorded to provide texture measurement of each of the biologic phantoms.

Following calibration and optimization of the embodiments disclosed in various disease applications, the texture measurements produced by the embodiments would then be used as clinical diagnostic tools. Due to the ability to measure textural features to high-resolution in a size realm previously unmeasurable, and the fact that tissue changes are a very sensitive measure of pathology progression, the embodiments disclosed produce high information content data. Also, as it is a fast and hence minimal cost to add the disclosed embodiments to an MRI scan, barriers to adoption and use are low. As such, the disclosed embodiments will be one of the important drivers in the clinical diagnosis of disease, and can thus help in weighting the efficacy of the various other sources of diagnostic information that are applied. Machine learning algorithms would be applied to correlate all the data from the multiple sources of pertinent data acquired towards patient health assessment, including data acquired by the embodiments disclosed, patient histories, exam records, imaging, serum markers, physical performance, cognitive tests, and any other types of diagnostic information available. The range of diagnostic information available on a patient would be fed into a machine algorithm that would, using the sum of this data, provide both an optimized diagnosis and a weighting of the importance of the various diagnostic inputs to the algorithm, as well as an evaluation of the level of certainty of the diagnosis. This ability to assess diagnostic accuracy and weighting in clinical practice would be informed by use of machine learning in the sphere of large population health data sets towards determination of the efficacy of many currently used diagnostics. Additionally, correlation with all other data sets will provide ongoing calibration and optimization of the embodiments disclosed, as well as maximum extraction of diagnostic data.

Having now described various embodiments of the invention in detail as required by the patent statutes, those skilled in the art will recognize modifications and substitutions to the specific embodiments disclosed herein. Such modifications are within the scope and intent of the present invention as defined in the following claims.

What is claimed is:

1. A method for calibration of Magnetic Resonance (MR) tissue texture measurement comprising:

using microCT, MRI microscopy, or pathology to obtain high resolution 2D or 3D tissue data sets from selected tissue samples;

simulating data acquisition using the data sets as input for applying a selected contrast mechanism, selectively exciting a simulated volume of interest (VOI) employing a plurality of simulated time varying radio frequency signals and applied gradients, applying a simulated encoding gradient pulse to induce phase wrap to create a spatial encode for a specific k-value and orientation, the specific k-value determined based on the texture within the VOI, initiating a series of simulated gradients to produce k-value encodes, a resulting k-value set being a subset of that required to produce an image of the VOI, recording multiple sequential samples of simulated NMR RF signal encoded with the k-value set and post processing the recorded NMR signal samples to produce a data set of signal vs k-values for k-values in the k-value set, to characterize a simulation of the textural features of tissue in the VOI;

comparing features in the 2D/3D data sets with the simulation of textural features to provide comparative datasets;

repeating the step of simulating data acquisition across a high number of VOIs positioned within the tissue datasets;

applying supervised machine learning to the simulation of textual features and to the comparative datasets to optimize acquisition parameters including VOI dimensions and acquisition direction, using best resolution of the targeted feature measure as an endpoint.

2. The method as defined in claim 1 further comprising:
using unsupervised machine learning across the defined VOIs in tissue with specific disease markers to identify salient features additional to that called out for supervised learning;
using machine learning algorithms to correlate those features with information known regarding disease onset and progression in the tissue samples towards biomarker identification;
determining a sparsely sampled data set needed for measuring the tissue biomarkers towards a disease diagnostic assessment;
using machine learning algorithms to determine the strength of the diagnostic assessment;
acquiring data in the actual SNR environment of a MR scanner by applying the selected contrast mechanism, selectively exciting a volume of interest (VOI) employing a plurality of time varying radio frequency signals and applied gradients, applying an encoding gradient pulse to induce phase wrap to create a spatial encode for a specific k-value and orientation, the specific k-value determined based on texture within the VOI, initiating a series of gradients to produce k-value encodes, a resulting k-value set being a subset of that required to produce an image of the VOI, recording multiple sequential samples of the NMR RF signal encoded with the k-value set and post processing the recorded NMR signal samples to produce a data set of signal vs k-values for k-values in the k-value set, to characterize textural features of tissue in the VOI, on the same tissue samples, for comparison to the ground truth datasets;
repeating the recited steps to obtain optimization of acquisition parameters and calibration of the embodiments disclosed towards high resolution, robust textural measure.

3. A method for interpretation of Magnetic Resonance (MR) tissue texture measurement for determining pathology of a tissue type comprising:
selecting a contrast mechanism enhancing the contrast between component tissue types in a multiphase biologic sample for measurement with a MR imaging process;
applying the selected contrast mechanism;
selectively exciting a volume of interest (VOI) employing a plurality of time varying radio frequency signals and applied gradients;
applying an encoding gradient pulse to induce phase wrap to create a spatial encode for a specific k-value and orientation, the specific k-value determined based on texture within the VOI;
initiating a series of gradients to produce k-value encodes, a resulting k-value set being a subset of that required to produce an image of the VOI;
recording multiple sequential samples of the NMR RF signal encoded with the k-value set;
post processing the recorded NMR signal samples to produce a data set of signal vs k-values for k-values in the k-value set, to characterize textural features of tissue in the VOI; and
applying machine learning to a power density distribution of a textural wavelength of the k-value set to identify bio-markers for diagnosis of pathology of the tissue.

4. The method of claim 3 further comprising applying machine learning to identify a correlation between textural features and features in a power density spectrum of the textural wavelengths.

5. The method of claim 3 further comprising applying machine learning to the textural features and diagnostic information sources using additional sources of diagnostic information such as patient histories, exam records, imaging, serum markers, physical performance, and cognitive tests for extraction of diagnostic data to determine a disease assessment.

6. The method of claim 5 further comprising applying machine learning to determine weighting of the various diagnostic information sources in the ultimate diagnosis.

7. The method of claim 3 further comprising:
selecting a plurality of biologic phantoms having tissue pathology from healthy through diseased;
selecting a contrast mechanism enhancing the contrast between component tissue types in each biologic phantom for measurement with a MR imaging process;
applying the selected contrast mechanism;
selectively exciting a volume of interest (VOI) in each biologic phantom employing a plurality of time varying radio frequency signals and applied gradients;
applying an encoding gradient pulse to induce phase wrap to create a spatial encode for a specific k-value and orientation, the specific k-value determined based on texture within the VOI;
initiating a series of gradients to produce k-value encodes, a resulting k-value set being a subset of that required to produce an image of the VOI; and,
recording multiple sequential samples of the NMR RF signal encoded with the k-value set to provide texture measurement of each of the biologic phantoms.
post processing the recorded NMR signal samples to produce a data set of signal vs k-values for k-values in the k-value set, to characterize textural features of tissue in the VOI.

8. A method for pathology assessment employing tissue texture using magnetic resonance (MR) comprising:
selectively exciting a volume of interest (VOI) in tissue subject to motion employing a plurality of time varying radio frequency signals and applied gradients;
applying an encoding gradient pulse to induce phase wrap to create a spatial encode for a specific k-value and orientation, the specific k-value determined based on texture within the VOI;
initiating a series of gradients to produce k-value encodes giving a resulting k-value set;
recording multiple sequential samples of the NMR RF signal encoded with the k-value set within a single excitation of the VOI, the selectively excited VOI moving with the tissue;
post processing the recorded NMR signal samples to produce a data set of signal vs k-values for k-values in the k-value set, to characterize textural features of tissue in the VOI.

* * * * *